US010537609B2

(12) United States Patent
Lillehoj et al.

(10) Patent No.: US 10,537,609 B2
(45) Date of Patent: Jan. 21, 2020

(54) MUC1 DECOY PEPTIDES FOR TREATMENT AND PREVENTION OF BACTERIAL INFECTIONS

(71) Applicants: UNIVERSITY OF MARYLAND, BALTIMORE, Baltimore, MD (US); THE UNITED STATES OF AMERICA AS REPRESENTED BY THE DEPARTMENT OF VETERANS AFFAIRS, Washington, DC (US)

(72) Inventors: Erik P. Lillehoj, West Friendship, MD (US); Avelino C. Verceles, Elkridge, MD (US); Simeon E. Goldblum, Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 15/630,165

(22) Filed: Jun. 22, 2017

(65) Prior Publication Data

US 2017/0319655 A1 Nov. 9, 2017

Related U.S. Application Data

(63) Continuation-in-part of application No. PCT/US2015/000313, filed on Dec. 23, 2015.

(60) Provisional application No. 62/197,299, filed on Jul. 27, 2015, provisional application No. 62/096,166, filed on Dec. 23, 2014.

(51) Int. Cl.
*A61K 38/17* (2006.01)
*C07K 14/47* (2006.01)
*A61K 31/546* (2006.01)
*G01N 33/569* (2006.01)
*A61K 38/00* (2006.01)

(52) U.S. Cl.
CPC ........ *A61K 38/1735* (2013.01); *A61K 31/546* (2013.01); *C07K 14/4727* (2013.01); *G01N 33/56911* (2013.01); *G01N 33/56916* (2013.01); *A61K 38/00* (2013.01); *G01N 2333/195* (2013.01); *G01N 2333/21* (2013.01); *G01N 2333/245* (2013.01); *G01N 2333/4725* (2013.01); *Y02A 50/47* (2018.01); *Y02A 50/473* (2018.01); *Y02A 50/478* (2018.01); *Y02A 50/481* (2018.01)

(58) Field of Classification Search
None
See application file for complete search history.

(56) References Cited

U.S. PATENT DOCUMENTS 5,827,666 A * 10/1998 Finn .................... C07K 14/005
435/7.1
2004/0157278 A1 8/2004 Astle et al.
2014/0107189 A1 4/2014 Bancel et al.

FOREIGN PATENT DOCUMENTS

| WO | 03/042240 | 5/2003 |
|---|---|---|
| WO | 2004/033667 | 4/2004 |
| WO | 2008/040059 | 4/2008 |
| WO | 2008/147405 | 12/2008 |
| WO | 2011/024412 | 3/2011 |
| WO | 2013/025972 | 2/2013 |

OTHER PUBLICATIONS

Mitchell (Helicobacter pylori, Physiology and Genetics, "Chapter 2: Epidemiology of Infection," Mobley HLT, Mendz GL, Hazell SL, editors. Washington (DC): ASM Press; 2001; downloaded from www.ncbi.nlm.nih.gov/books/NBK2421) (Year: 2001).*
Wong ("Update on Management of Helicobacter Pylori Infection," The Hong Kong Medical Diary, vol. 15, 2010, pp. 8-10) (Year: 2010).*
Driscoll et al. ("The Epidemiology, Pathogenesis and Treatment of Pseudomonas aeruginosa Infections," Drugs, vol. 67, 2007, pp. 351-368) (Year: 2007).*
McAuley et al., "MUC1 cell surface mucin is a critical element of the mucosal barrier to infection", The Journal of Clinical Investigation, 117, 8: 2313-2324 (2007).
(Continued)

*Primary Examiner* — Christina Bradley
(74) *Attorney, Agent, or Firm* — Wenderoth, Lind & Ponack, L.L.P.

(57) ABSTRACT

*Pseudomonas aeruginosa* flagellin protein recruits the mammalian host sialidase enzyme neuraminidase-1 (NEU1) to remove sialic acid residues from the extracellular domain of the mammalian cell-surface protein MUC1 (MUC1-ED), thereby exposing a cryptic binding site on the MUC1-ED protein backbone for flagellin binding. NEU1-driven MUC1-ED desialylation rapidly increases *P. aeruginosa* adhesion to the airway epithelium. MUC1-ED desialylation also increases MUC1-ED cleavage and shedding from the cell surface, where desialylated, shed MUC1-ED competitively blocks *P. aeruginosa* adhesion to cell-associated MUC1-ED. Presented herein are data showing that exogenously-administered, deglycosylated MUC1-ED peptides reduced adhesion of *P. aeruginosa* to airway epithelial cells. Also presented are data showing that administration of *P. aeruginosa* to mice in combination with deglycosylated MUC1-ED decreased *P. aeruginosa* recovered from the lungs at 48 hr and 72 hr post-infection. Such findings are extended to the methods of treatment and prevention of bacterial infections defined herein.

9 Claims, 20 Drawing Sheets

Specification includes a Sequence Listing.

(56) References Cited

OTHER PUBLICATIONS

Linden et al., "MUC1 Limits *Helicobacter pylori* Infection both by Steric Hindrance and by Acting as a Releasable Decoy", PLoS Pathogens, 5(10): 1-14(2009).
Every et al., "Muc1 Limits *Helicobacter felis* Binding to Gastric Epithelial Cells But Does not Limit Colonization and Gastric Pathology Following Infection", Helicobacter, 13: 489-493 (2008).
International Search Report and Written Opinion of the International Searching Authority, dated Mar. 24, 2017, in corresponding International Application No. PCT/US15/00313.
Extended European Search Report dated Jun. 14, 2018 in European Application No. 15873806.2.
Lillehoj et al., "NEU1 Sialidase Expressed in Human Airway Epithelia Regulates Epidermal Growth Factor Receptor (EGFR) and MUC1 Protein Signaling", The Journal of Biological Chemistry, 287(11):8214-8231 (2012).
Lillehoj et al., "Cellular and Molecular Biology of Airway Mucins", International Review of Cell and Molecular Biology, 303:139-202 (2013).
Kato et al., "MUC1 expression by human airway epithelial cells mediates *Pseudomonas aeruginosa* adhesion", Frontiers in Bioscience (Elite Edition), 2:68-77 (2010).
European Patent Office Communication pursuant to Article 94(3) EPC, dated Nov. 29, 2019 in corresponding European Patent Application No. 15 873 806.2-1118.

* cited by examiner

Fig. 1
A.
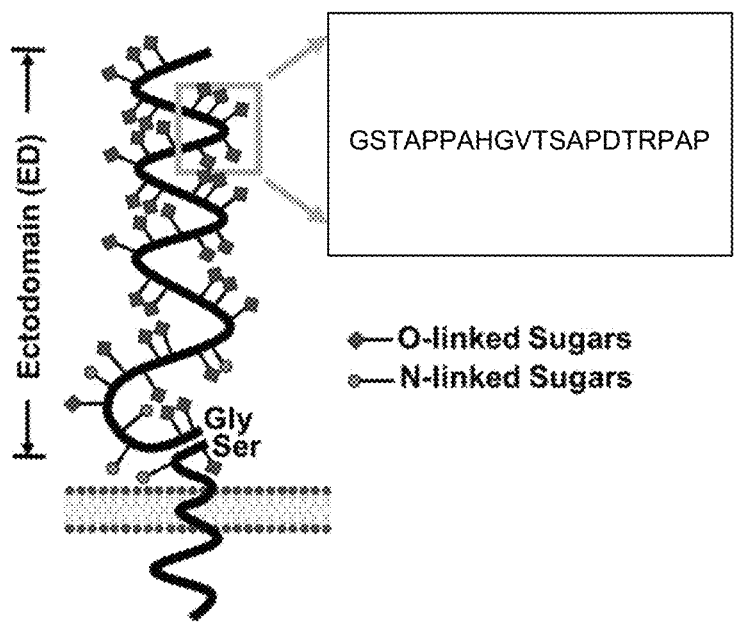
GSTAPPAHGVTSAPDTRPAP
← O-linked Sugars
← N-linked Sugars
B.
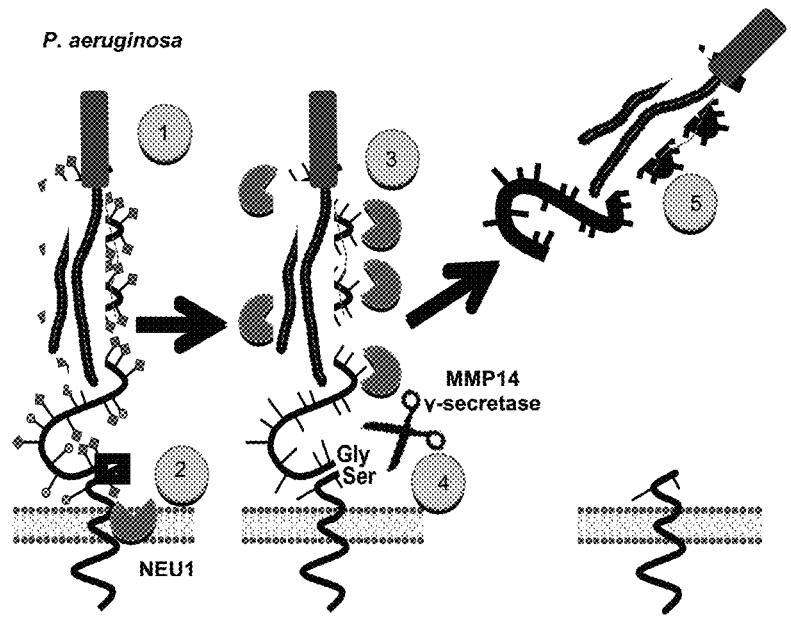

Fig. 2

```
   1    MTPGTQSPFF LLLLLTVLTV VTGSGHASST PGGEKETSAT QRSSVPSSTE KNAVSMTSSV
  61    LSSHSPGSGS STTQGQDVTL APATEPASGS AATWGQDVTS VPVTRPALGS TTPPAHDVTS
 121    APDNKPAPGS TAPPAHGVTS APDTRPAPGS TAPPAHGVTS APDTRPAPGS TAPPAHGVTS
 181    APDTRPAPGS TAPPAHGVTS APDTRPAPGS TAPPAHGVTS APDTRPAPGS TAPPAHGVTS
 241    APDTRPAPGS TAPPAHGVTS APDTRPAPGS TAPPAHGVTS APDTRPAPGS TAPPAHGVTS
 301    APDTRPAPGS TAPPAHGVTS APDTRPAPGS TAPPAHGVTS APDTRPAPGS TAPPAHGVTS
 361    APDTRPAPGS TAPPAHGVTS APDTRPAPGS TAPPAHGVTS APDTRPAPGS TAPPAHGVTS
 421    APDTRPAPGS TAPPAHGVTS APDTRPAPGS TAPPAHGVTS APDTRPAPGS TAPPAHGVTS
 481    APDTRPAPGS TAPPAHGVTS APDTRPAPGS TAPPAHGVTS APDTRPAPGS TAPPAHGVTS
 541    APDTRPAPGS TAPPAHGVTS APDTRPAPGS TAPPAHGVTS APDTRPAPGS TAPPAHGVTS
 601    APDTRPAPGS TAPPAHGVTS APDTRPAPGS TAPPAHGVTS APDTRPAPGS TAPPAHGVTS
 661    APDTRPAPGS TAPPAHGVTS APDTRPAPGS TAPPAHGVTS APDTRPAPGS TAPPAHGVTS
 721    APDTRPAPGS TAPPAHGVTS APDTRPAPGS TAPPAHGVTS APDTRPAPGS TAPPAHGVTS
 781    APDTRPAPGS TAPPAHGVTS APDTRPAPGS TAPPAHGVTS APDTRPAPGS TAPPAHGVTS
 841    APDTRPAPGS TAPPAHGVTS APDTRPAPGS TAPPAHGVTS APDTRPAPGS TAPPAHGVTS
 901    APDTRPAPGS TAPPAHGVTS APDTRPAPGS TAPPAHGVTS APDNRPALGS TAPPVHNVTS
 961    ASGSASGSAS TLVHNGTSAR ATTTPASKST PFSIPSHHSD TPTTLASHST KTDASSTHHS
1021    SVPPLTSSNH STSPQLSTGV SFFFLSFHIS NLQFNSSLED PSTDYYQELQ RDISEMFLQI
1081    YKQGGFLGLS NIKFRPGSVV VQLTLAFREG TINVHDVETQ FNQYKTEAAS RYNLTISDVS
1141    VSDVPFPFSA QSGAGVPGWG IALLVLVCVL VALAIVYLIA LAVCQCRRKN YGQLDIFPAR
1201    DTYHPMSEYP TYHTHGRYVP PSSTDRSPYE KVSAGNGGSS LSYTNPAVAA TSANL
```

MUC1 DECOY PEPTIDES FOR TREATMENT AND PREVENTION OF BACTERIAL INFECTIONS

STATEMENT OF FEDERALLY SPONSORED RESEARCH AND DEVELOPMENT

This invention was made with government support under Grant Numbers HL084223 and HL070155 awarded by The National Institutes of Health. The government has certain rights in the invention.

BACKGROUND OF INVENTION

Acute and chronic *Pseudomonas aeruginosa* colonization and infection are a major cause of human morbidity and mortality worldwide. *P. aeruginosa* is a Gram-negative, flagellated, opportunistic human pathogen typically colonizing and/or infecting debilitated and immunocompromised patients (Pier and Ramphal, 2010). In the respiratory tract, *P. aeruginosa* is one of the most common and lethal pathogens, responsible for acute ventilator-associated pneumonia with directly attributable mortality rates of 40% (Brewer et al., 1996). In individuals with cystic fibrosis, lifelong *P. aeruginosa* lung infection leads to respiratory failure and premature death (Prince, 1992). *P. aeruginosa* infections worsen the prognosis for bronchiectasis and chronic obstructive pulmonary disease patients (Novosad and Barker, 2012). *P. aeruginosa* also plays a major role in the pathogenesis of extrapulmonary diseases, including urinary tract infection, skin infections in hospital burn units, and surgical wound and bloodstream infections.

Treatment of *P. aeruginosa* infections is complicated by the fact that this bacterial pathogen is notorious for being naturally resistant to a large range of antibiotics. Therefore, alternative treatment strategies are urgently needed for use in treating and preventing *P. aeruginosa* infections.

BRIEF SUMMARY OF INVENTION

The mucin-1 (MUC1) transmembrane protein serves as an initial binding site for bacteria, such as *P. aeruginosa*, to the surface of airway epithelial cells (ECs) in animals. In particular, and as disclosed herein, it has been found that bacterial flagellin binds to the ectodomain (ED) of MUC1 while the protein is expressed on the surface of ECs. As further disclosed herein, a free form of MUC1-ED has been found to competitively block *P. aeruginosa* adhesion to cell-associated MUC1-ED. These results form the basis for each embodiment of the present invention.

In a first embodiment, the invention is directed to peptides based on the free form of MUC1-ED, termed "MUC1 decoy peptides" herein. In a related embodiment, the invention is directed to pharmaceutical formulations comprising MUC1 decoy peptides and pharmaceutically acceptable carriers or diluents.

In a second embodiment the invention is directed to using MUC1 decoy peptides to interfere with adhesion of *P. aeruginosa* to cells of a subject. Such interference can be used in the treatment and prevention of bacterial infections in animals, such as humans.

As also disclosed herein, *P. aeruginosa* binding to MUC1-ED induces cleavage of MUC1 and shedding of the ectodomain from the cell surface. The shed MUC1-ED can be detected in biological samples, such as bronchoalveolar lavage fluid (BALF). These results form the basis of a third embodiment of the present invention, namely methods for determining whether a subject has been colonized by a bacteria that can induce MUC1-ED shedding or has an infection of such a bacteria.

Turning back to the first embodiment, the present invention thus includes MUC1 decoy peptides. Each of the decoy peptides of the invention can be generally characterized as having at least 15 amino acids of the MUC1-ED repeat sequence GSTAPPAHGVTSAPDTRPAP, set forth in SEQ ID NO:1, or a variation thereof.

In aspects of this embodiment, the MUC1 decoy peptide may be one or more members selected from the group consisting of:

(a) a single repeat MUC1 decoy peptide comprising at least 15 contiguous amino acids of GSTAPPAHGVTSAPDTRPAP (SEQ ID NO:1), (b) a tandem repeat MUC1 decoy peptide comprising at least five MUC1 repeats, wherein each MUC1 repeat comprises at least 15 contiguous amino acids of GSTAPPAHGVTSAPDTRPAP (SEQ ID NO:1) and wherein the sequence of each MUC1 repeat may vary in the peptide, (c) an ectodomain MUC1 decoy peptide comprising the amino acid sequence MTPGTQSPFFLLLLLTVLTVVTGSGHASSTPGGEKETSATQRSSVPSSTEKNAVSMTSSV LSSHSPGSGSSTTQGQDVTLAPATE-PASGSAATWGQDVTSVPVTRPALGSTTPPAHDVTS APDNKPAPXGSTAPPAHG-VTSAPDNRPALGSTAPPVHNVTSASGSASGSAS-TLVHNGTS ARATTTPASKSTPFSIPSHHSDTPTTLASH-STKTDASSTHHSTVPPLTSSNHSTSPQLSTGV SFFFLS-FHISNLQFNSSLEDPSTDYYQELQRDISEMFLQIY-KQGGFLGLSNIKFRPG (SEQ ID NO:2), wherein X̲ is at least five MUC1 repeats, wherein each MUC1 repeat comprises at least 15 contiguous amino acids of GSTAPPAHGVTSAPDTRPAP (SEQ ID NO:1) and wherein the sequence of each MUC1 repeat may vary in the peptide, (d) a sequence variant MUC1 decoy peptide having at least 80% sequence identity to a peptide of (a), (b) or (c), (e) a desialylated version of a peptide of (a), (b), (c) or (d), and (f) a deglycosylated version of a peptide of (a), (b), (c) or (d).

In particular aspects, the ectodomain MUC1 decoy peptides include the decoy peptide set forth in SEQ ID NO:3, desialylated versions thereof, and deglycosylated versions thereof.

The present invention includes pharmaceutical formulations comprising MUC1 decoy peptides and pharmaceutically acceptable carriers or diluents.

Turning back to the second embodiment, the present invention includes methods of treating and/or preventing a bacterial infection in a subject. The methods comprise administering a therapeutically effective amount of one or more MUC1 decoy peptides to a subject in need thereof, such as a subject having a bacterial infection or a subject at risk of developing a bacterial infection. The MUC1 decoy peptides may be in a pharmaceutical formulation comprising the one or more MUC1 decoy peptides and a pharmaceutically acceptable carrier or diluent. In aspects of this embodiment, the MUC1 decoy peptides may be one or more members selected from the group consisting of:

(a) a single repeat MUC1 decoy peptide comprising at least 15 contiguous amino acids of GSTAPPAHGVTSAPDTRPAP (SEQ ID NO:1), (b) a tandem repeat MUC1 decoy peptide comprising at least five MUC1 repeats, wherein each MUC1 repeat comprises at least 15 contiguous amino acids of GSTAPPAH- GVTSAPDTRPAP (SEQ ID NO:1) and wherein the sequence of each MUC1 repeat may vary in the peptide, (c) an ectodomain MUC1 decoy peptide comprising the amino acid sequence MTPGTQSPFFLLLLLTVLTVVTGS-GHASSTPGGEKETSATQRSSVPSSTEKNAVSMTSSV LSSHSPGSGSSTTQGQDVTLAPATE-PASGSAATWGQDVTSVPVTRPALGSTTPPAHDVTS APDNKPAP XGSTAPPAHGVTSAPDNRPALGSTAPPVHNVTSAS-GSASGSASTLVHNGTS ARATTTPASKSTPFSIPSHHS-DTPTTLASHSTKTDASSTHHSTVPPLTSSNHSTSPQL-STGV SFFFLSFHISNLQFNSSLEDPSTDYYQELQRDIS-EMFLQIYKQGGFLGLSNIKFRPG (SEQ ID NO:2), wherein X is at least five MUC1 repeats, wherein each MUC1 repeat comprises at least 15 contiguous amino acids of GSTAPPAHGVTSAPDTRPAP (SEQ ID NO:1) and wherein the sequence of each MUC1 repeat may vary in the peptide, (d) a sequence variant MUC1 decoy peptide having at least 80% sequence identity to a peptide of (a), (b) or (c), (e) a desialylated version of a peptide of (a), (b), (c) or (d), and (f) a deglycosylated version of a peptide of (a), (b), (c) or (d).

In particular aspects, the ectodomain MUC1 decoy peptides include the decoy peptide set forth in SEQ ID NO:3, desialylated versions thereof, and deglycosylated versions thereof. In a specific aspect of this embodiment, the invention is directed to a method of treating a bacterial infection in a subject comprising administering a therapeutically effective amount of one or more MUC1 decoy peptides to a subject in need thereof, wherein the MUC1 decoy peptide is one or more members of the group defined above, i.e. the group of (a) through (f). In another specific aspect of this embodiment, the invention is directed to a method of preventing a bacterial infection in a subject comprising administering a therapeutically effective amount of one or more MUC1 decoy peptides to a subject in need thereof, wherein the MUC1 decoy peptide is one or more members of the group defined above, i.e. the group of (a) through (f). The MUC1 decoy peptides may be in a pharmaceutical formulation comprising the one or more MUC1 decoy peptides and a pharmaceutically acceptable carrier or diluent.

The second embodiment also includes methods of treating and/or preventing a bacterial infection in a subject where another antibacterial agent, such as an antibiotic, is administered to the subject in conjunction with the MUC1 decoy peptides. These methods comprise administering (i) a therapeutically effective amount of one or more MUC1 decoy peptides and (ii) a therapeutically effective amount of one or more antibacterial agents to a subject in need thereof, such as a subject having a bacterial infection or a subject at risk of developing a bacterial infection. The antibacterial agents and the MUC1 decoy peptides may be in pharmaceutical formulations comprising pharmaceutically acceptable carriers or diluents. The formulations may comprise the antibacterial agents and the MUC1 decoy peptides in separate formulations or together in the same formulation.

The MUC1 decoy peptides are one or more members of the group defined above, i.e. the group of (a) through (f). The antibacterial agents include, but are not limited to, antibiotics, antiseptics, disinfectants, bactericidal agents, and bacteriostatic agents. In certain aspects, the antibacterial agents are one or more antibiotics. A suitable antibiotic for use in the methods of the present invention includes, but is not limited to, cefepime.

The antibacterial agents and the MUC1 decoy peptides may be administered to the subject via separate administrations (such as when they are formulated separately) or via the same administration (such as when they are together in the same formulation). When administered via separate administrations, the agents and peptides may be administered in either order, with separate or overlapping periods of administration.

In aspects of this embodiment, the bacterial infection is caused by a bacteria selected from the group consisting of *P. aeruginosa, Helicobacter pylori, Campylobacter jejuni, Escherichia coli, Salmonella enterica, Burkholderia cenocepacia, Burkholderia pseudomallei, Stenotrophomonas maltophilia, Legionella pneumophila, Bordetella bronchiseptica, Enterobacter* spp., *Neisseria gonorrhoeae, Bacillus cereus, Bacillus subtilis, Actinobacillus pleuropneumonias*, and *Yersinia pseudotuberculosis*.

In further aspects of this embodiment, the bacterial infection is an infection selected from the group consisting of pulmonary infections (including infections in the lungs of subjects with cystic fibrosis and ventilator-associated pneumonia), skin infections (including burns, wounds, and infections of surgical sites), blood infections (including sepsis), urinary tract infections, and infections of the eye or ear. The source of the infection may be a hospital-acquired (nosocomial) or community-acquired infection. In a particular aspect, the infection is a *P. aeruginosa* pulmonary infection.

In additional aspects of this embodiment, the MUC1 decoy peptides are formulated in pharmaceutical formulations comprising the peptides and pharmaceutically acceptable carriers or diluents.

Turning back to the third embodiment, the present invention includes methods of determining whether a subject has been colonized by a selected bacteria or whether a subject has an infection of a selected bacteria. In each aspect of this embodiment, the methods comprising screening a biological sample from a subject for shed MUC1 ectodomain, wherein when shed MUC1 ectodomain is detected in the sample, the subject has been colonized by the selected bacteria or the subject has an infection of a selected bacteria.

In aspects of this embodiment, the bacteria is selected from the group consisting of *P. aeruginosa, Helicobacter pylori, Campylobacter jejuni, Escherichia coli, Salmonella enterica, Burkholderia cenocepacia, Burkholderia pseudomallei, Stenotrophomonas maltophilia, Legionella pneumophila, Bordetella bronchiseptica, Enterobacter* spp., *Neisseria gonorrhoeae, Bacillus cereus, Bacillus subtilis, Actinobacillus pleuropneumonias*, and *Yersinia pseudotuberculosis*.

In further aspects of this embodiment, the biological sample is bronchoalveolar lavage fluid (BALF), protected specimen brush (PSB) bronchial sample, endotracheal aspiration, or swabbing from an infected or potentially infected area.

In additional aspects of this embodiment, the screening is a method selected from the group consisting of enzyme-linked immunosorbent assay (ELISA), lateral flow immunoassay, magnetic immunoassay, radioimmunoassay, fluorescent immunosassay, Western immunoblot assay, dot immunoblot assay, and slot immunoblot assay.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

FIG. 1. MUC1 Proteins. FIG. 1A shows full-length, membrane MUC1, with the extracellular ectodomain denoted. Also shown is the sequence of the 20-amino acid repeat (SEQ ID NO:1) and the Gly-Ser cleavage site that releases the ectodomain from the cell surface. FIG. 1B exhibits the steps in bacterial binding to MUC1 and shedding of the ectodomain of the protein. Upon initial contact between a bacterium and MUC1 (Step 1), flagellin stimulates NEU1 recruitment to MUC1 (Step 2), increases NEU1-mediated desialylation of MUC1-ED (Step 3), and enhances bacterial adhesion and invasion. Flagellin also provokes release of bacteria-bound MUC1-ED from the cell surface (Steps 4 and 5).

FIG. 2. Amino acid Sequence of the MUC1 Protein. The complete amino acid sequence of a MUC1 (SEQ ID NO:4). Regions underlined with a straight line correspond to non-repeat regions in the ectodomain. Wavy underline region corresponds to the portion of the protein that remains in the cell membrane after the ectodomain is shed. NCBI accession number P15941.3.

(FIG. 3A) A549 lung carcinoma cells were infected with adenovirus encoding FLAG-tagged NEU1 (Ad-NEU1-FLAG) or adenovirus encoding hemagglutinin-tagged NEU3 (Ad-NEU3-HA) at the indicated multiplicities of infection (MOIs), cultured for 48 h, and lysed. The lysates were processed for FLAG (NEU1) or HA (NEU3) immunoblotting. (FIG. 3B) A549 cells and A549 cells infected with adenovirus encoding green fluorescent protein (Ad-GFP), Ad-NEU1-FLAG, or Ad-NEU3-HA (MOI=100) were cultured for 48 h, fixed, washed, and incubated for 30 min with each of the indicated bacteria (MOI=100). Nonadherent bacteria were removed by washing, and colony forming units (CFUs) bond to the ECs quantified. (FIG. 3C) A549 cells were transfected with MUC1-targeting or control small interfering (si)RNAs, cultured for 48 h, and lysed. The lysates were processed for MUC1-ED immunoblotting. (FIG. 3D) A549 cells and A549 cells infected with Ad-GFP or Ad-NEU1 (MOI=100) were cultured for 24 h. The ECs were transfected with MUC1-targeting or control siRNAs and cultured for an additional 48 h. Adhesion of Pa and *Legionella pneumophila* to the ECs was assayed. (FIG. 3E) Pa adhesion to small airway epithelial cells (SAECs) infected for 48 h with Ad-GFP or Ad-NEU1 (MOI=100) was determined. (FIG. 3F) A549 cells infected with increasing MOI's of Ad-NEU1-G68V were cultured for 48 h, lysed, and the lysates processed for NEU1 immunoblotting. (FIG. 3G) Pa adhesion to A549 cells infected for 48 h with increasing MOIs of Ad-NEU1 wild type (WT) or Ad-NEU1-G68V was assayed. (FIG. 3H) A549 cells were infected with Ad-NEU1-FLAG (MOI=100) and cultured for 24 h. The ECs were transfected with NEU1-targeting or control siRNAs, cultured for an additional 48 h, lysed, and the lysates processed for FLAG (NEU1) immunoblotting. (FIG. 3I) A549 cells were transfected with NEU1-targeting or control siRNAs, or infected with Ad-NEU1, adenovirus encoding a catalytically-dead NEU1 mutant (Ad-NEU1-G68V), or Ad-GFP (MOI=100), and cultured for 48 h. The ECs were incubated for 1 h with Pa (MOI=100), washed, incubated for 1 h with 200 μg/ml of gentamicin, lysed, and CFUs quantified. (FIG. 3J) A549 cells infected with Ad-GFP or Ad-NEU1 (MOI=100) were cultured for 24 h and transfected with MUC1-targeting or control siRNAs. After 48 h, Pa invasion was quantified. In (FIG. 3A), (FIG. 3C), (FIG. 3F), and (FIG. 3H), to control for protein loading and transfer, blots were stripped and reprobed for β-tubulin. IB, immunoblot. IB*, immunoblot after stripping. Molecular weight (MW) in kiloDaltons (kDa) is indicated on the left. Each blot is representative of 3 independent experiments. In (FIG. 3B), (FIG. 3D), (FIG. 3E), (FIG. 3G), (FIG. 3I) and (FIG. 3J), vertical bars represent mean±SEM CFUs/well (n=4). *, increased bacterial adhesion to or invasion of Ad-NEU1-infected ECs compared with Ad-GFP, Ad-NEU3, or Ad-NEU1-G68V at $p<0.05$. **, decreased Pa adhesion to or invasion of MUC1 siRNA-transfected ECs compared with control siRNA-transfected ECs at $p<0.05$. n.s., not significant.

(FIG. 4A) A549 cells were infected with Ad-GFP or Ad-NEU1 (MOI=100), cultured for 48 h, and adhesion of Pa wild type (WT) or the flagellin-deficient isogenic mutant strain, Pa fliC⁻, quantified. (FIG. 4B) Human embryonic kidney 293T (HEK293T) cells transfected with plasmids encoding for MUC1, Toll-like receptor 5 (TLR5), or the pcDNA empty vector control, were cultured for 48 h and lysed. Lysates were processed for MUC1-ED (upper panel) or TLR5 (middle panel) immunoblotting. (FIG. 4C) HEK293T cells transfected with plasmids encoding for MUC1 or TLR5, or the empty vector control, were cultured for 24 h, and infected with Ad-GFP or Ad-NEU1 (MOI=100). After 48 h, Pa WT adhesion was quantified. (FIG. 4D) A549 cells were infected with Ad-GFP or Ad-NEU1 (MOI=100), cultured for 48 h, and invasion of Pa WT or Pa fliC⁻ quantified. In (FIG. 4A), (FIG. 4C), and (FIG. 4D), vertical bars represent mean±SEM CFUs/well (n=4). *, increased Pa WT adhesion to or invasion of Ad-NEU1-infected ECs compared with Ad-GFP-infected controls at $p<0.05$. **, decreased adhesion or invasion of Pa fliC⁻ compared with Pa WT at $p<0.05$. (FIG. 4E) Coomassie blue-stained sodium dodecyl sulfate-polyacrylamide gel electrophoresis (SDS-PAGE) gel of purified Pa flagellin. (FIG. 4F) A549 cells were preincubated for 30 min with 5.0 μM U0126 or medium alone, washed, incubated for 30 min with 10 mg/ml of Pa flagellin or medium alone, lysed, and the lysates processed for phospho-extracellular signal-regulated kinase 1/2 (ERK1/2) immunoblotting. To control for protein loading and transfer, the blots were stripped and reprobed for total ERK2. (FIG. 4G) A549 cells were incubated for κ h with 10 ng/ml of flagellin or medium alone and culture supernates processed for interleukin-8 (IL-8) ELISA. Vertical bars represent mean±SEM IL-8 ng/ml (n=3). *, increased IL-8 concentrations compared with simultaneous medium control at $p<0.05$. (FIG. 4H) A549 cells were infected with Ad-GFP or Ad-NEU1 (MOI=100), cultured for 48 h, and binding of increasing concentrations of Alexa Fluor 594-flagellin was determined. Data points represent mean±SEM bound flagellin (n=3). (FIG. 4I) Scatchard transformation of the binding data in (FIG. 4H). The equation and $R^2$ value are indicated adjacent to each line. Extrapolation to the x-axis intercepts are indicated by broken lines. The results are representative of 3 independent experiments.

(FIG. 5A) A549 cells infected with Ad-NEU1-FLAG (MOI=100) were cultured for 48 h, incubated for 30 min with Pa WT or Pa fliC$^-$ bacteria (MOI=100), or medium alone, and lysed. The lysates were immunoprecipitated with anti-MUC1-cytoplasmic domain (CD) antibody and the immunoprecipitates processed for FLAG (NEU1) immunoblotting (upper panel). The blots were stripped and reprobed for protective protein/cathepsin A (PPCA) (middle panel) or MUC1-CD (lower panel). (FIG. 5B) Densitometric analyses of the blots in (FIG. 5A). (FIG. 5C) A549 cells and (FIG. 5E) SAECs infected with Ad-NEU1-FLAG (MOI=100) were cultured for 48 h, incubated for the indicated times with 10 ng/ml of Pa flagellin or medium alone, and lysed. The lysates were immunoprecipitated with anti-MUC1-CD antibody and the immunoprecipitates processed for FLAG (NEU1) immunoblotting (upper panel). The blots were stripped and reprobed for PPCA (middle panel) followed by MUC1-CD (lower panel). (FIG. 5D, FIG. 5F) Densitometric analyses of the blots in (FIG. 5C) and (FIG. 5E), respectively. *, increased normalized FLAG (NEU1)/PPCA signal of Pa WT-stimulated ECs compared with Pa fliC$^-$, or flagellin-stimulated ECs compared with medium controls, at $p<0.05$. (FIG. 5G) A549 cells infected with Ad-NEU1-FLAG (MOI=100) were incubated for 30 min with 5.0 µM of U0126 or medium alone, washed, incubated for 30 min with 10 ng/ml of Pa flagellin or medium alone, and lysed. The lysates were immunoprecipitated with anti-MUC1-CD antibody and the immunoprecipitates processed for FLAG (NEU1) immunoblotting. In (FIG. 5A), (FIG. 5C), (FIG. 5E), and (FIG. 5G), to control for loading and transfer, blots were stripped and reprobed for MUC1-CD. IP, immunoprecipitation. IB, immunoblot. IB*, immunoblot after stripping. MW in kDa is indicated on the left. Each blot is representative of 3 independent experiments. In (FIG. 5B), (FIG. 5D), and (FIG. 5F), vertical bars represent mean±SEM FLAG (NEU1) or PPCA signal normalized to MUC1-CD signal in the same lane on the same stripped and reprobed blot (n=3).

(FIG. 6A) Fetuin and asialofetuin (1.0 µg) were processed for *Maackia amurensis* lectin II (MAL), *Sambucus nigra* agglutinin (SNA), and peanut agglutinin (PNA) lectin blotting as controls to validate lectin specificity. (FIG. 6B) A549 cells infected with Ad-GFP, Ad-NEU1, or Ad-NEU1-G68V (MOI=100) were cultured for 48 h and lysed. The lysates were immunoprecipitated with anti-MUC1-ED antibody and the immunoprecipitates processed for MAL (lanes 1-3), SNA (lanes 4-6), or PNA (lanes 7-9) lectin blotting. To control for protein loading and transfer, blots were stripped and reprobed for MUC1-ED. (FIG. 6C) Densitometric analyses of the blots in (FIG. 6B). Vertical bars represent mean±SEM lectin signal normalized to MUC1-ED signal in the same lane in the same stripped and reprobed blot (n=3). *, increased normalized PNA signal of Ad-NEU1-infected ECs compared with Ad-GFP or Ad-NEU1-G68V at $p<0.05$. **, decreased normalized MAL/SNA signal of Ad-NEU1-infected ECs compared with Ad-GFP or Ad-NEU1-G68V-infected at $p<0.05$. (FIG. 6D) A549 cells were incubated for the indicated times with 10 ng/ml of Pa flagellin or medium alone and lysed. The lysates were incubated with PNA immobilized on Sepharose beads and the PNA-binding proteins processed for MUC1-ED immunoblotting. (FIG. 6E) Densitometric analyses of the blots in (FIG. 6D). (FIG. 6F, FIG. 6H) A549 cells (FIG. 6F) and SAECs (FIG. 6H) transfected with NEU1-targeting or control siRNAs were cultured for 48 h, incubated for 60 min with 10 ng/ml of Pa flagellin or medium alone and lysed. The lysates were incubated with PNA-Sepharose and the PNA-binding proteins processed for MUC1-ED immunoblotting. (FIG. 6G, FIG. 6I) Densitometric analysis of the blots in (FIG. 6F) and (FIG. 6H), respectively. PD, PNA pull down. In (FIG. 6E), (FIG. 6G), and (FIG. 6I), vertical bars represent mean±SEM MUC1-ED signal (n=3). increased MUC1-ED signal of flagellin-stimulated ECs compared with the medium control at $p<0.05$. if, decreased MUC1-ED signal of NEU1 siRNA-transfected ECs compared with control siRNA-transfected ECs at $p<0.05$. The results are representative of 3 independent experiments.

(FIG. 7A) A549 cells were incubated for increasing times with 10 ng/ml of Pa flagellin or medium alone, washed, and Pa adhesion quantified. (FIG. 7B) A549 cells were incubated for 90 min with medium alone (panel i) or 10 ng/ml of Pa flagellin (panel ii). The ECs were washed, incubated for 40 min with GFP-Pa (MOI=100), washed, counterstained with 4',6-diamidino-2-phenylindole (DAPI), and processed for fluorescence microscopy. (FIG. 7C) A549 cells transfected with NEU1-targeting or control siRNAs were cultured for 48 h, incubated for 90 min with 10 ng/ml of Pa flagellin or medium alone, and Pa adhesion quantified. (FIG. 7D) A549 cells transfected with NEU1-targeting or control siRNAs were cultured for 48 h and incubated for 90 min with medium alone (panel i) or 10 ng/ml of Pa flagellin (panel ii). The ECs were incubated with GFP-Pa, washed, counterstained with DAPI, and processed for fluorescence microscopy. (FIG. 7E) SAECs transfected with NEU1-targeting or control siRNAs were cultured for 48 h, incubated for 90 min with 10 ng/ml of Pa flagellin or medium alone, and Pa adhesion quantified. (FIG. 7F) A549 cells transfected with NEU1-targeting or control siRNAs were cultured for 48 h, incubated for 60 min with 10 ng/ml of Pa flagellin or medium alone, and Pa invasion quantified. In (FIG. 7A), (FIG. 7C), (FIG. 7E), and (FIG. 7F), vertical bars represent mean±SEM CFUs/well (n=4). *, increased Pa adhesion to or invasion of flagellin-stimulated ECs compared with the medium controls at $p<0.05$. **, decreased Pa adhesion to or invasion of NEU1-targeting siRNA-transfected ECs compared with control siRNA-transfected ECs at $p<0.05$. In (FIG. 7B) and (FIG. 7D), scale bars=25 µm. The results are representative of 3 independent experiments.

(FIG. 8A) A549 cells were infected with increasing MOIs of Ad-GFP or Ad-NEU and incubated for 24-48 h. MUC1-ED levels in EC culture supernates were quantified by ELISA and normalized to total EC protein. (FIG. 8B) Culture supernates (100 µl) were incubated with PNA-Sepharose and the PNA-binding proteins processed for MUC1-ED immunoblotting. (FIG. 8C) Densitometric analyses of the blots in (FIG. 8B). (FIG. 8D-FIG. 8G) A549 cells (FIG. 8D, FIG. 8F, FIG. 8G) and SAECs (FIG. 8E) were transfected with NEU1-targeting or control siRNAs and cultured for 24 h. The ECs were incubated for 30 min with increasing concentrations of Pa flagellin, or medium alone, washed, and incubated for 24 h. (FIG. 8D, FIG. 8E) Culture supernates were processed for MUC1-ED ELISA. (FIG. 8F) Supernates (100 µl) from flagellin-stimulated A549 cells were incubated with PNA-Sepharose and the PNA-binding proteins processed for MUC1-ED immunoblotting. (FIG. 8G) Densitometric analyses of the blots in (FIG. 8F). In (FIG. 8A), (FIG. 8D) and (FIG. 8E), vertical bars represents mean±SEM MUC1-ED levels normalized to total EC protein (n=9). In (FIG. 8C) and (FIG. 8G), vertical bars represents mean±SEM MUC1-ED signal (n=3). *, increased MUC1-ED level or signal in supernates from Ad-NEU1-infected ECs compared with Ad-GFP, or flagellin-stimulated ECs compared with medium control, at p<0.05, **, decreased MUC1-ED level or signal in supernates from NEU1 siRNA-compared with control siRNA-transfected ECs at p<0.05. (FIG. 8H, FIG. 8I) MUC1-ED levels in BALFs from noncolonized patients, Pa-colonized patients, or patients colonized with nonPa microorganisms were quantified by ELISA and normalized to total BALF protein. *, increased mean MUC1-ED levels in BALFs from Pa-colonized patients compared with levels in BALFs from noncolonized patients or patients colonized with nonPa microbes at p<0.05. (FIG. 8J) Equal protein aliquots (100 µg) of BALFs from noncolonized patients, Pa-colonized patients, or patients colonized with nonPa microorganisms were incubated with PNA-Sepharose and the PNA-binding proteins processed for MUC1-ED immunoblotting. (FIG. 8K) Densitometric analyses of the blots in (FIG. 8J). Vertical bars represents mean±SEM MUC1-ED signal. The n for each condition is indicated. *, increased MUC1-ED signal in BALFs from Pa-colonized patients compared with noncolonized patients or patients colonized with nonPa microorganisms at p<0.05. The results are representative of ≥2 independent experiments.

(FIG. 9A) A549 cells were infected with Ad-GFP or Ad-NEU1 (MOI=250), cultured for 24 h, and EC culture supernates were collected. Pa were preincubated for 30 min with equivalent volumes of supernates from Ad-NEU1- or Ad-GFP-infected ECs containing the indicated concentrations of MUC1-ED, and assayed for adhesion to fresh A549 cell monolayers. (FIG. 9B) A549 cells were transfected with NEU1-targeting or control siRNAs and incubated for 24 h. The ECs were incubated for 30 min with 30 ng/ml of Pa flagellin, cultured for 24 h, and EC culture supernates collected. Pa were preincubated for 30 min with equivalent volumes of EC culture supernates from NEU1-targeting or control siRNA-transfected ECs containing the indicated concentrations of MUC1-ED, and assayed for adhesion to fresh A549 cell monolayers. **, decreased Pa adhesion following preincubation with supernates from Ad-NEU1-compared with Ad-GFP-infected ECs, or control siRNA-compared with NEU1-targeting siRNA-transfected ECs, at p<0.05. (FIG. 9C) Supernates of A549 cells infected with Ad-NEU1 or stimulated by flagellin, each containing 2.5 µg/ml of MUC1-ED, were incubated with 100 µg/ml of anti-MUC1-ED antibody or a nonimmune IgG control. Immunoglobulins (Igs) were immobilized on protein G-agarose, removed by centrifugation, and the remaining supernates were processed for MUC1-ED immunoblotting. (FIG. 9D) Pa were incubated for 30 min with the supernates in (FIG. 9C), or supernates of A549 cells transfected with MUC1-targeting or control siRNAs, and assayed for adhesion to A549 cells. *, increased Pa adhesion following MUC1-ED immnodepletion compared with preincubation with IgG control, or MUC1-targeting siRNA-compared with control siRNA-transfected ECs, at p<0.05. (FIG. 9E) Supernates of A549 cells infected with Ad-NEU1 or stimulated by flagellin were incubated with the IgG control (panels i, ii) or immunodepleted with anti-MUC1-ED antibody (panels iii-iv). Igs were immobilized on protein G-agarose and removed by centrifugation. GFP-Pa were incubated for 30 min with the supernates, washed, and incubated with A549 cells. The ECs were washed, counterstained with DAPI, and processed for fluorescence microscopy. (FIG. 9F) The indicated bacteria were incubated for 30 min with BALFs from Pa-colonized patients containing 2.5 µg/ml of MUC1-ED, or BALFs from noncolonized patients or patients colonized with nonPa microorganisms containing an equivalent amount of BALF total protein. The bacteria were washed and assayed for adhesion to A549 cells. **, decreased bacterial adhesion following preincubation with BALF from Pa-colonized patients compared with noncolonized patients or patients colonized with nonPa microbes at p<0.05. (FIG. 9G) BALFs from Pa-colonized patients were incubated with anti-MUC1-ED antibody, or a nonimmune IgG control. Igs were immobilized on protein G-agarose and removed by centrifugation, and the remaining BALFs were processed for MUC1-ED immunoblotting. (FIG. 9H) Pa were incubated for 30 min with the BALFs in (FIG. 9G) and assayed for adhesion to A549 cells. *, increased Pa adhesion following MUC1 immunodepletion compared with preincubation with IgG control. In (FIG. 9A), (FIG. 9B), (FIG. 9D), (FIG. 9F), and (FIG. 9H), each bar represents mean±SEM bacterial adhesion (n=6). The results are representative of ≥2 independent experiments. (FIG. 9I) BALFs from Pa-colonized patients were incubated with the IgG control (panels i-iv) or immune-depleted anti-MUC1-ED antibody (panels v-viii). Igs were immobilized on protein G-agarose and removed by centrifugation. GFP-Pa were preincubated for 30 min with the BALFs, washed, and incubated with A549 cells. The ECs were washed, counterstained with DAPI, and processed for fluorescence microscopy. In (FIG. 9E) and (FIG. 9I), scale bar=25 µm.

(FIG. 13A-FIG. 13D) Mice were challenged intratracheally (i.t.) with PBS or $10^5$ CFU/mouse of Pa. (FIG. 13A, FIG. 13B) BALF and (FIG. 13C, FIG. 13D) lungs were collected at 48 h (FIG. 13A, FIG. 13C) and 72 h (FIG. 13B, FIG. 13D) post-challenge and Pa CFUs were quantified. Vertical bars represents mean±SEM CFU/ml (FIG. 13A, FIG. 13B) or CFU/g (FIG. 13C, FIG. 13D) (n=3). **, decreased Pa CFUs vs. PBS controls at p<0.05. Data points represent mean±SEM $A_{600}$ values (n=3). The results are representative of >2 independent experiments.

DETAILED DESCRIPTION OF THE INVENTION

I. Definitions

Figure 3:
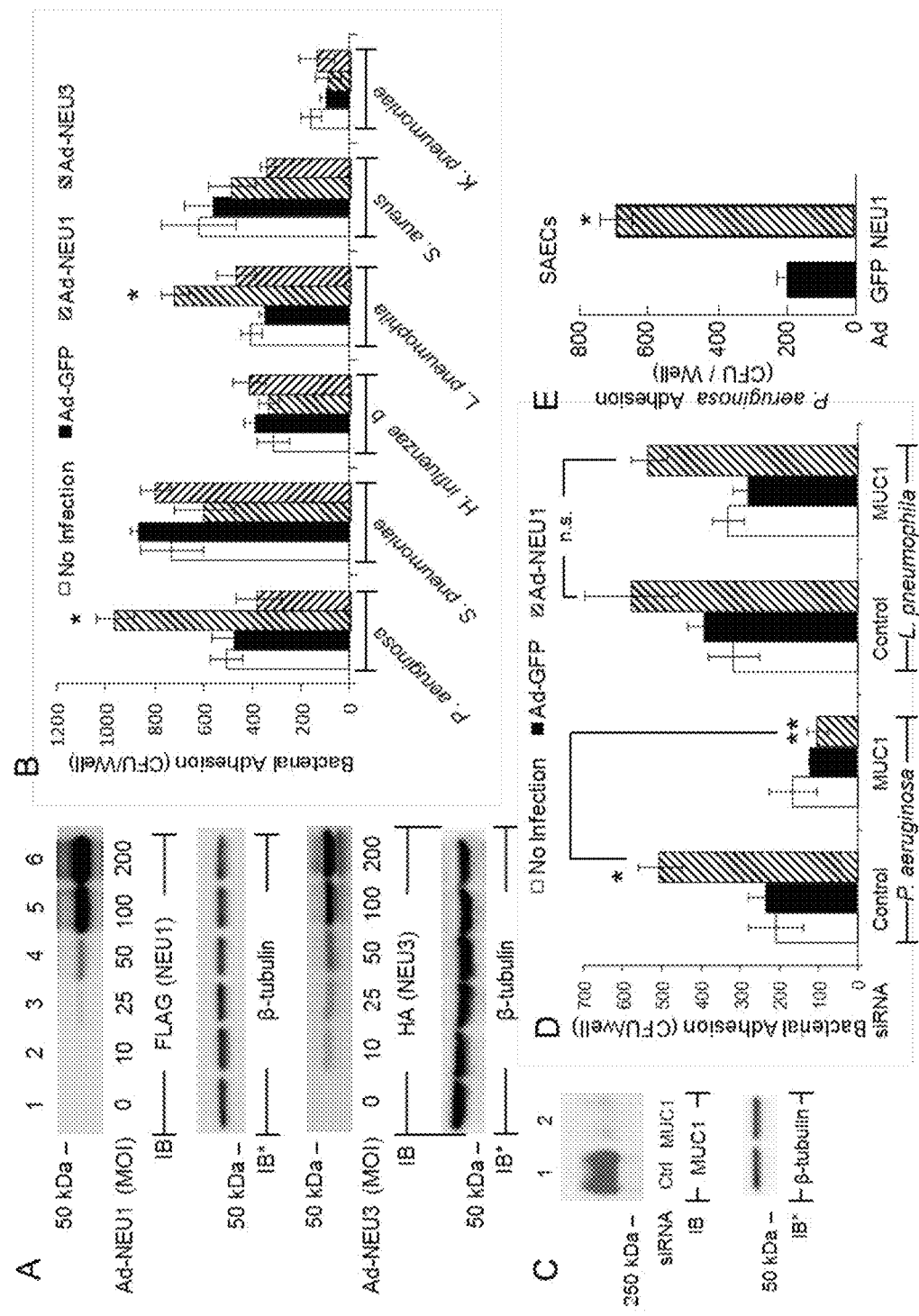
FIG. 3. NEU1 Overexpression Selectively Enhances MUC1-Dependent *P. aeruginosa* (Pa) Adhesion to and Invasion of Airway ECs.
Figure 3:
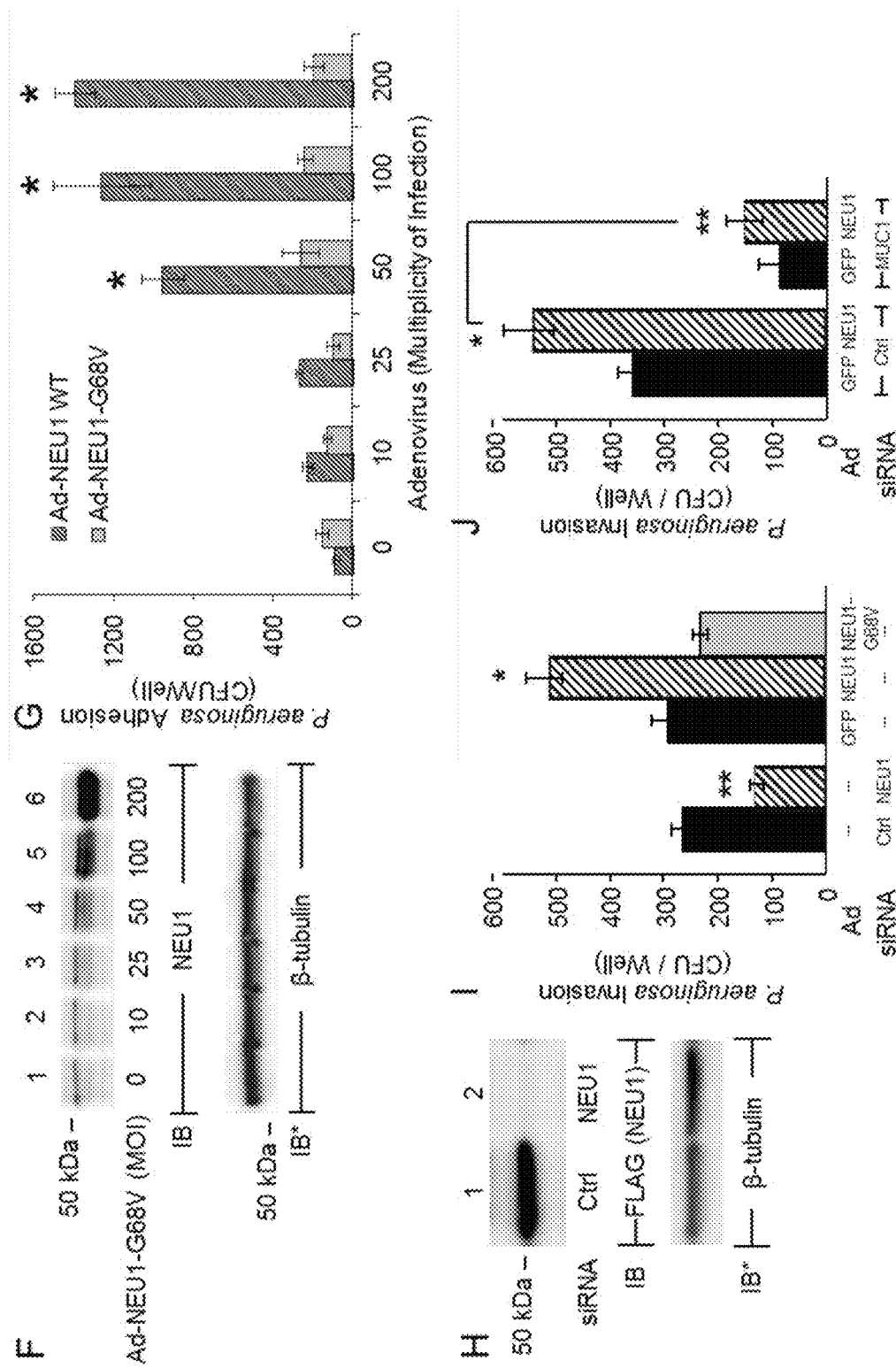

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g. ±5-10% of the recited value) that one of ordinary skill in the art would consider equivalent to the recited value (e.g., having the same function or result). In some instances, the term "about" may include numerical values that are rounded to the nearest significant figure.

II. The Present Invention

Bacterial adhesion to airway epithelial cells (ECs) is prerequisite to establishment of infection and is mediated through interactions between microbial adhesins and their cognate host cell receptors (Prince, 1992). One such *P. aeruginosa* adhesin, flagellin, is the structural protein that forms the major portion of the flagellar filament. Flagellin contributes to the virulence of pathogenic bacteria through motility, thereby promoting adhesion and invasion (Ramos et al., 2004). *P. aeruginosa* flagellin engages the transmembrane polypeptide mucin-1, MUC1, expressed by ECs. This interaction is coupled to intracellular signaling (Lillehoj et al., 2012).

MUC1 is a membrane-spanning protein that encompasses a variable number of highly sialylated tandem amino acid sequence repeats in the extracellular domain (ectodomain, termed MUC1-ED) of the protein. The number of repeats in human MUC1 generally ranges between 20 and 120 copies. Given that the number of repeats can vary between individuals, one specific sequence cannot define the protein. However, the amino acid sequence set forth in SEQ ID NO:4 provides an example of the sequence, where the invariant N-terminus encompasses amino acids 1-128, the repeat regions encompasses amino acids 129-1018, and the C-terminus encompasses amino acids 1019-1255. The protein is also shown in FIG. 1A, where the Gly-Ser cleavage site, located 58-amino acids upstream of the transmembrane domain within the proximal, extracellular, juxtamembranous region, is illustrated. Enzyme cleavage here releases MUC1-ED, allowing the ~250 kDa ectodomain to be shed from the cell surface (Lillehoj et al., 2013). Three MUC1-ED sheddases have been identified, matrix metalloproteinase (MMP)14, a disintigrin and metalloproteinase (ADAM) 17, and γ-secretase (Lillehoj et al., 2013). The 20 amino acid repeat sequence (GSTAPPAHGVTSAPDTRPAP; SEQ ID NO:1) is also shown in FIG. 1A. Ser and Thr residues serve as sites of O-linked glycosylation and Pro residues impart an extended, rod-like configuration on the MUC1-ED that enables it to extend far into the lumen of the airways where it is strategically positioned to interact with potential bacterial pathogens, such as *P. aeruginosa* (Lillehoj et al., 2013).

Glycoprotein receptors for bacteria often contain glycan chains terminating with sialic acid (SA). SA residues are strategically positioned to influence cell-cell and intermolecular interactions (Schauer, 2009). SA residues can mask binding sites for pathogens, their toxins, endogenous lectins, and protease recognition sites through protein conformational changes, electrostatic repulsion, and/or steric hindrance (Lewis and Lewis, 2012). The sialylation state of glycoconjugates is dynamically and coordinately regulated through the opposing catalytic activities of sialyltransferases and sialidases/neuraminidases (NEUs). NEUs constitute a large family of prokaryotic and eukaryotic glycolytic enzymes that hydrolyze the linkages between SA and its flanking sugars (Pshezhetsky and Ashmarina, 2013).

Prokaryotic NEUs are established virulence factors for viral and bacterial pathogens (Lewis and Lewis, 2012). *P. aeruginosa* NEU, NanPs, contributes to bacterial pathogenesis and its expression is linked to biofilm formation and airway colonization (Soong et al., 2006). Although much is known about prokaryotic NEUs as virulence factors, a role for mammalian host NEUs in bacterial pathogenesis has never been considered. Of the four known mammalian NEUs, NEU1 is the predominant sialidase expressed by human airway ECs, while the second most abundant, NEU3, is expressed at much lower levels (Lillehoj et al., 2012). NEU1 is localized both to lysosomes and the cell surface (Pshezhetsky and Ashmarina, 2013) and is only active in association with its chaperone/transport protein, protective protein/cathepsin A (PPCA) (Bonten and d'Azzo, 2000).

It was previously established that forced NEU1 overexpression increases MUC1-ED desialylation and MUC1-ED-dependent *P. aeruginosa* adhesion to airway ECs (Lillehoj et al., 2012). To extend these findings to a physiologically relevant context, the present inventors asked whether the MUC1-ED ligand, i.e., *P. aeruginosa* flagellin, promotes NEU1-mediated MUC1-ED desialylation and MUC1-ED-dependent *P. aeruginosa* adhesion to and invasion of airway ECs. The results from the experiments disclosed herein demonstrate for the first time that a bacterial pathogen, *P. aeruginosa*, exploits the human sialidase, NEU1, to amplify its own pathogenicity. Upon initial contact between *P. aeruginosa* and MUC1-expressing ECs (Step 1 of FIG. 1B), flagellin stimulates NEU1 recruitment to MUC1 (Step 2 of FIG. 1B), increases NEU1-mediated desialylation of MUC1-ED (Step 3 of FIG. 1B), and enhances *P. aeruginosa* adhesion and invasion. In particular, the results presented herein demonstrate that NEU1 increases the binding affinity of purified flagellin to airway ECs 3-fold.

Surprisingly, and as also disclosed herein, it has been found that simultaneous with bacterial hijacking of host NEU1, flagellin provokes release of *P. aeruginosa*-bound MUC1-ED from the EC surface (Steps 4 and 5 of FIG. 1B). In addition, unbound MUC1-ED is also released from the cell surface which can competitively block *P. aeruginosa* adhesion to EC-associated MUC1-ED. These results indicate that while *P. aeruginosa* commandeers host NEU1 sialidase to enhance its pathogenicity, the host retaliates by releasing MUC1-ED as a hyperadhesive decoy receptor. An embodiment of the present invention is based on these important findings. As summarized above, the present invention includes methods of treating and/or preventing bacterial infections in a subject through the administration of a therapeutically effective amount of a MUC1 decoy peptide to a subject in need thereof, such as a subject having a bacterial infection or a subject at risk of developing a bacterial infection. These MUC1 decoy peptides are defined herein. Such methods can also be practiced by administering one or more other antibacterial agents, such as antibiotics, to the subject in conjunction with the MUC1 decoy peptides.

In additional research discussed below, it was discovered that the levels of desialylated MUC1-ED are elevated in the bronchoalveolar lavage fluid (BALF) harvested from patients with *P. aeruginosa* airway colonization, and these MUC1-ED-containing samples dose-dependently block *P. aeruginosa* adhesion to airway ECs. Another embodiment of the invention is based on these additional findings, namely methods of determining whether a subject has been colonized by a selected bacteria or whether a subject has an infection of a selected bacteria by screening a biological sample, such as BALF, for the presence of MUC1-ED.

As also summarized above, the present invention includes human MUC1 decoy peptides, and pharmaceutical formulations comprising MUC1 decoy peptides and pharmaceutically acceptable carriers or diluents.

MUC1 Decoy Peptides

The MUC1 decoy peptides of the present invention are glycosylated or unglycosylated peptides of varying lengths that each comprises one or more, full or partial amino acid repeats from the tandem repeat region of the MUC1 ectodomain (MUC1-ED).

The tandem repeat region of MUC1-ED consists of a series of 20-amino acid repeating sub-regions, linked in a head-to-tail fashion in the MUC1-ED. In endogenously-produced MUC1, each tandem repeat is modified by the addition of sialic acid (SA)-containing carbohydrate side chains. Removal of SA by NEU1-mediated enzymatic desialylation has two effects, (1) increased binding of *P. aeruginosa* to MUC1, and (2) increased shedding of MUC1-ED from the EC surface into the extracellular fluid. Data presented herein indicates that desialylated MUC1-ED protein that is shed in the culture fluids of NEU1-engineered lung epithelial cells acts as a decoy to inhibit *P. aeruginosa* attachment to MUC1-ED that remains cell-associated. Because removal of SA alone, or the entire carbohydrate side chains, from MUC1-ED enhanced its ability to block bacterial attachment to the lung cells, it is hypothesized that the protein backbone of MUC1-ED is responsible for its inhibitory activity.

More particularly, the MUC1 decoy peptides of the invention include peptides comprising a single MUC1 repeat, where the MUC1 repeat comprises at least 15 contiguous amino acids of the 20-amino acid ectodomain repeat GSTAPPAHGVTSAPDTRPAP (SEQ ID NO:1), derived from either end or the internal region of the full length repeat sequence. Such peptides are termed "single repeat MUC1 decoy peptides" herein. Thus, in one aspect the invention is directed to single repeat MUC1 decoy peptides comprising at least 15 contiguous amino acids of GSTAPPAHGVTSAPDTRPAP (SEQ ID NO:1).

The MUC1 decoy peptides also include peptides comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130 or more MUC1 repeats, where each MUC1 repeat comprises at least 15 contiguous amino acids of GSTAPPAHGVTSAPDTRPAP (SEQ ID NO:1) and wherein the sequence of each MUC1 repeat may vary in the peptide. The MUC1 repeats are linked head-to-tail to form a contiguous amino acid sequence. Such peptides are termed "tandem repeat MUC1 decoy peptides" herein. Thus, in another aspect the invention is directed to tandem repeat MUC1 decoy peptides comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130 or more MUC1 repeats. The sequences of the MUC1 repeats may vary, that is, the sequence of the MUC1 repeats comprising a tandem repeat MUC1 decoy peptide can be the same or different, or a combination thereof (e.g., in a peptide with 10 MUC1 repeats, five could have the same sequence and the other five could each have a unique sequence, for example).

As indicated above, the MUC1 decoy peptides may be limited in sequence to one or more MUC1 repeats and variants thereof. In addition, the MUC1 decoy peptides may comprise all or a portion of the amino acid sequences of the non-repeat regions in the ectodomain that are present in the endogenous protein, i.e., those sequence on either side of the repeat region. These non-repeat regions are underlined with a straight line in the MUC1 amino acid sequence shown in FIG. 2. The wavy underline corresponds to the portion of the protein that remains in the cell membrane after the ectodomain is shed. These MUC1 decoy peptides are termed "ectodomain MUC1 decoy peptides" herein and they comprise at least 20 contiguous amino acids of the non-repeat region N-terminal to the repeat region, i.e., MTPGTQSPFFLLLLLTVLTVVTGSGHASSTPGGEKETSATQRSSVPSSTEKNAVSMTSSV LSSHSPGSGSSTTQGQDVTLAPATEPASGSAATWGQDVTSVPVTRPALGSTTPPAHDVTS APDNKPAP (SEQ ID NO:5), at least 20 contiguous amino acids of the non-repeat region C-terminal to the repeat region, i.e., GSTAPPAHGVTSAPDNRPALGSTAPPVHNVTSASGSASGSASTLVHNGTSARATTTPAS KSTPFSIPSHHSDTPTTLASHSTKTDASSTHHSTVPPLTSSNHSTSPQLSTGVSFFFLSFHIS NLQFNSSLEDPSTDYYQELQRDISEMFLQIYKQGGFLGLSNIKFRPG (SEQ ID NO:6), and they are linked by at least one MUC1 repeat as defined above (i.e., comprising at least 15 contiguous amino acids of GSTAPPAHGVTSAPDTRPAP (SEQ ID NO:1)). The sequence of the MUC1 repeats may be the same or different, or a combination thereof (e.g., in a peptide with 10 MUC1 repeats, five could have the same sequence and the other five could each have a unique sequence, for example).

In particular embodiments, the number of MUC1 repeats linking the N-terminal and C-terminal sequences is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130 or more MUC1 repeats.

A non-limiting example of an ectodomain MUC1 decoy peptide is as follows: MTPGTQSPFFLLLLLTVLTVVTGSGHASSTPGGEKETSATQRSSVPSSTEKNAVSMTSSV LSSHSPGSGSSTTQGQDVTLAPATEPASGSAATWGQDVTSVPVTRPALGSTTPPAHDVTS APDNKPAP XGSTAPPAHGVTSAPDNRPALGSTAPPVHNVTSASGSASGSASTLVHNGTS ARATTTPASKSTPFSIPSHHSDTPTTLASHSTKTDASSTHHSTVPPLTSSNHSTSPQLSTGV SFFFLSFHISNLQFNSSLEDPSTDYYQELQRDISEMFLQIYKQGGFLGLSNIKFRPG (SEQ ID NO:2), wherein X is at least one MUC1 repeat. As above, X may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130 or more MUC1 repeats, wherein the sequences of the MUC1 repeats may be the same or different, or a combination thereof (e.g., in a peptide with 10 MUC1 repeats, five could have the same sequence and the other five could each have a unique sequence, for example).

Linkers and Spacers

The tandem repeat MUC1 decoy peptides of the invention may include a short linker or spacer between the MUC1 repeats. Such linkers and spacers may be desirable to enhance formation of a proper three-dimensional structure or shape. The tandem repeat MUC1 decoy peptides may thus have short peptide linkers or spacers of up to 1, 2, 3, 4, 5, 6, 7, 8, 9, 10, 11, 12, 13, 14, 15, 16, 17, 18, 19, 20, 21, 22, 23, 24, 25 or more amino acids positioned between one or more of the MUC1 repeats that make up a tandem repeat MUC1 decoy peptide.

Sequence Variants

The MUC1 decoy peptides of the invention can have variability in their amino acid composition without adversely affecting the activity of the peptide. For example, the peptides can have amino acid additions, deletions and/or substitutions (conservative and/or non-conservative), and any combination thereof. The MUC1 decoy peptides of the invention thus include sequence variants having at least 80%, 81%, 82%, 83%, 84%, 85%, 86%, 87%, 88%, 89%, 90%, 91%, 92%, 93%, 94%, 95%, 96%, 97%, 98% or 99% sequence identity with a MUC1 decoy peptide as defined herein, over the entire length of the amino acid sequence of the peptide. Such variants include variants of single repeat MUC1 decoy peptides, tandem repeat MUC1 decoy peptides and ectodomain MUC1 decoy peptides. Each of the MUC1 decoy peptides shares the characteristic of being able to be specifically bound by flagellin, though it will be clear that the ability of particular repeats to bind flagellin may vary based on their sequence. Such variant peptides are termed "sequence variant MUC1 decoy peptides" herein. Each of the sequence variant MUC1 decoy peptides shares the characteristic of being able to be specifically bound by flagellin, though it will be clear that the ability of particular repeats to bind flagellin may vary based on their sequence. Thus, in one aspect the invention is directed to sequence variant MUC1 decoy peptides having at least 80% sequence identity with single repeat MUC1 decoy peptides, sequence variant MUC1 decoy peptides having at least 80% sequence identity with tandem repeat MUC1 decoy peptides, and sequence variant MUC1 decoy peptides having at least 80% sequence identity with ectodomain MUC1 decoy peptides.

In the sequence variant MUC1 decoy peptides having at least 80% sequence identity with ectodomain MUC1 decoy peptides, the sequence variations can be limited to the repeat region, the N-terminal non-repeat region, the C-terminal non-repeat region, or any combination thereof.

Carbohydrate Removal

As indicated herein, variations in MUC1 carbohydrate content can affect the ability of MUC1-ED to be bound by flagellin. The invention includes MUC1 decoy peptides having innate carbohydrate content (e.g., MUC1 decoy peptides produced by mammalian cells without alteration in carbohydrate content), desialylated MUC1 decoy peptides (where terminal sialic acid (SA) residues are moved), and deglycosylated MUC1 decoy peptides (where all carbohydrate residues subterminal to SA are also removed).

Other Variations

The MUC1 decoy peptides of the invention also include conformation variants, e.g., MUC1 decoy peptide multimers where two or more decoy peptide molecules are linked or decoy peptides are cyclized, and MUC1 decoy peptides attached to carriers such as polyethylene glycol (PEG) or protein carriers that increase inhibitory bioactivity. MUC1 decoy peptides are also amenable to chemical modifications, for example by PEGylation to attach a polyethylene glycol derivative, in order to maximize deliverability, bioavailability, half-life, stability, and other beneficial therapeutic properties. The amino acids comprising the MUC1 decoy peptides include amino acids in their natural form, nonstandard amino acids, and synthetic variants thereof. The amino acids may be in L- or D-configuration. The amino acids may be modified by methylation, amidation, acetylation or substitution with other chemical groups which may change the circulating half-life of the peptide without adversely affecting their biological activity. Non-limiting examples of non-standard amino acids include 4-hydroxyproline, 5-hydroxylysine, 6-N-methyllysine, gamma-carboxyglutamate, desmosine, selenocysteine, ornithine, citrulline, lanthionine, 1-aminocyclopropane-1-carboxylic acid, gamma-aminobutyric acid, carnitine, sarcosine, or N-formylmethionine. Synthetic variants of standard and non-standard amino acids are also known and may include chemically derivatized amino acids, amino acids labeled for identification or tracking, or amino acids with a variety of side groups on the alpha carbon. Examples of such side groups are known in the art and may include aliphatic, single aromatic, polycyclic aromatic, heterocyclic, heteronuclear, amino, alkylamino, carboxyl, carboxamide, carboxyl ester, guanidine, amidine, hydroxyl, alkoxy, mercapto-, alkylmercapto-, or other heteroatom-containing side chains. Other synthetic amino acids may include alpha-amino acids, non-alpha amino acids such as beta-amino acids, des-carboxy or des-amino acids.

Polynucleotide Sequences

The invention also encompasses the polynucleotide sequences encoding each of the MUC1 decoy peptides of the invention. Specific polynucleotide sequences encompassed within the scope of the invention include the polynucleotide sequence set forth in SEQ ID NO:7, which encodes the MUC1 decoy peptide of SEQ ID NO:3. The skilled artisan will understand that due to the redundancy of the genetic code, there are a large number of different polynucleotide sequences that encode a single decoy peptide. The invention includes each polynucleotide sequence encoding a MUC1 decoy peptide of the invention.

Source of Decoy Peptides

The source of the MUC1 decoy peptides of the invention is unlimited and includes, for example, peptides isolated and purified from a subject, peptides isolated from an in vitro culture (e.g., a cultured mammalian, insect, yeast, or bacterial cell line engineered to express the peptide), and synthetic peptides produced using a protein synthesizer. Glycosylated peptides produced using a protein synthesizer can be glycosylated in vitro, if desired, using known methods.

Cells

The present invention also encompasses cells engineered to produce the MUC1 decoy peptides of the invention. The identity of such cells is only limited by the ability of the cell to produce the variant. In preferred aspects, the cell can both produce the decoy peptide and express it on the surface of the cell or export the decoy peptide out of the cell. The cells include mammalian cells, such as human or mouse cells, insect cells, eukaryotic cells such as yeast cells, and prokaryotic cells, such as bacterial cells, including *E. coli*.

Cells may be engineered to express the MUC1 decoy peptides of the invention by means readily known to the skilled artisan. Generally, a polynucleotide vector is constructed that encodes a decoy peptide and the vector is transfected into a population of cells, such as *E. coli*. The cells are then grown under conditions promoting expression of the decoy peptide.

Unglycosylated, desialylated, deglycosylated, or glycosylated forms of MUC1 decoy peptides can be produced by any means available to the skilled artisan. In one non-limiting example, since bacteria lack the cellular machinery necessary for robust post-translational glycosylation of eukaryotic proteins (62), unglycosylated forms of the MUC1 decoy peptides can be prepared by transforming *E. coli* with a MUC1 expression plasmid (pMUC1). Unglycosylated MUC1 decoy peptides can also be produced in yeast or other cells that have been genetically engineered to destroy their glycosylating activity. In addition, any method for desialylating or deglycosylating MUC1 decoy peptides can be used (e.g., desialylating or deglycosylating glycosylated peptides in vitro using desialylating or deglycosylating enzymes according to methods available to the skilled artisan). In another non-limiting example, desialylated MUC1 decoy peptides may be prepared from culture supernates of airway ECs infected with Ad-NEU1 as described below.

Methods of Treatment and Prevention

The MUC1 decoy peptides of the present invention may be used in methods of treating or preventing a bacterial infection in a subject.

These methods are unique in their approach because they utilize therapeutic peptide compounds based on the naturally-produced MUC1 protein. Current strategies typically rely on antibiotic drugs alone, which have unintentionally led to the emergence of difficult-to-treat, drug resistant bacteria. Second-generation antibiotics that replace drugs to which the bacteria have become resistant, in many cases, are limited by their toxicity. The methods of the present invention are believed to be the first to use a native human protein or a synthetic variation thereof to treat bacterial infections that avoid antibiotic resistance and drug toxicity. However, in certain aspects of the invention, the MUC1 decoy peptides may be used in conjunction with other antibacterial agents, such as antibiotics, in the treatment or prevention of a bacterial infection in a subject. Such combinations may result in additive or synergistic effects on the targeted bacteria, although the invention is not limited to combinations that produce such results.

Infectious bacteria, such as *P. aeruginosa*, bind to MUC1-ED expressed by epithelial cells and then invade the epithelial cell layer. By administering a soluble form of MUC1-ED or MUC1-ED mimetic, e.g., the MUC1 decoy peptides of the invention, to a subject having a bacterial infection or at risk of developing such an infection, interactions between the bacteria and receptors on the cell surface can be inhibited. Bacterial infections can thereby be minimized, treated, or even blocked. Administration of other antibacterial agents, such as antibiotics, can further aid in minimizing, treating, and blocking of certain infections.

The invention thus includes methods of treating and/or preventing a bacterial infection in a subject. The methods comprise administering a therapeutically effective amount of one or more MUC1 decoy peptides to a subject in need thereof, such as a subject having a bacterial infection or a subject at risk of developing a bacterial infection. The methods include administration of the MUC1 decoy peptides in a pharmaceutical formulation comprising the one or more MUC1 decoy peptides and a pharmaceutically acceptable carrier or diluent.

The MUC1 decoy peptide may be any of the MUC1 decoy peptides defined herein, for example, one or more members selected from the group consisting of:

(a) a single repeat MUC1 decoy peptide comprising at least 15 contiguous amino acids of GSTAPPAHGVTSAPDTRPAP (SEQ ID NO:1), (b) a tandem repeat MUC1 decoy peptide comprising at least five MUC1 repeats, wherein each MUC1 repeat comprises at least 15 contiguous amino acids of GSTAPPAHGVTSAPDTRPAP (SEQ ID NO:1) and wherein the sequence of each MUC1 repeat may vary in the peptide, (c) an ectodomain MUC1 decoy peptide comprising the amino acid sequence MTPGTQSPFFLLLLLTVLTVVTGS-GHASSTPGGEKETSATQRSSVPSSTEKNAVSMTSSV LSSHSPGSGSSTTQGQDVTLAPATE-PASGSAATWGQDVTSVPVTRPALGSTTPPAHDVTS APDNKPAP
XGSTAPPAHGVTSAPDNRPALGSTAPPVHNVTSAS-
GSASGSASTLVHNGTS ARATTTPASKSTPFSIPSHHS-
DTPTTLASHSTKTDASSTHHSTVPPLTSSNHSTSPQL-
STGV SFFFLSFHISNLQFNSSLEDPSTDYYQELQRDIS-
EMFLQIYKQGGFLGLSNIKFRPG (SEQ ID NO:2),
wherein X is at least five MUC1 repeats, wherein each
MUC1 repeat comprises at least 15 contiguous amino acids
of GSTAPPAHGVTSAPDTRPAP (SEQ ID NO:1) and
wherein the sequence of each MUC1 repeat may vary in the
peptide, (d) a sequence variant MUC1 decoy peptide having at
least 80% sequence identity to a peptide of (a), (b) or (c), (e) a desialylated version of a peptide of (a), (b), (c) or (d),
and (f) a deglycosylated version of a peptide of (a), (b), (c) or
(d).

In a specific aspect this embodiment, the decoy peptide
may be the ectodomain MUC1 decoy peptide set forth in
SEQ ID NO:3. In a specific aspect of this embodiment, the
invention is directed to a method of treating a bacterial
infection in a subject comprising administering a therapeutically
effective amount of a MUC1 decoy peptide to a
subject in need thereof, wherein the MUC1 decoy peptide is
one or more members of the group defined above, i.e. the
group of (a) through (f). In another specific aspect of this
embodiment, the invention is directed to a method of preventing
a bacterial infection in a subject comprising administering
a therapeutically effective amount of a MUC1 decoy
peptide to a subject in need thereof, wherein the MUC1
decoy peptide is one or more members of the group defined
above, i.e. the group of (a) through (f).

The invention includes methods of treating and/or preventing
a bacterial infection in a subject where an antibacterial
agent, such as an antibiotic, is administered to the
subject in conjunction with the MUC1 decoy peptides.
These methods comprise administering (i) a therapeutically
effective amount of one or more MUC1 decoy peptides and
(ii) a therapeutically effective amount of one or more antibacterial
agents to a subject in need thereof, such as a subject
having a bacterial infection or a subject at risk of developing
a bacterial infection. The methods include administration of
the MUC1 decoy peptides in a pharmaceutical formulation
comprising the one or more MUC1 decoy peptides and a
pharmaceutically acceptable carrier or diluent, and administration
of the antibacterial agents in a pharmaceutical
formulation comprising the one or more antibacterial agents
and a pharmaceutically acceptable carrier or diluent. In
certain aspects, the MUC1 decoy peptides and the antibacterial
agents are in separate formulations, In other aspects,
the MUC1 decoy peptides and the antibacterial agents are in
the formulation.

The MUC1 decoy peptide may be any of the MUC1 decoy
peptides defined herein, for example, one or more members
selected from the group consisting of:

(a) a single repeat MUC1 decoy peptide comprising at
least 15 contiguous amino acids of GSTAPPAHGVTSAP-
DTRPAP (SEQ ID NO:1), (b) a tandem repeat MUC1 decoy peptide comprising at
least five MUC1 repeats, wherein each MUC1 repeat comprises
at least 15 contiguous amino acids of GSTAPPAH-
GVTSAPDTRPAP (SEQ ID NO:1) and wherein the
sequence of each MUC1 repeat may vary in the peptide, (c) an ectodomain MUC1 decoy peptide comprising the
amino acid sequence MTPGTQSPFFLLLLLTVLTVVTGS-
GHASSTPGGEKETSATQRSSVPSSTEKNAVSMTSSV
LSSHSPGSGSSTTQGQDVTLAPATE-
PASGSAATWGQDVTSVPVTRPALGSTTPPAHDVTS
APDNKPAP
XGSTAPPAHGVTSAPDNRPALGSTAPPVHNVTSA-
SGSASGSASTLVHNGTS ARATTTPASKSTPFSIPSHHS-
DTPTTLASHSTKTDASSTHHSTVPPLTSSNHSTSPQL-
STGV SFFFLSFHISNLQFNSSLEDPSTDYYQELQRDIS-
EMFLQIYKQGGFLGLSNIKFRPG (SEQ ID NO:2),
wherein X is at least five MUC1 repeats, wherein each
MUC1 repeat comprises at least 15 contiguous amino acids
of GSTAPPAHGVTSAPDTRPAP (SEQ ID NO:1) and
wherein the sequence of each MUC1 repeat may vary in the
peptide, (d) a sequence variant MUC1 decoy peptide having at
least 80% sequence identity to a peptide of (a), (b) or (c), (e) a desialylated version of a peptide of (a), (b), (c) or (d),
and (f) a deglycosylated version of a peptide of (a), (b), (c) or
(d).

The antibacterial agents include antibiotics, antiseptics,
disinfectants, bactericidal agents, and bacteriostatic agents.
In certain aspects, the antibacterial agents are one or more
antibiotics. Suitable antibiotics for use in the methods of the
present invention include an antibiotic with activity against
*P. aeruginosa*, an antibiotic with activity against *Helicobacter
pylori*, an antibiotic with activity against *Campylobacter
jejuni*, an antibiotic with activity against *Escherichia
coli*, an antibiotic with activity against *Salmonella
enterica*, an antibiotic with activity against *Burkholderia
cenocepacia*, an antibiotic with activity against *Burkholderia
pseudomallei*, an antibiotic with activity against *Stenotrophomonas
maltophilia*, an antibiotic with activity against
*Legionella pneumophila*, an antibiotic with activity against
*Bordetella bronchiseptica*, an antibiotic with activity against
*Enterobacter* spp., an antibiotic with activity against *Neisseria
gonorrhoeae*, an antibiotic with activity against *Bacillus
cereus*, an antibiotic with activity against *Bacillus subtilis*,
an antibiotic with activity against *Actinobacillus
pleuropneumoniae*, and an antibiotic with activity against
*Yersinia pseudotuberculosis*. Suitable antibiotics for use in
the methods of the present invention also include aminoglycosides,
amoxicillin, ampicillin, azithromycin, aztreonam,
carbapenems, cefepime, cefixime, cefotaxime, ceftazidime,
ceftiofur, ceftobiprole, ceftriaxone, cephalosporins,
chloramphenicol, cilastatin, ciprofloxacin, clarithromycin,
clindamycin, doxycycline, enrofloxacin, erythromycin, fluoroquinolones,
gemifloxacin, gentamicin, imipenem, levofloxacin,
marbofloxacin, meropenem, metronidazole, minocycline,
moxifloxacin, nitrofurantoin, penicillin,
piperacillin, pradofloxacin, streptomycin, sulfamethoxazole,
sulfonamides, tetracycline, ticarcillin, tigecycline,
trimethoprim, tobramycin, trovofloxacin, tylosin, and vancomycin.
In a particular aspect, the antibiotic is cefepime.

In a specific aspect this embodiment, the decoy peptide
may be the ectodomain MUC1 decoy peptide set forth in
SEQ ID NO:3 and the antibacterial agent may be cefepime.
In a specific aspect of this embodiment, the invention is
directed to a method of treating a bacterial infection in a
subject comprising administering (i) a therapeutically effective
amount of a MUC1 decoy peptide and (ii) a therapeutically
effective amount of cefepime to a subject in need
thereof, wherein the MUC1 decoy peptide is one or more
members of the group defined above. In another specific
aspect of this embodiment, the invention is directed to a
method of preventing a bacterial infection in a subject
comprising administering (i) a therapeutically effective
amount of a MUC1 decoy peptide and (ii) a therapeutically effective amount of cefepime to a subject in need thereof, wherein the MUC1 decoy peptide is one or more members of the group defined above.

When MUC1 decoy peptides are administered in conjunction with antibacterial agents, such as antibiotics, the peptides and agents may be administered to the subject together or separately. The peptides and agents may be administered in the same formulation or in separate formulations. When the peptides and agents are administered separately, they may be administered in either order; their administration may be separated in time (administration of one is completed before the other begins) or overlap in time; their administration may be via the same means or separate means.

As used herein, the terms "treat", "treating", and "treatment" have their ordinary and customary meanings, and include one or more of: blocking, ameliorating, or decreasing in severity and/or frequency a symptom of a bacterial infection in a subject, and/or inhibiting the growth, division, spread, or proliferation of bacterial cells or a bacterial infection in a subject. Treatment means blocking, ameliorating, decreasing, or inhibiting by about 1% to about 100% versus a subject in which the methods of the present invention have not been practiced. Preferably, the blocking, ameliorating, decreasing, or inhibiting is about 100%, 99%, 98%, 97%, 96%, 95%, 90%, 80%, 70%, 60%, 50%, 40%, 30%, 20%, 10%, 5% or 1% versus a subject in which the methods of the present invention have not been practiced.

As used herein, the terms "prevent", "preventing" and "prevention" have their ordinary and customary meanings, and include one or more of, stopping, averting, avoiding, alleviating or blocking an infection from colonizing, developing or progressing in a subject, and/or stopping, averting, avoiding, alleviating or blocking the growth, division, spread, or proliferation of bacterial cells or bacterial infection in a subject. Prevention means stopping by at least about 95% versus a subject to which the prevention has not been administered. Preferably, the stopping is about 100%, about 99%, about 98%, about 97%, about 96% or about 95%. The results of the prevention may continue for a period of days (such as 1, 2, 3, 4, 5, 6 or 7 days), weeks (such as 1, 2, 3 or 4 weeks) or months (such as 1, 2, 3, 4, 5, 6 or more months).

As used herein, the term "antibacterial agent" is an agent that inhibits bacterial growth or kills bacteria. Inhibition of growth means inhibiting growth by about 1% to about 100% versus bacteria that have not been exposed to antibacterial agent. Preferably, the inhibiting is about 100%, 99%, 98%, 97%, 96%, 95%, 90%, 80%, 70%, 60%, 50%, 40%, 30%, 20%, 10%, 5% or 1% versus bacteria that have not been exposed to antibacterial agent. An "antibiotic with activity against" a particular species or strain of bacteria is synonymous with an antibacterial agent. As used herein, the term "antibiotic" refers to an antibacterial agent that inhibits bacterial growth or kills bacteria on or within the body of a subject.

Infections

Hospital-acquired *Pseudomonas aeruginosa* infections are a common cause of pneumonia and infections of the bloodstream, urinary tract, skin, and surgical sites. Community-acquired *P. aeruginosa* infections outside of the hospital include airway infections in cystic fibrosis patients and infections of the eye (keratitis) and ear (swimmers' ear). In hospitalized patients with ventilator-associated pneumonia, *P. aeruginosa* accounts for approximately 20% of cases. In addition to pulmonary tract infections, *P. aeruginosa* also infects the urinary tract (70,000 U.S. cases per year) and burn wounds (17,000 U.S. cases per year). It also results in serious blood infections, and is the most frequent colonizer of medical devices such as catheters. *Pseudomonas aeruginosa* infections are often life-threatening and difficult to treat. The increasing frequency of multi-drug-resistant *P. aeruginosa* (MDRPA), which account for 7,000 infections annually in the U.S., is concerning as alternative antibiotics are severely limited by their toxicity. MDRPA infections have been described in patients with cystic fibrosis or immunocompromised conditions, and in critically ill patients in intensive care units, thus raising concerns among healthcare providers due to the scarcity of alternative treatment options.

The bacteria that is the source of the infections that may be treated or prevented using the methods of the present invention may be any bacteria that expresses a flagellin protein that can bind MUC1-ED. Exemplary bacteria include, but are not limited to *P. aeruginosa* (such as MDRPA), *Helicobacter pylori*, *Campylobacter jejuni*, *Escherichia coli*, *Salmonella enterica*, *Burkholderia cenocepacia*, *Burkholderia pseudomallei*, *Stenotrophomonas maltophilia*, *Legionella pneumophila*, *Bordetella bronchiseptica*, *Enterobacter* spp., *Neisseria gonorrhoeae*, *Bacillus cereus*, *Bacillus subtilis*, *Actinobacillus pleuropneumonias*, and *Yersinia pseudotuberculosis*.

It will be clear to the skilled artisan that the bacterial infection itself is not particularly limited and included such bacterial infection as pulmonary infections (including infections in the lungs of subjects with cystic fibrosis and ventilator-associated pneumonia), skin infections (including burns, wounds, and infections of surgical sites), blood infections (including sepsis), urinary tract infections, and infections of the eye or ear. The source of the infection is also unlimited and include hospital-acquired (nosocomial) and community-acquired infections. In a particular aspect of the invention, the infection is a *P. aeruginosa* pulmonary infection.

Pharmaceutical Formulations

While the MUC1 decoy peptides may be administered directly to a subject, the methods of the present invention are preferably based on the administration of a pharmaceutical formulation comprising one or more MUC1 decoy peptides and a pharmaceutically acceptable carrier or diluent. Similarly, while the antibacterial agents may be administered directly to a subject, the methods of the present invention are preferably based on the administration of a pharmaceutical formulation comprising one or more antibacterial agents and a pharmaceutically acceptable carrier or diluent. As indicated above, when the methods of the invention are practiced via administration of both MUC1 decoy peptides and antibacterial agents, the peptides and agents can be formulated in the same pharmaceutical formulation or in different formulations.

Pharmaceutically acceptable carriers and diluents are commonly known and will vary depending on the particular decoy peptide or antibacterial agent being administered and the modes of administration. Examples of generally used carriers and diluents include, without limitation: saline, buffered saline, dextrose, water-for-infection, glycerol, ethanol, and combinations thereof, stabilizing agents, solubilizing agents and surfactants, buffers and preservatives, tonicity agents, bulking agents, and lubricating agents. The formulations comprising MUC1 decoy peptides and antibacterial agents will typically have been prepared and cultured in the absence of any non-human components, such as animal serum (e.g., bovine serum albumin).

A formulation may include MUC1 decoy peptides having the same sequence and/or physical characteristics, or MUC1 decoy peptides having different sequences and/or physical characteristics. Similarly, a formulation may include one type of antibacterial agent, or different types of antibacterial agents when more than one antibacterial agent is administered to a subject.

Pharmaceutical formulations comprising one or more MUC1 decoy peptides and/or one or more antibacterial agents may be administered to a subject using modes and techniques known to the skilled artisan. Exemplary modes include, but are not limited to, intravenous injection and aerosol administration. Other modes include, without limitation, intratumoral, intradermal, subcutaneous (s.c., s.q., sub-Q, Hypo), intramuscular (i.m.), intraperitoneal (i.p.), intra-arterial, intramedulary, intracardiac, intra-articular (joint), intrasynovial (joint fluid area), intracranial, intraspinal, and intrathecal (spinal fluids). The MUC1 decoy peptides of the invention and antibacterial agents can also be coated onto catheters such as urinary catheters, endotracheal tubes, nasal tubes, nasogastric tubes, or any medical device that can serve as a scaffold for infection by *P. aeruginosa* or other bacteria as described herein. Particularly relevant to the aerosolized means for administration, many current medications for treatment of lung diseases are delivered as aerosols, such as inhaled Pulmozyme and tobramycin for cystic fibrosis. Therefore, the same technologies for aerosolized drug delivery, as well as patient acceptance of these technologies, already exist in the marketplace.

The pharmaceutical formulations of the present invention may be formulated for intranasal or inhalation administration, whether through nasal or buccal administration, or other means that deliver the decoy peptides to near the epithelia of the respiratory system, using conventional diluents, carriers, excipients and/or propellants, through formulations such as nose drops, mists, etc. In one embodiment, the pharmaceutical formulations are administered by transbronchoscopic lavage. In particular embodiments, the decoy peptides are deposited in the respiratory system by administering an aerosol suspension of respirable particles comprising the active agent (i.e., decoy peptides) through inhalation by the subject. The respirable particles may be liquid or solid (dry).

Aerosols of liquid particles comprising the active agent may be produced by any suitable means, such as with a pressure-driven aerosol nebulizer or an ultrasonic nebulizer. Nebulizers are commercially available devices which transform solutions or suspensions of an active agent into a therapeutic aerosol mist either by means of acceleration of compressed gas, typically air or oxygen, through a narrow vent or orifice, or by means of ultrasonic agitation. Suitable formulations for use in nebulizers consist of the active agent in a liquid carrier. The carrier is typically water (and most preferably sterile, pyrogen-free water) or a dilute aqueous alcoholic solution.

Aerosols of solid particles comprising the active agent may likewise be produced by any solid particulate aerosol generator. Aerosol generators for administering solid particulates to a subject generate a volume of aerosol containing a predetermined metered dose of an active agent at a rate suitable for human administration. One illustrative type of a solid particulate aerosol generator is an insufflator. Suitable formulations for administration by insufflation include fine powders which may be delivered by means of an insufflator or taken into the nasal cavity in the manner of a snuff In the insufflator, the powder (e.g., a pre-selected dose) is contained in a capsule or cartridge, typically made of gelatin or plastic, that is either pierced or opened in situ and the powder is delivered by air drawn through the device upon inhalation or by means of a manually-operated pump. The powder employed in the insufflator may consist of either the active agent alone, or a powder blend comprising the active agent and a carrier, such as lactose, and an optional surfactant. A second type of illustrative aerosol generator is a metered dose inhaler. Metered dose inhalers are pressurized aerosol dispensers, typically containing a suspension or solution formulation of the active agent in a liquified propellant. These devices discharge the formulation through a valve adapted to deliver a metered volume during use, typically from 10 to 150 µl, to produce a fine particulate spray containing the active agent. Suitable propellants include, and are not limited to, certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants, such as oleic acid or sorbitan trioleate, antioxidants and suitable flavoring agents.

Inhalable formulations comprising particles of the decoy peptides should include particles of respirable size, that is, particles of a size sufficiently small to pass through the mouth and larynx upon inhalation and into the bronchi, bronchioles, and the alveoli of the lungs. In general, particles of less than about 6 microns in size are respirable. In one aspect, the particles of aerosol formations of the present invention are between about 1 and 5 microns. For nasal administration, a particle size in the range of about 10-500 microns is suitable to ensure retention in the nasal cavity. The decoy peptides themselves may be formulated into particles of the appropriate size, or the decoy peptides may be formulated with a carrier of the appropriate size.

The potential acidity and/or bitter taste of the decoy peptides can also be addressed by preparing nanoparticle formulations of decoy peptides for intranasal or inhalation administration. Nanoparticles formulations generally comprise submicron (<1 µm) colloidal particles, which includes monolithic nanoparticles (nanospheres) in which the drug is adsorbed, dissolved, or dispersed throughout a matrix, and nanocapsules in which the drug is confined to an aqueous or oily core surrounded by a shell-like wall. The drug can alternatively be covalently attached to the surface or into the matrix. Nanoparticles can be made from biocompatible and biodegradable materials such as polymers, either natural (e.g., gelatin, albumin) or synthetic (e.g., polylactides, polyalkylcyanoacrylates), or solid lipids. In the body, the drug loaded in nanoparticles is typically released from the matrix by diffusion, swelling, erosion, or degradation. Thus, the formulations of the present invention may contain microspheres, microcapsules, nanoparticles or the like.

The formulations comprising MUC1 decoy peptides that are administered to a subject comprise an amount of the peptides that is effective for the treatment or prevention of a particular infection. Thus, therapeutically effective amounts of formulations comprising MUC1 decoy peptides are administered to subjects when the methods of the present invention are practiced. In general, formulations are administered that comprise between about 0.01 and 10,000 µg, between about 0.1 and 1,000 µg, or between about 1.0 and 100 µg of decoy peptide. However, the amount of decoy peptide administered to a subject will vary between wide limits, depending upon the location, source, identity, extent and severity of the infection, the age and condition of the subject to be treated, etc. A physician will ultimately determine appropriate dosages to be used.

Administration frequencies of the MUC1 decoy peptides and pharmaceutical formulations comprising the decoy peptides will vary depending on factors that include the identity of the bacteria, the source of the bacterial infection, the particulars of the infection to be treated or prevented, and the mode of administration. Each formulation may be independently administered 4, 3, 2 or once daily, every other day, every third day, every fourth day, every fifth day, every sixth day, once weekly, every eight days, every nine days, every ten days, bi-weekly, monthly and bi-monthly.

The formulations comprising an antibacterial agent that are administered to a subject comprise an amount of the agent that is effective for the treatment or prevention of a particular infection. Thus, therapeutically effective amounts of formulations comprising antibacterial agents are administered to subjects when the methods of the present invention are practiced. In general, formulations are administered that comprise between about 0.01 and 10,000 µg, between about 0.1 and 1,000 µg, or between about 1.0 and 100 µg of an antibacterial agent. However, the amount of antibacterial agent administered to a subject will vary between wide limits, depending upon the location, source, identity, extent and severity of the infection, the age and condition of the subject to be treated, the amount and identity of the MUC1 decoy peptide, etc. A physician will ultimately determine appropriate dosages to be used.

Administration frequencies of the antibacterial agents and pharmaceutical formulations comprising the antibacterial agents will vary depending on factors that include the identity of the bacteria, the source of the bacterial infection, the particulars of the infection to be treated or prevented, and the mode of administration. Each formulation may be independently administered 4, 3, 2 or once daily, every other day, every third day, every fourth day, every fifth day, every sixth day, once weekly, every eight days, every nine days, every ten days, bi-weekly, monthly and bi-monthly.

The duration of treatment or prevention will be based on the bacteria or the infection being treated or prevented, and will be best determined by the attending physician. However, continuation of treatment is contemplated to last for a number of days, weeks, or months.

In each embodiment and aspect of the invention, the subject is a human, a non-human primate, bird, horse, cow, goat, sheep, a companion animal, such as a dog, cat or rodent, or other mammal. The subjects to which the methods of the present invention can be applied include subjects having an underlying disease or condition that makes them more susceptible to bacterial infections of the respiratory system. Such subjects include, and are not limited to, those afflicted with cystic fibrosis; lung cancer; an obstructive lung disease, such as chronic obstructive pulmonary disease and asthma; chronic bronchitis; a restrictive lung disease; emphysema; primary and secondary ciliary dyskinesia; sinusitis; mesothelioma; pneumonia; ventilator-associated pneumonia; hospital-acquired pneumonia; community-acquired bacterial pneumonia. Human subjects of both genders and at any stage of development (i.e., neonate, infant, juvenile, adolescent, adult) can be treated according to the present invention. In one aspect of each embodiment, the subject is a human afflicted with cystic fibrosis.

The invention also provides a kit comprising one or more containers filled with one or more MUC1 decoy peptides or pharmaceutical formulations comprising MUC1 decoy peptides. The kit may also comprise one or more containers filled with one or more antibacterial agents or pharmaceutical formulations comprising one more antibacterial agents. The kit may further comprise one or more containers filled with (i) one or more antibacterial agents and (ii) one or more MUC1 decoy peptides or pharmaceutical formulations comprising (i) one or more antibacterial agents and (ii) one or more MUC1 decoy peptides. The kit may also include instructions for use. Associated with the kit may further be a notice in the form prescribed by a governmental agency regulating the manufacture, use or sale of pharmaceuticals or biological products, which notice reflects approval by the agency of manufacture, use or sale for human administration.

Methods of Screening

As indicated above, the invention also includes methods of determining whether a subject has been colonized by a selected bacteria or whether a subject has an infection of a selected bacteria. The methods comprising screening a biological sample from a subject for shed MUC1 ectodomain, wherein when MUC1 ectodomain is detected in the sample, the subject is deemed to have been colonized by the selected bacteria or the subject has is deemed to have an infection of a selected bacteria.

The bacteria may be any bacteria that expresses a flagellin protein that can bind MUC1-ED. Exemplary bacteria include, but are not limited to *P. aeruginosa* (such as MDRPA), *Helicobacter pylori*, *Campylobacter jejuni*, *Escherichia coli*, *Salmonella enterica*, *Burkholderia cenocepacia*, *Burkholderia pseudomallei*, *Stenotrophomonas maltophilia*, *Legionella pneumophila*, *Bordetella bronchiseptica*, *Enterobacter* spp., *Neisseria gonorrhoeae*, *Bacillus cereus*, *Bacillus subtilis*, *Actinobacillus pleuropneumonias*, and *Yersinia pseudotuberculosis*.

The biological sample may be any that will contain or made to contain shed MUC1-ED. Samples taken directly from a subject include, for example, blood, serum, sweat, tears, pleural fluid, sputum, mucous, nasal discharge, etc. Suitable biological samples can also be prepare by washing an area or region of the subject's body, for example, bronchoalveolar lavage fluid (BALF), obtained from non-bronchoscopic techniques (including mini-BAL, blinded protected specimen brush (PSB), and blinded bronchial sampling), endotracheal aspiration, a swabbing from an infected or potentially infected wound area (such as a skin wound), etc.

It will be apparent that the biological sample can be screened for the presence of shed MUC1-ED and even the particular amount of shed MUC1-ED in the sample using a variety of means, including, for example, anti-MUC1-ED antibody-based screens (e.g., enzyme-linked immunosorbent assay (ELISA), lateral flow immunoassay, magnetic immunoassay, radioimmunoassay, fluorescent immunosassay, Western immunoblot assay, dot immunoblot assay, and slot immunoblot assay, etc.).

III. Examples

Example 1

Materials and Methods

Airway ECs and Ad Constructs.

Human A549 lung carcinoma cells (American Type Culture Collection) and primary small airway epithelial cells (SAECs) (PromoCell) were cultured as described (Lillehoj et al., 2012). The ECs were infected with recombinant Ad encoding FLAG-tagged NEU1 (Ad-NEU1-FLAG), hemagglutinin (HA)-tagged NEU3 (Ad-NEU3-HA), catalytically-inactive NEU1 containing a Gly$^{68}$-to-Val substitution (Ad-NEU1-G68V), or GFP as described (Lillehoj et al., 2012).

Bacterial Adhesion and Invasion Assays.

Airway ECs and ECs infected with Ad constructs, transfected with siRNAs, and/or stimulated with flagellin (2.0×

$10^5$ ECs/well) were washed with PBS, fixed for 10 min with 2.5% glutaraldehyde, and washed. The ECs were incubated with bacteria (MOI=100), washed, and bound bacteria were quantified as described (Lillehoj et al., 2012). For invasion assays, $2.0 \times 10^5$ ECs/well were incubated for 1 h with *P. aeruginosa* (Pa) (MOI=100), washed, incubated for 1 h with 200 µg/ml of gentamicin, washed, lysed with 0.1% Triton X-100, and CFUs enumerated.

Knockdown of NEU1 and MUC1.

NEU1 and MUC1 silencing using siRNAs was performed as described (Lillehoj et al., 2012).

Immunoblotting Assays. Airway ECs infected with Ad constructs or transfected with siRNAs were lysed, and equal protein aliquots of lysates resolved by SDS-PAGE and transferred to polyvinylidene fluoride (PVDF) membranes. The membranes were probed with primary antibody followed by HRP-conjugated secondary antibody and enhanced chemiluminescence (ECL) reagents.

Purification of Pa Flagellin.

Flagellin was purified from Pa strain PA01 as described (Lillehoj et al., 2002).

Flagellin Binding Assays.

Airway ECs infected with Ad constructs ($2.0 \times 10^5$ ECs/well) were exposed for 40 min at 4° C. to increasing concentrations of Alexa Fluor 594-labeled flagellin (Lillehoj et al., 2002). The ECs were washed and bound flagellin was determined by fluorometry ($\lambda_{ex}$=591 nm, $\lambda_{ex}$=615 nm). Scatchard transformation of the binding data was performed as described (Kim et al., 1994).

Co-Immunoprecipitation Assays.

Ad-NEU1-FLAG-infected airway ECs ($1.2 \times 10^6$ ECs/well) were incubated for 30 min with Pa (MOI=100), or for increasing times with 10 ng/ml of flagellin or medium alone. The ECs were lysed and the lysates incubated overnight at 4° C. with anti-MUC1-CD antibody (Lillehoj et al., 2012). Immune complexes were immobilized on protein G-agarose for 2 h, washed, resolved by SDS-PAGE, and processed for FLAG (NEU1) immunoblotting.

Lectin Blotting Assays.

Airway ECs infected with Ad constructs or transfected with siRNAs were lysed and the lysates immunoprecipitated with anti-MUC1-ED antibody. The MUC1-ED immunoprecipitates were analyzed by MAL, SNA, or PNA lectin blotting as described (Lillehoj et al., 2012). In other experiments, airway ECs and ECs transfected with NEU1-targeting or control siRNAs were incubated for increasing times with 10 ng/ml of flagellin or medium alone, washed, and lysed. The lysates were incubated overnight at 4° C. with PNA-agarose beads and bound proteins processed for MUC1-ED immunoblotting.

MUC1-ED ELISA.

Airway EC supernates and human BALFs were added to ELISA plates, wells were blocked for 1 h with PBS, pH 7.0, containing 10 mg/ml BSA, and washed with PBS containing 0.05% Tween 20 (PBS-T). The samples were incubated for 2 h at room temperature with 200 g/ml of anti-MUC1-ED antibody, washed with PBS-T, and incubated for 2 h with 200 g/ml of peroxidase-conjugated goat anti-mouse IgG antibody. Bound antibodies were detected with tetramethylbenzidine substrate at $A_{450}$. MUC1-ED levels were calculated from a standard curve of serial dilutions of known concentrations of purified MUC1-ED.

BAL.

BAL was performed as part of a University of Maryland Institutional Review Board-approved human subjects' research protocol using a modification of a previously described procedure (Luzina et al., 2009).

Statistical Analysis.

All values were expressed as means±SEM. Differences between means were compared using the Student's t-test or ANOVA and considered significant at $p<0.05$.

Results

NEU1 Overexpression Selectively Enhances MUC1-Dependent Pa Adhesion to and Invasion of Airway ECs.

NEU1 regulates Pa adhesion to primary human airway ECs (Lillehoj et al., 2012). Whether NEU1 and/or NEU3 regulate airway EC adhesiveness for other respiratory pathogens was determined. Adenovirus (Ad)-NEU1 infection of A549 cells increased their expression of NEU1 (FIG. 3A, upper 2 panels) and enhanced the adhesion of Pa and *Legionella pneumophila* by 2.0- and 1.8-fold, respectively, but not that of *Streptococcus pneumoniae, Haemophilus influenzae, Staphylococcus aureus*, or *Klebsiella pneumoniae*, compared with adhesion to Ad-green fluorescent protein (GFP)-infected airway ECs (FIG. 3B). In contrast, NEU3 overexpression (FIG. 3A, lower 2 panels) did not influence adhesion of any bacteria tested (FIG. 3B). MUC1 silencing (FIG. 3C) completely protected against the NEU1-mediated increase in adhesion of Pa, but not of *L. pneumophila* (FIG. 3D). NEU1 overexpression also enhanced Pa adhesion to primary human small airway ECs (SAECs) 3.4-fold compared with Ad-GFP-infected SAECs (FIG. 3E). Infection with Ad-NEU1, but not with the catalytically-inert NEU1 mutant, Ad-NEU1-G68V (Lee et al., 2014) (FIG. 3F), dose-dependently increased Pa adhesion to airway ECs (FIG. 3G). Pa adhesion to airway ECs is prerequisite to their invasion (Prince, 1992). NEU1 silencing (FIG. 3H) diminished Pa invasion of airway ECs compared with control siRNA-transfected ECs, whereas Ad-NEU1 infection enhanced bacterial invasion compared with either Ad-GFP- or Ad-NEU1-G68V-infected ECs (FIG. 3I). MUC1 silencing (FIG. 3C) reduced NEU1-dependent Pa invasion compared with control siRNA-transfected ECs (FIG. 3J). These data indicate that 1) Pa binds to MUC1 and the Pa-MUC1 interaction is influenced by the MUC1-ED sialylation state, 2) NEU1-responsive adhesion to MUC1 is specific for Pa, 3) while *L. pneumophila* adhesion is also NEU1-dependent, it is not MUC1-dependent, 4) NEU1 catalytic activity is required for its ability to influence MUC1-dependent Pa adhesion, and finally, 5) NEU1 increases MUC1-dependent Pa invasion of airway ECs.

Flagellin is Required for NEU1-Responsive Pa Adhesion and Invasion.

Figure 4:
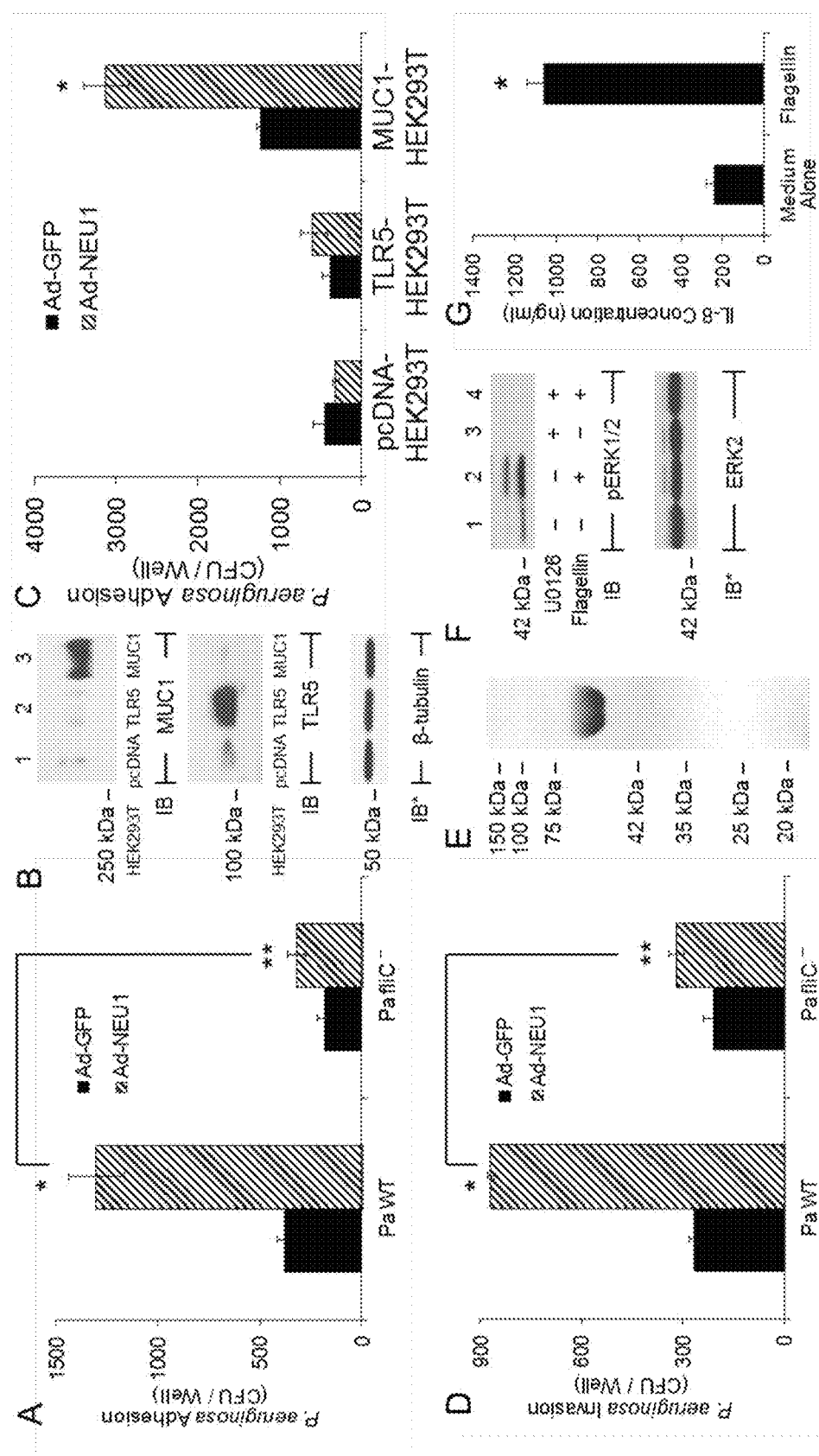
FIG. 4. NEU1 Increases Flagellin-Dependent Pa Adhesion to and Invasion of MUC1-Expressing ECs.
Figure 4:
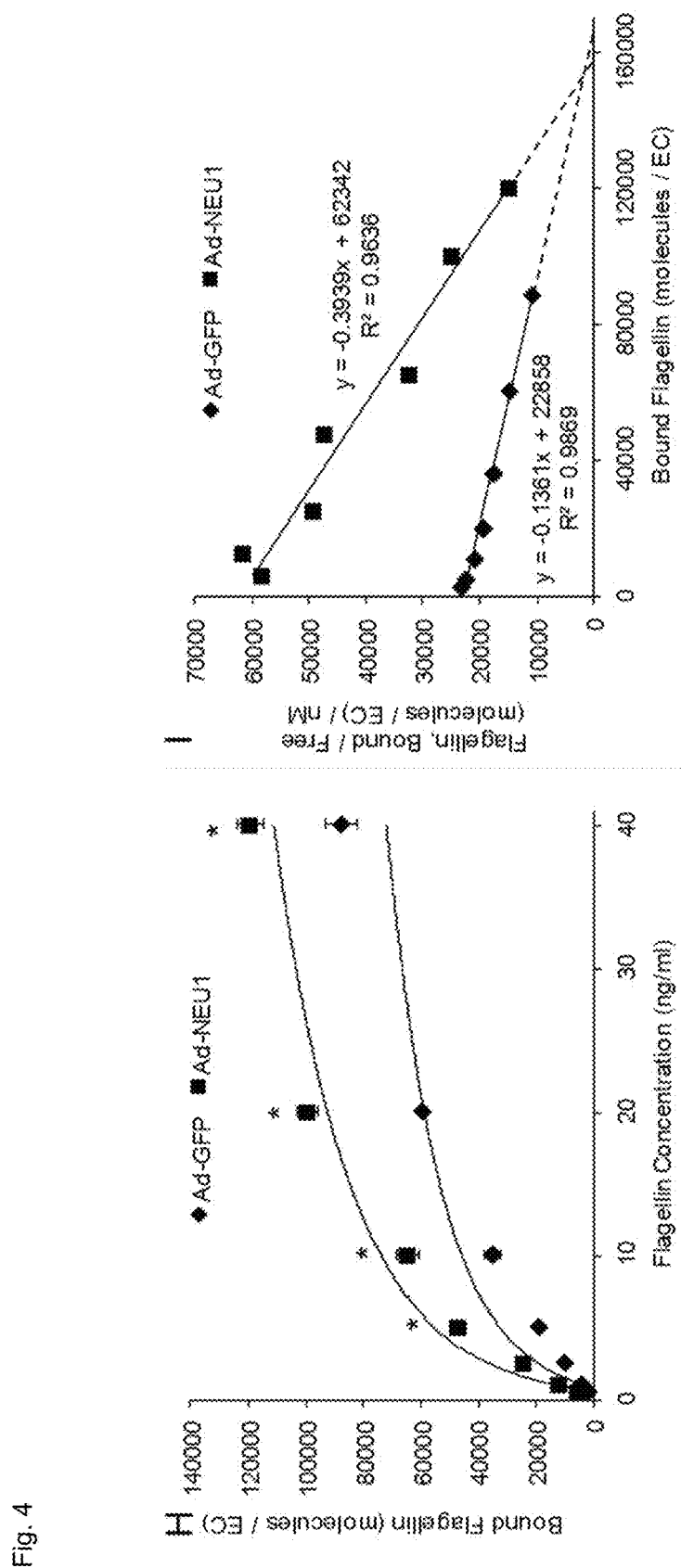

Flagellin was necessary for Pa adhesion to airway ECs (Lillehoj et al., 2002), and NEU1 promotes this adhesion (FIGS. 3B, 3D, 3E, 3G) (Lillehoj et al., 2012). Since Pa expresses multiple EC adhesins (Prince, 1992), it was asked whether flagellin is required for NEU1-responsive Pa adhesion, and if so, might NEU1 augment the binding of flagellin itself to airway ECs. NEU1 overexpression increased the adhesion of flagellin-expressing Pa, but not that of the flagellin-deficient Pa fliC⁻ isogenic mutant (FIG. 4A). Since Pa flagellin is an established ligand for Toll-like receptor (TLR) 5 (Mizel and Bates, 2010), it was asked whether TLR5 contributes to the NEU1 effect on Pa adhesion. HEK293T cells that express extremely low or undetectable endogenous MUC1 or TLR5 were individually transfected for MUC1 expression (FIG. 4B, upper panel), or for TLR5 expression (FIG. 4B, middle panel). Infection of MUC1-expressing HEK293T cells with Ad-NEU1 increased Pa adhesion compared with Ad-GFP-infected cells, whereas Ad-NEU1 infection of TLR5-expressing HEK293T cells did not (FIG. 4C). Since flagellin is required for NEU1-regulated Pa adhesion to airway ECs (FIG. 4A), it was asked whether flagellin is also required for NEU1-responsive Pa invasion. NEU1 overexpression increased invasion of flagellin-expressing Pa but not Pa fliC⁻ (FIG. 4D). Finally, it was asked whether NEU1 promotes the binding of purified flagellin to airway ECs. To validate the flagellin preparation, which migrated as a single band on Coomassie blue-stained SDS-PAGE gels (FIG. 4E), two previously established Pa flagellin-stimulated activities, ERK1/2 activation (Lillehoj et al., 2004) and IL-8 biosynthesis (Shanks et al., 2010), each was elicited (FIGS. 4F, 4G). Infection of airway ECs with Ad-NEU1 increased the binding of Alexa Fluor 594-labeled flagellin compared with Ad-GFP-infected controls (FIG. 4H). Scatchard transformation of the binding data revealed a 2.9-fold reduction in the dissociation constant ($K_d$) for flagellin binding to Ad-NEU1-infected ECs ($K_d$=2.54 nM) compared with Ad-GFP-infected ECs ($K_d$=7.35 nM) (FIG. 4I). However, the numbers of flagellin binding sites on the ECs infected with the two Ad constructs, as revealed by their x-axis intercepts, were comparable (Ad-NEU1, 158,000 sites/EC; Ad-GFP, 168,000 sites/EC). These data indicate that flagellin is the Pa adhesin that participates in NEU1-responsive Pa adhesion to and invasion of MUC1-expressing ECs, and that NEU1 promotes flagellin binding to the ECs through increased binding affinity of its receptor, MUC1-ED, but not increased receptor number. Although the binding affinity of monomeric flagellin for airway ECs was clearly increased by NEU1 expression, the magnitude of this effect with Pa flagella is likely greater than that measured here given the polyvalent binding interactions between the multimeric Pa flagellum and the multiple tandem repeats of MUC1-ED.

Flagellin Stimulates NEU1 Recruitment to MUC1.

Figure 5:
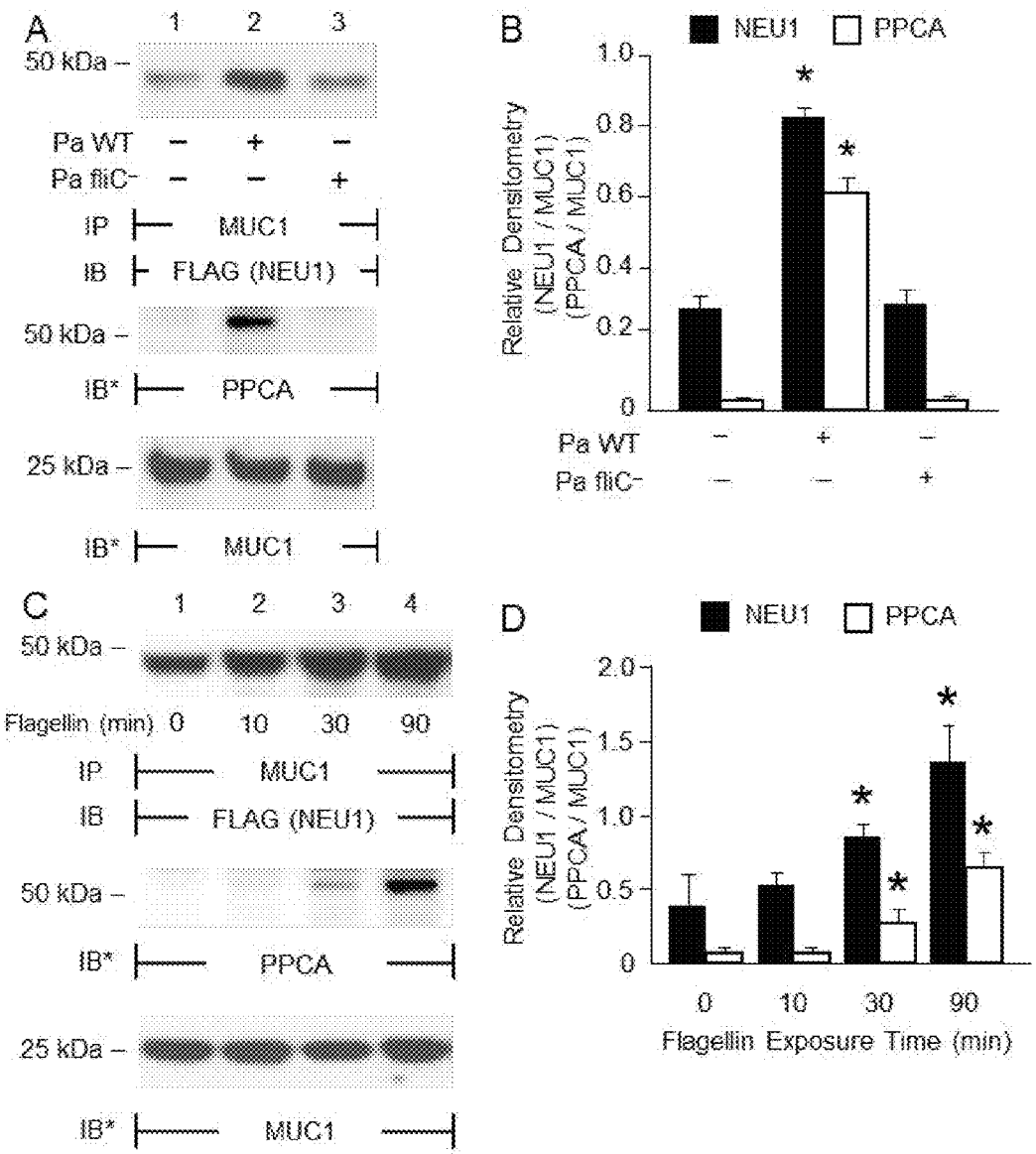
FIG. 5. Flagellin Increases NEU1 Recruitment to MUC1.
Figure 5:
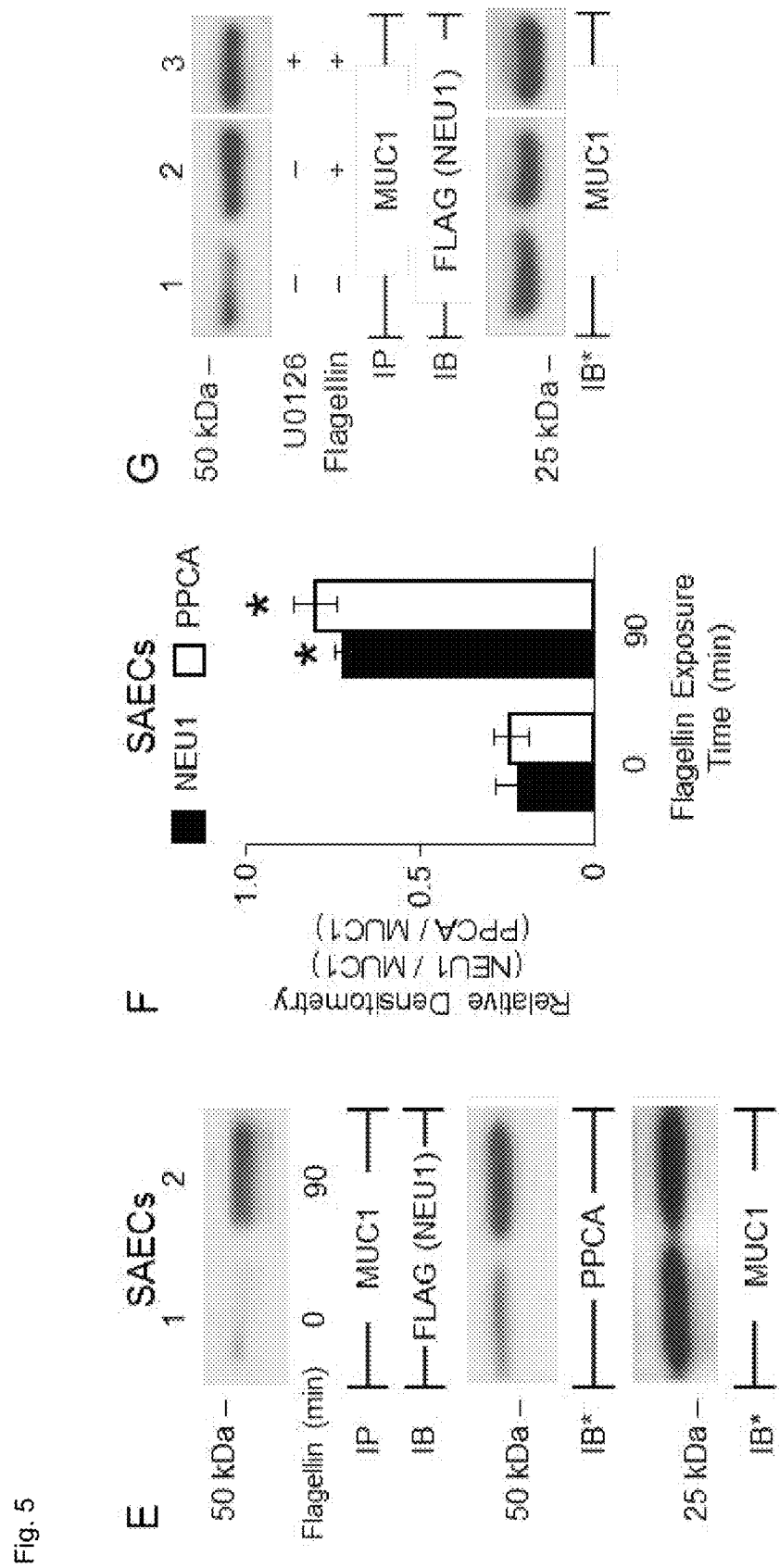

Forced NEU1 overexpression increases adhesion of flagellin-expressing Pa to airway ECs (FIGS. 3B, 3D, 3E, 3G, 4A). It was asked whether engagement of MUC1-ED by Pa flagellin upregulates NEU1 expression and/or catalytic activity. Flagellin stimulation of airway ECs failed to alter NEU1 mRNA or protein levels, or catalytic activity for the fluorogenic substrate, 4-MU-NANA, compared with the simultaneous medium controls (data not shown). Further, increases in NEU1 expression or activity in airway ECs under proinflammatory or injurious conditions that might be elicited in response to invasive Pa infection were not detected (data not shown). Therefore, it was asked whether flagellin induces recruitment of a preformed pool of NEU1 to MUC1. Incubation of airway ECs with flagellin-expressing Pa, but not with the Pa fliC⁻ mutant, increased MUC1-NEU1 co-immunoprecipitation compared with the simultaneous medium controls (FIGS. 5A, upper panel, 5B). Flagellin-expressing Pa also stimulated MUC1-PPCA association compared with Pa fliC⁻ (FIGS. 5A, middle panel, 5B). In A549 cells (FIGS. 5C, 5D) and primary SAECs (FIGS. 5E, 5F), flagellin increased MUC1-NEU1 (FIGS. 5C, 5E, upper panels, 5D, 5F) and MUC1-PPCA (FIGS. 5C, 5E, middle panels, 5D, 5F) association compared with the medium controls. Since flagellin increases ERK1/2 activation (FIG. 4F, lane 2) temporally coincident with MUC1-NEU1 association (FIGS. 5C-5F) (Lillehoj et al., 2004), it was asked whether MUC1-NEU1 association requires ERK1/2 activation. Preincubation of airway ECs with an inhibitory concentration of the MEK1/2 inhibitor, U0126 (FIG. 4F, lane 4), failed to alter MUC1-NEU1 co-immunoprecipitation (FIG. 5G). These data indicate that flagellin stimulates the recruitment of a preformed pool of NEU1, accompanied by PPCA, to MUC1 in an ERK1/2-independent manner.

Flagellin Increases NEU1-Dependent MUC1-ED Desialylation, Pa Adhesion, and Invasion.

Figure 6:
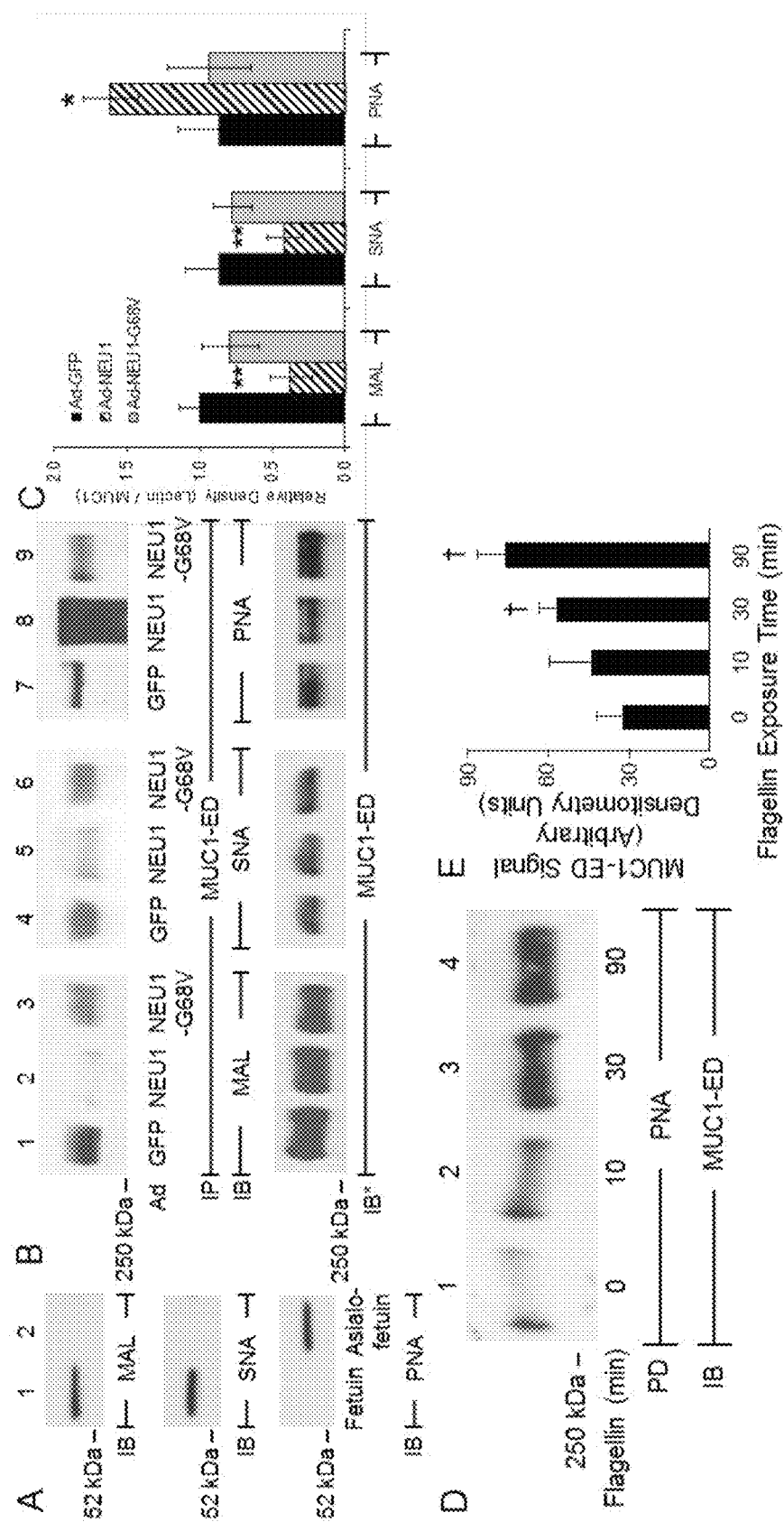
FIG. 6. Flagellin Increases NEU1-Dependent MUC1-ED Desialylation.
Figure 6:
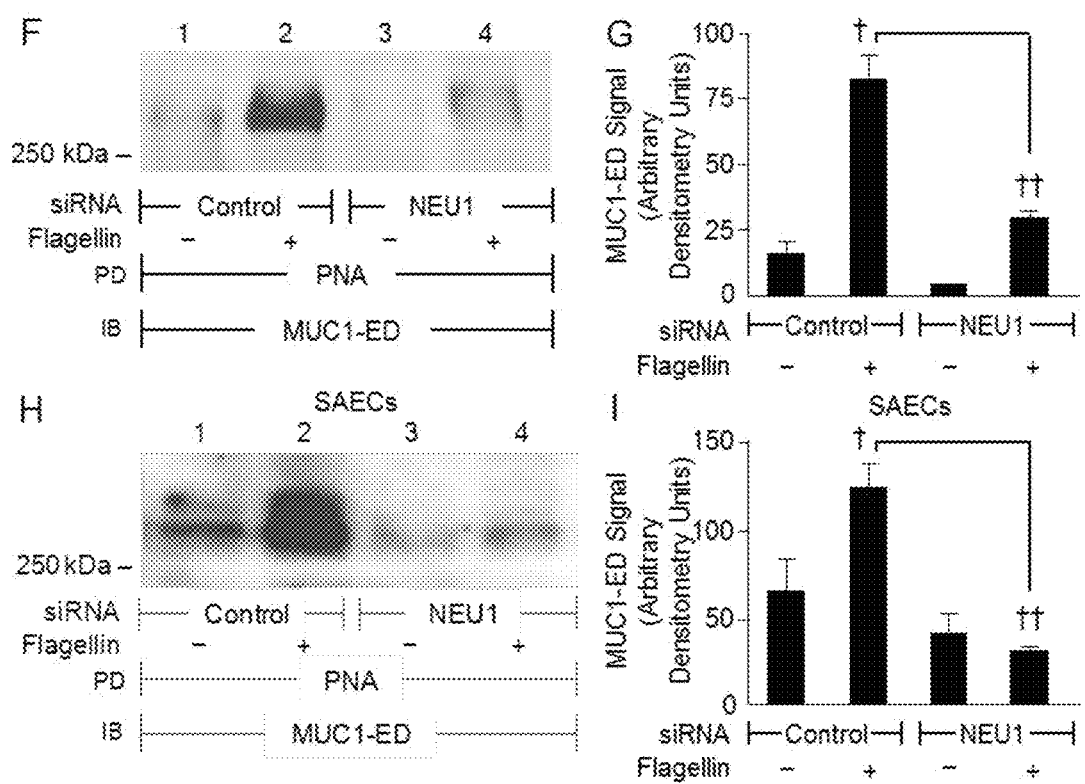
Figure 7:
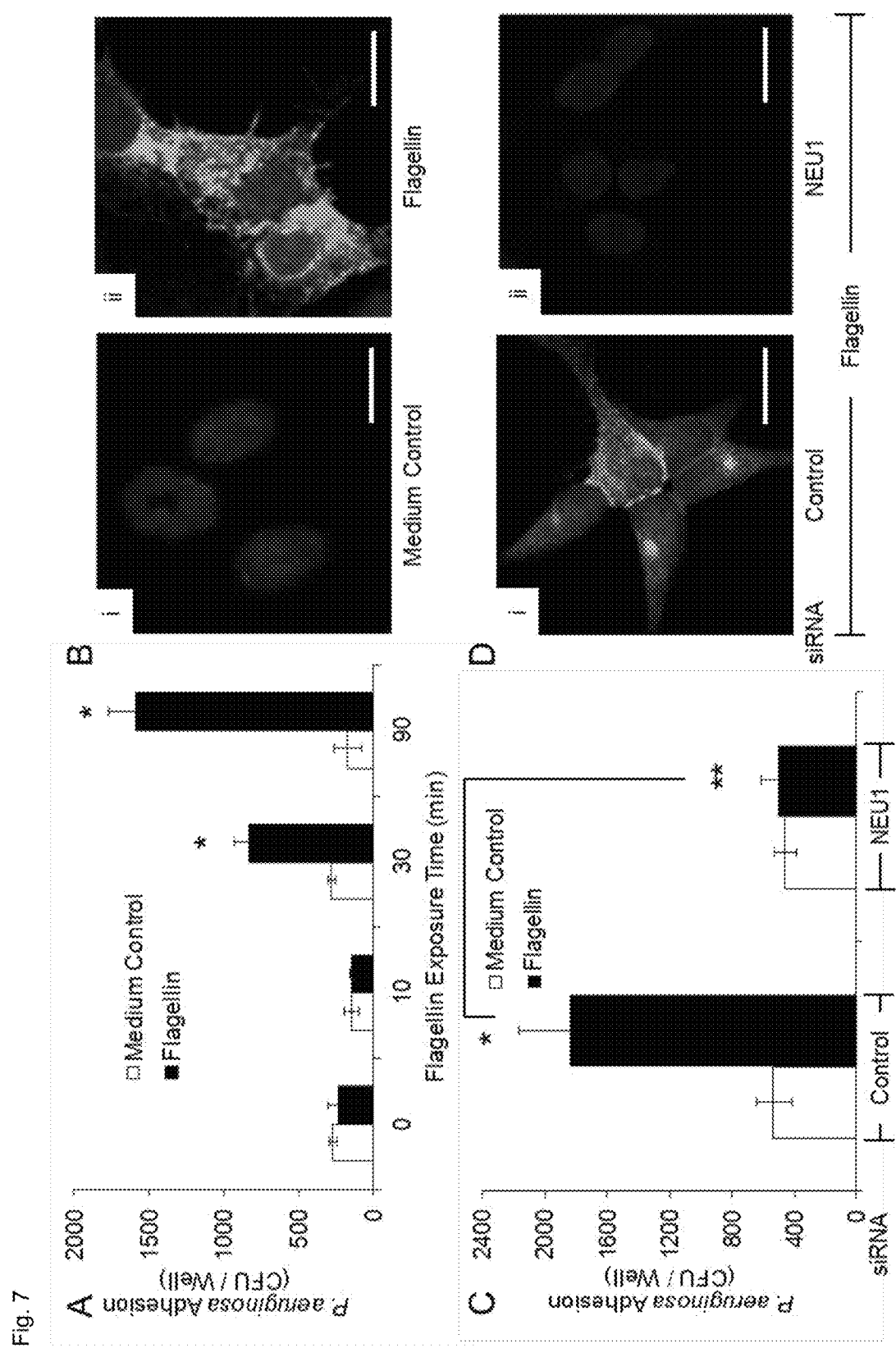
FIG. 7. NEU1 is Required for Flagellin-Induced Increases in Pa Adhesion and Invasion.
Figure 7:
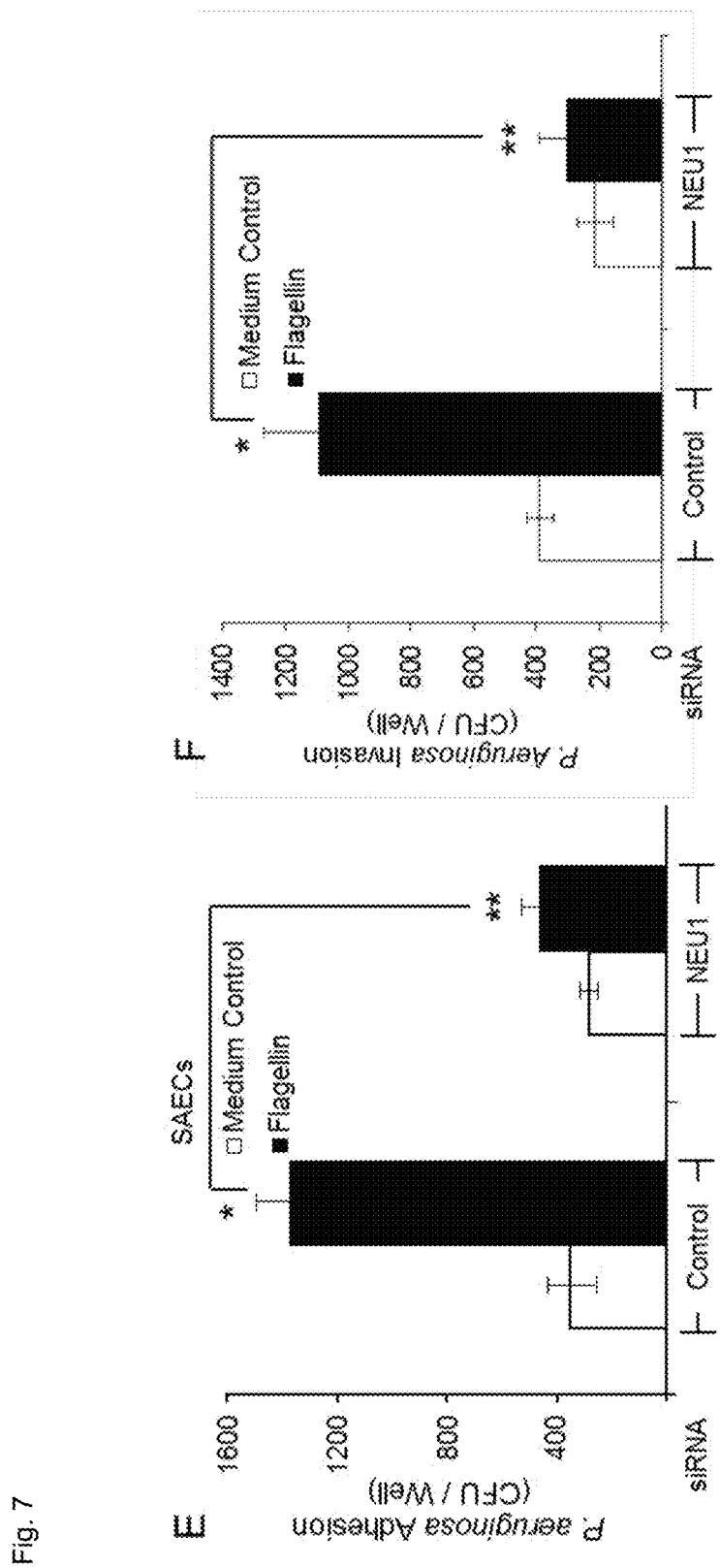

Since NEU1 overexpression increases MUC1 adhesiveness for Pa (FIGS. 3B, 3D, 3E, 3G, 4A, 4C) and its flagellin (FIGS. 4H, 4I), it was next determined whether MUC1-ED is a NEU1 substrate. Infection of airway ECs with Ad-NEU1 diminished the binding of MUC1-ED with *Maackia amurensis* lectin II (MAL) and *Sambucus nigra* agglutinin (SNA), which recognize α2,3- and α2,6-linked SA residues, respectively, compared with Ad-GFP-infected (FIG. 6B, lanes 2 vs. 1, lanes 5 vs. 4, 6C) and Ad-NEU1-G68V-infected ECs (FIG. 6B, lanes 2 vs. 3, lanes 5 vs. 6, 6C). Conversely, NEU1 overexpression increased the binding of MUC1-ED with peanut agglutinin (PNA) which recognizes subterminal galactose after removal of terminal Sia, compared with Ad-GFP-infected (FIG. 6B, lanes 8 vs. 7, 6C) and Ad-NEU1-G68V-infected ECs (FIG. 6B, lanes 8 vs. 9, 6C). Since flagellin promotes MUC1-NEU1 association (FIGS. 5A-5G) and NEU1 overexpression desialylates MUC1-ED (FIGS. 6B, 6C), it was asked whether flagellin increases NEU1-mediated MUC1-ED desialylation. Incubation of airway ECs for 30 or 90 min with flagellin enhanced PNA binding to MUC1-ED compared with medium alone (FIGS. 6D, 6E). NEU1 knockdown (FIG. 3H) protected against flagellin-stimulated MUC1-ED desialylation in A549 cells (FIG. 6F, lanes 4 vs. 2, 6G) and SAECs (FIG. 6H, lanes 4 vs. 2, 6I) compared with control siRNA-transfected ECs. Since flagellin increases NEU1-mediated MUC1-ED desialylation (FIGS. 6D-6I), it was asked whether flagellin increases Pa adhesion to and invasion of airway ECs. Flagellin stimulation of airway ECs increased Pa adhesion compared with medium alone (FIGS. 7A, 7B). NEU1 silencing protected against flagellin-enhanced Pa adhesion compared with control siRNA-transfected A549 cells (FIGS. 7C, 7D) and SAECs (FIG. 7E). Stimulation of airway ECs with flagellin increased Pa invasion in a NEU1-dependent manner compared with controls (FIG. 7F). These results indicate that 1) in its endogenous state, MUC1-ED contains α2,3- and α2,6-linked SA as well as subterminal galactose, 2) overexpression of catalytically-active NEU1 desialylates MUC1-ED, and 3) flagellin increases NEU1-dependent MUC1-ED desialylation and Pa adhesion to and invasion of airway ECs.

Flagellin Increases NEU1-Dependent MUC1-ED Shedding.

MUC1-ED is shed from the EC surface following proteolytic cleavage (Lillehoj et al., 2013). NEU1 overexpression (FIGS. 6B, 6C) and flagellin stimulation (FIGS. 6D-6I) each desialylate the MUC1-ED. Since SA residues can mask protease recognition sites (Bachert and Linstedt, 2012), it was asked whether these same experimental conditions that promote MUC1-ED desialylation also increase its shedding. NEU1 overexpression (FIGS. 8A-8C), and flagellin stimulation of A549 cells (FIGS. 8D, 8F, 8G) and SAECs (FIG. 8E), each dose-dependently increased shedding of desialylated MUC1-ED into airway EC culture supernates compared with Ad-GFP-infected ECs and medium controls, respectively. NEU1 silencing abolished both flagellin-induced MUC1-ED desialylation (FIGS. 6F-6I) and increases in MUC1-ED shedding (FIGS. 8D, 8E) compared with control siRNA transfection. Therefore, the identical experimental conditions that promote NEU1-mediated MUC1-ED desialylation also provoke its shedding.

MUC1-ED Levels are Higher in Human Bronchoalveolar Lavage Fluids (BALFs) from Pa-Colonized Patients.

Figure 8:
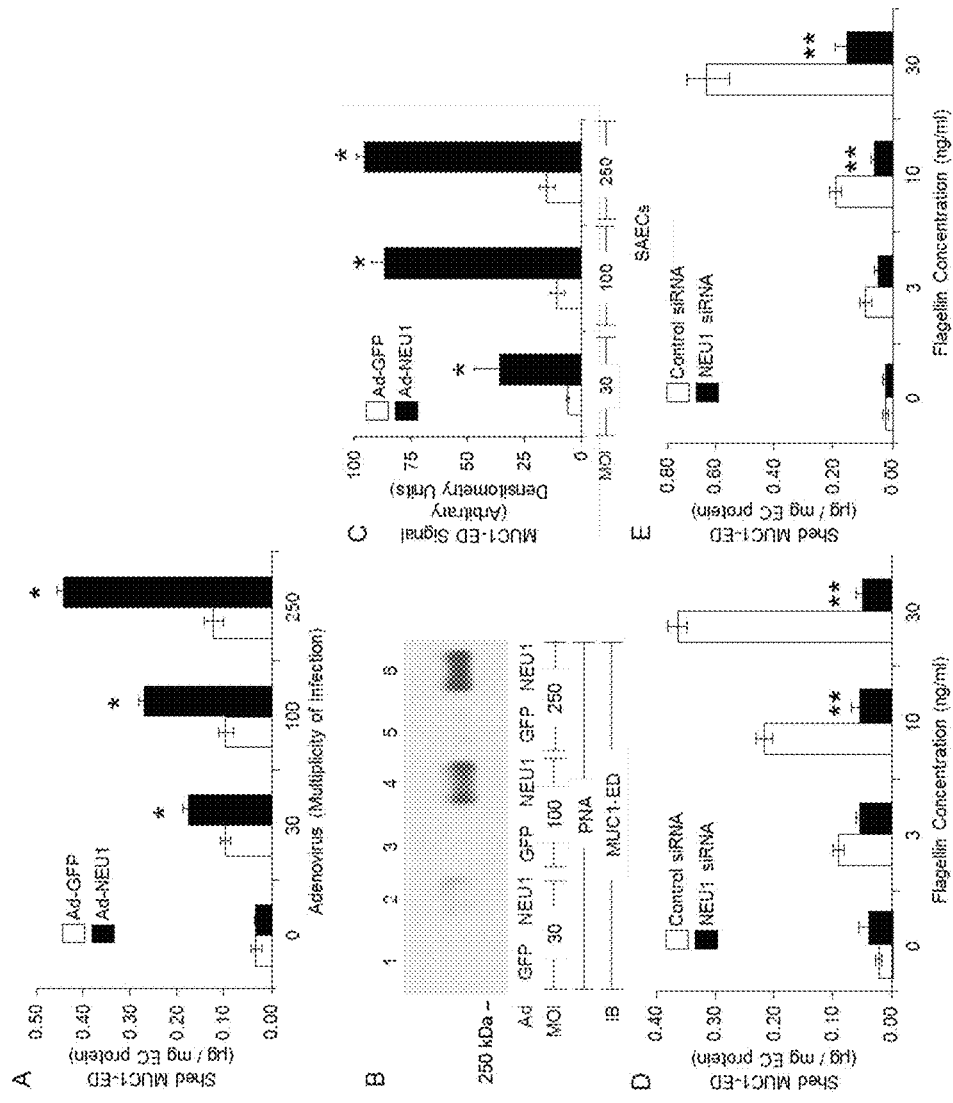
FIG. 8. Flagellin Stimulates NEU1-Dependent MUC1-ED Shedding.
Figure 8:
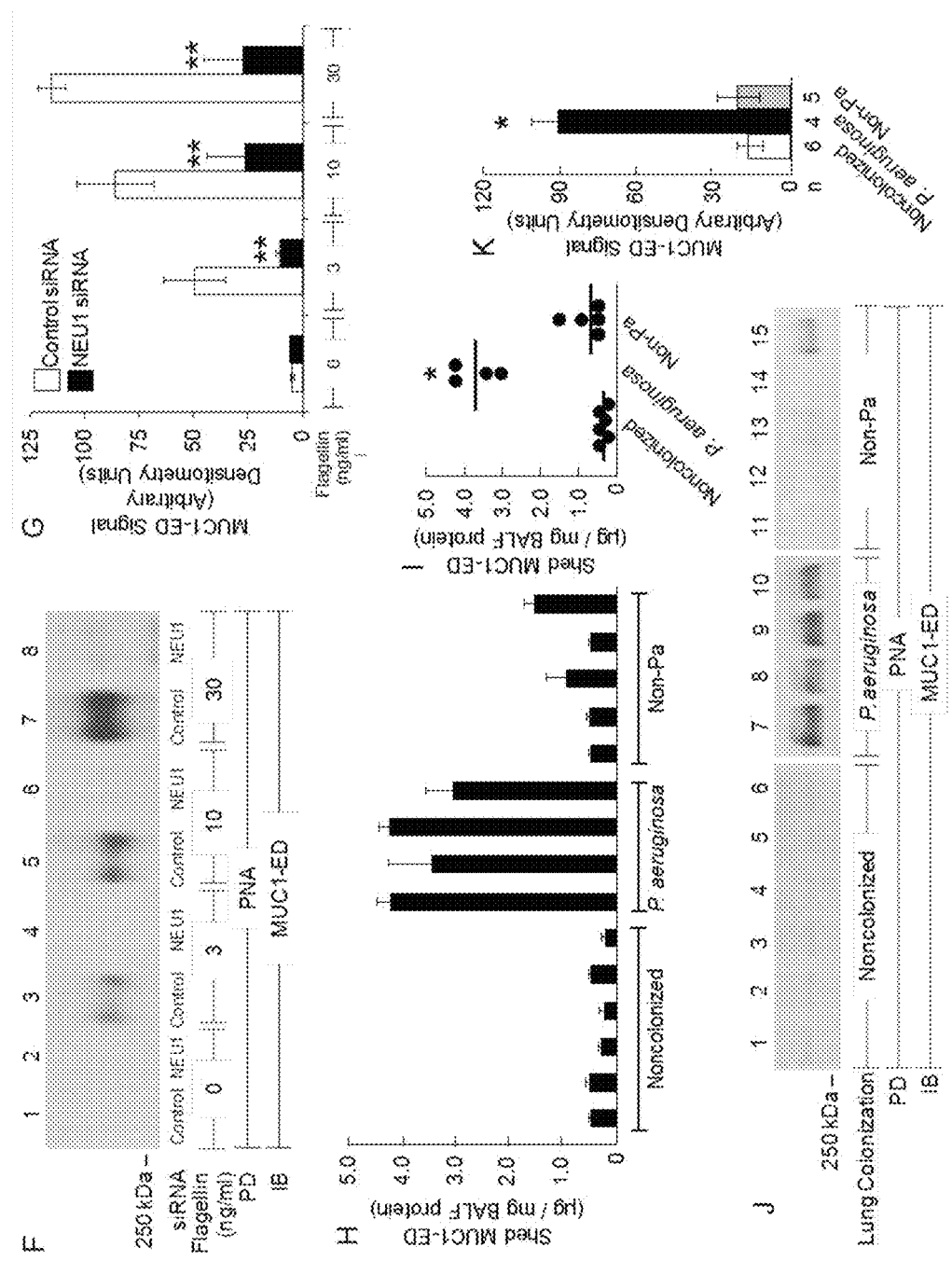

Since Pa flagellin increases both MUC1-ED desialylation (FIGS. 6D-6I) and its shedding (FIGS. 8D, 8E), it was asked whether MUC1-ED levels are increased in BALFs from patients with Pa airway colonization. MUC1-ED levels were quantified by ELISA and normalized to total BALF protein, which ranged from 69 to 101 µg/ml. MUC1-ED levels were 9.9-fold higher in BALFs from Pa-colonized patients compared with levels in BALFs from noncolonized subjects, and 5.5-fold greater compared with levels in BALFs from patients colonized with nonPa microorganisms (*Staphylococcus aureus, Klebsiella pneumoniae, Klebsiella oxytoca, Proteus mirabilis*, or *Candida albicans*) (FIGS. 8H, 8I). The MUC1-ED in BALFs from Pa-colonized patients was desialylated (FIGS. 8J, 8K). These data indicate that the in vitro results can be extended to in vivo human pathophysiology and that the increased MUC1-ED shedding is specific for Pa airway colonization. Given the dilutional effect inherent to the BAL procedure, these results may underestimate the true levels of MUC1-ED in the BALFs of Pa-colonized patients.

MUC1-ED Shed in Response to Flagellin Inhibits Pa Adhesion to EC-Associated MUC1-ED.

Figure 9:
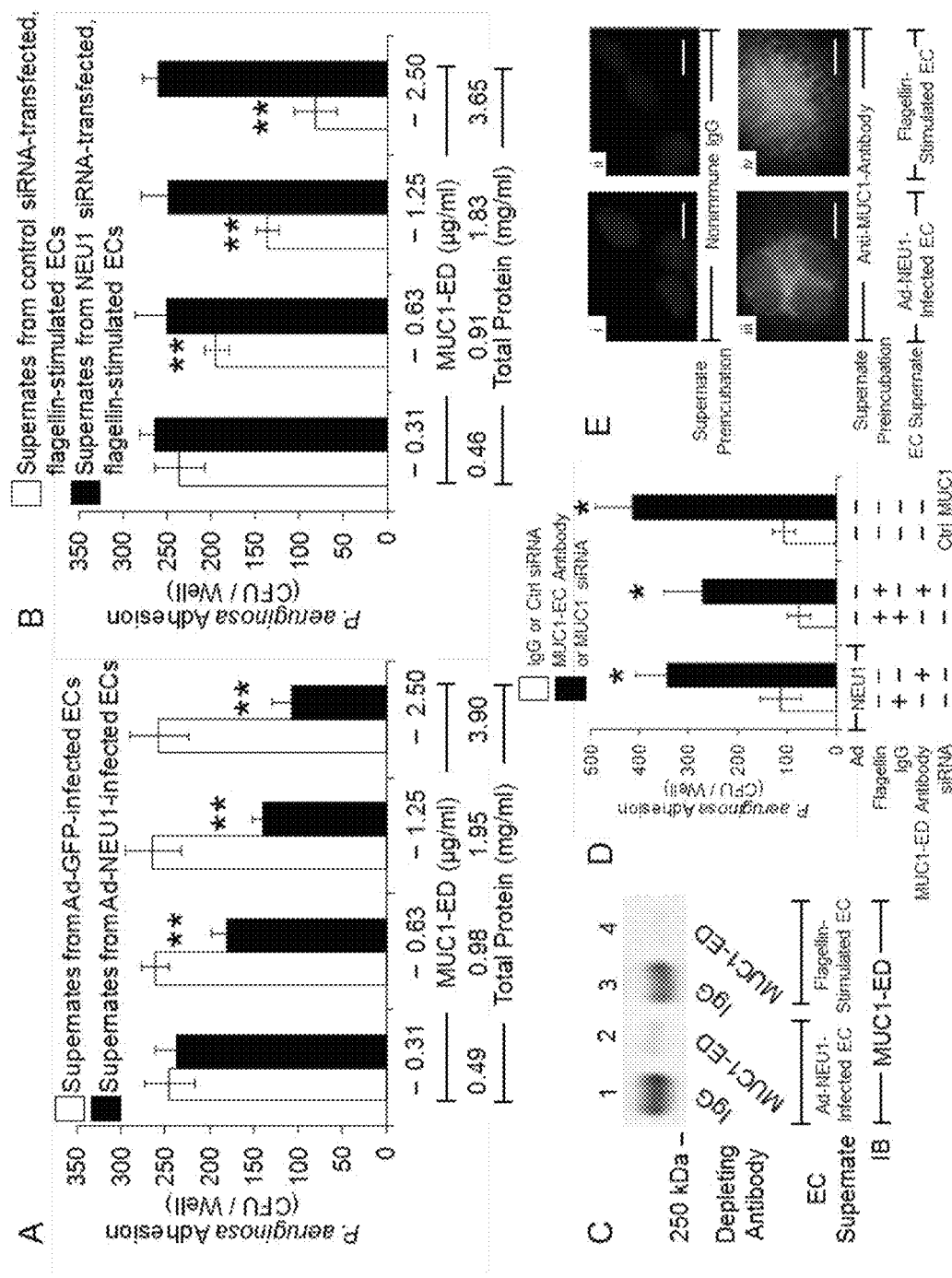
FIG. 9. MUC1-ED Shed in vitro or in vivo Inhibits Pa Adhesion to EC-Associated MUC1-ED.
Figure 9:
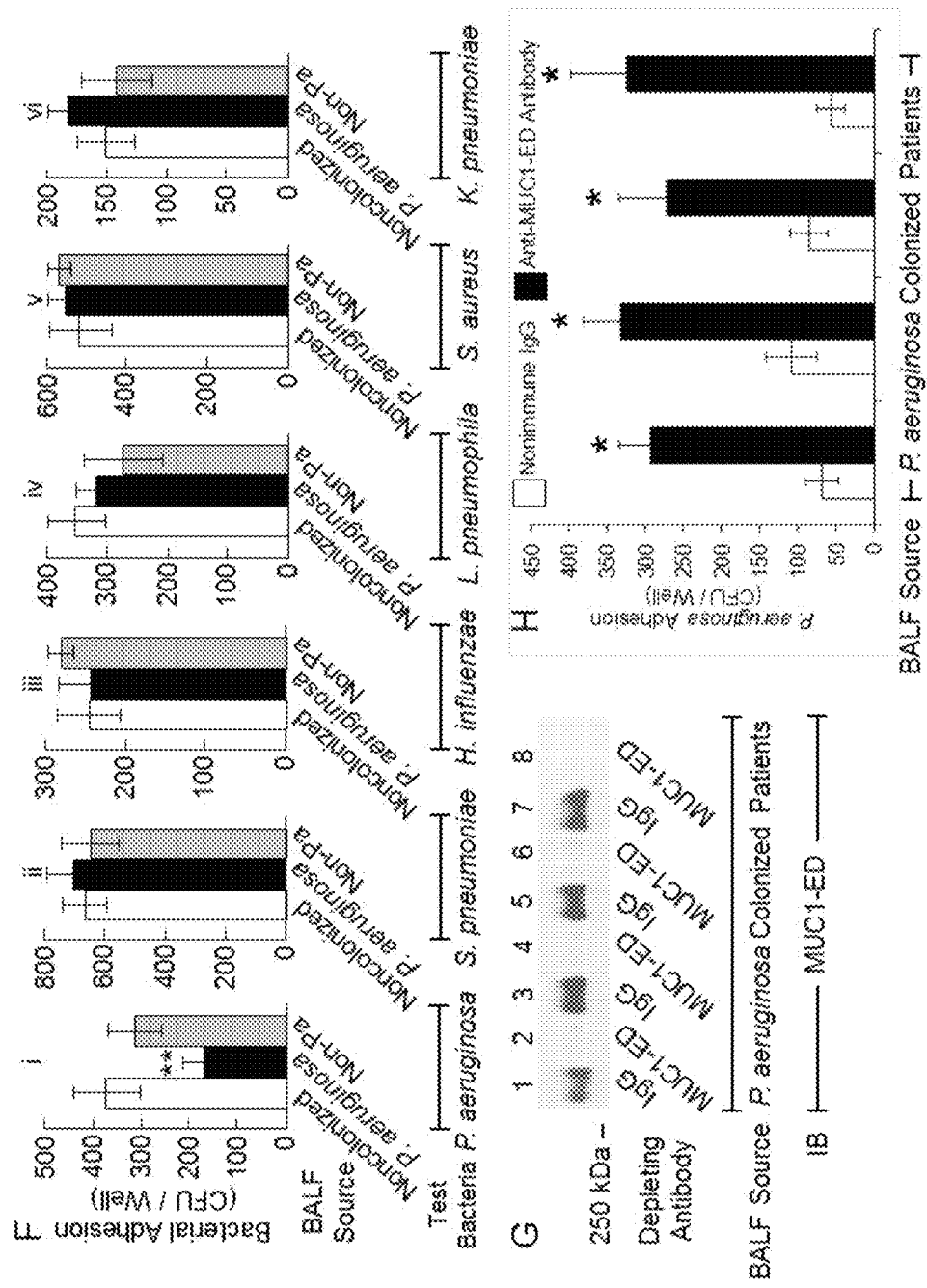
Figure 9:
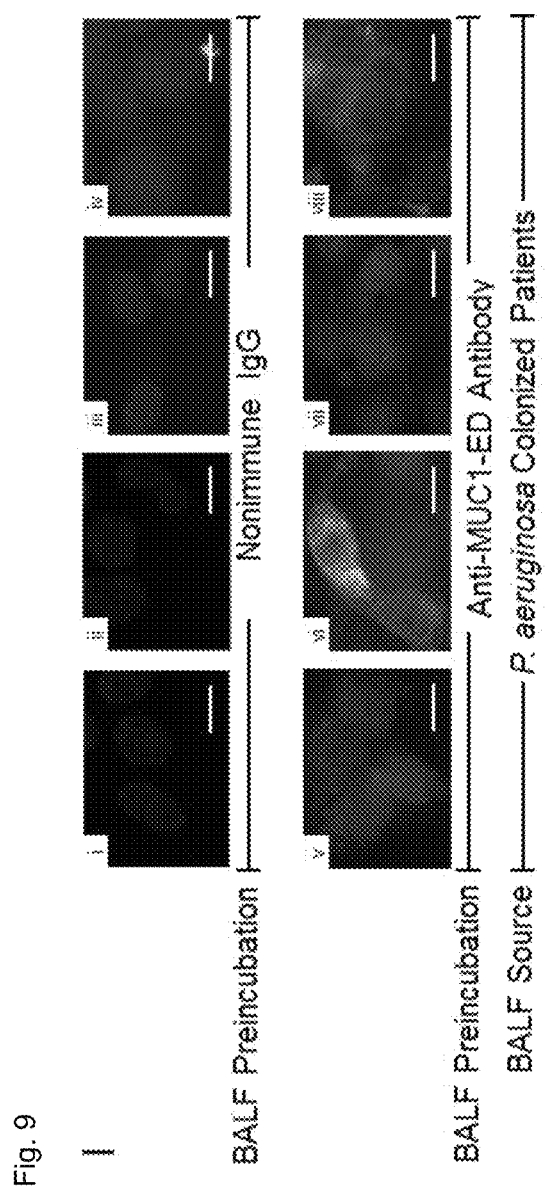

NEU1 renders the MUC1-ED hyperadhesive for Pa (FIGS. 3B, 3D, 3E, 3G, 4A, 4C, 7C-7E), and at the same time, increases MUC1-ED shedding (FIGS. 8A, 8D, 8E). It was asked whether the shed, hyperadhesive MUC1-ED competitively inhibits Pa adhesion to EC-associated MUC1-ED. Preincubation of Pa with supernates of airway ECs infected with Ad-NEU1 dose-dependently reduced bacterial adhesion to fresh EC monolayers, while preincubation of Pa with supernates of ECs infected with Ad-GFP did not (FIG. 9A). Similarly, Pa preincubation with supernates of flagellin-stimulated ECs dose-dependently blocked Pa adhesion (FIG. 9B). However, prior NEU1 silencing abolished the ability of supernates of ECs stimulated with flagellin to reduce Pa adhesion compared with supernates of control siRNA-transfected ECs (FIG. 9B). Preincubation of supernates of either Ad-NEU1-infected ECs, or ECs stimulated by flagellin, with anti-MUC1-ED antibody, immunodepleted the samples of detectable MUC1-ED (FIG. 9C) and dramatically reduced their ability to inhibit Pa adhesion compared with supernates preincubated with the same concentration of a species- and isotype-matched nonimmune IgG (FIGS. 9D, 9E). Transfection of airway ECs with MUC1 siRNA also profoundly diminished the ability of their supernates to inhibit Pa adhesion compared with supernates from control siRNA-transfected ECs (FIG. 9D). These data indicate that MUC1-ED shed in vitro in response to flagellin competitively inhibits Pa adhesion to MUC1-ED-expressing airway ECs.

BALFs from Pa-Colonized Patients Inhibit Pa Adhesion to EC-Associated MUC1-ED.

Since MUC1-ED shed in vitro in response to Pa flagellin inhibits Pa adhesion to EC-associated MUC1-ED (FIGS. 9A, 9B), it was asked whether BALFs from Pa-colonized patients containing increased levels of desialylated MUC1-ED (FIGS. 8H-8K) inhibits bacterial adhesion. Preincubation of Pa with BALFs from Pa-colonized patients inhibited bacterial adhesion to airway ECs by 52.9% compared with preincubation with BALFs from noncolonized subjects and by 42.1% compared with preincubation with BALFs from patients colonized with nonPa microorganisms (FIG. 9F, panel i). Preincubation of the same bacteria tested for NEU1-responsive adhesion (FIG. 3B) with BALFs from Pa-colonized patients failed to inhibit the adhesion of these bacteria compared with preincubation with BALFs from noncolonized subjects or BALFs from patients colonized with nonPa microbes (FIG. 9F, panels ii-vi). Preincubation of BALFs from Pa-colonized patients with anti-MUC1-ED antibody immunodepleted the samples of detectable MUC1-ED (FIG. 9G) and greatly reduced their ability to inhibit Pa adhesion compared with preincubation with the IgG control (FIGS. 9H, 9I). These combined data indicate that MUC1-ED in BALFs from Pa-colonized patients, but not BALFs from patients colonized by nonPa microbes, acts as a soluble decoy receptor that competitively inhibits Pa adhesion to MUC1-ED-expressing airway ECs and that MUC1-ED inhibitory activity for bacterial adhesion is specific for Pa. Since the levels of total protein in the recovered BALFs reached 0.1 mg/ml, and the in vivo concentrations of shed MUC1-ED in BALFs from Pa-colonized subjects, normalized to total protein, reached 4.3 µg/mg (FIGS. 8H, 8I), the levels of MUC1-ED in these same BALFs, up to 0.43 µg/ml, approached those MUC1-ED concentrations capable of inhibiting Pa adhesion in vitro (≤0.63 µg/ml) (FIGS. 9A, 9B). Again, given the dilutional effect inherent to the BAL procedure, combined with the known sequestration of a fraction of MUC1-ED within the bronchoalveolar lining fluid (Ali et al., 2011), these data likely underestimate the true levels of shed MUC1-ED in the BALFs from Pa-colonized patients.

Carbohydrates Subterminal to SA Fail to Inhibit Pa Adhesion to EC-Associated MUC1-ED.

Figure 10:
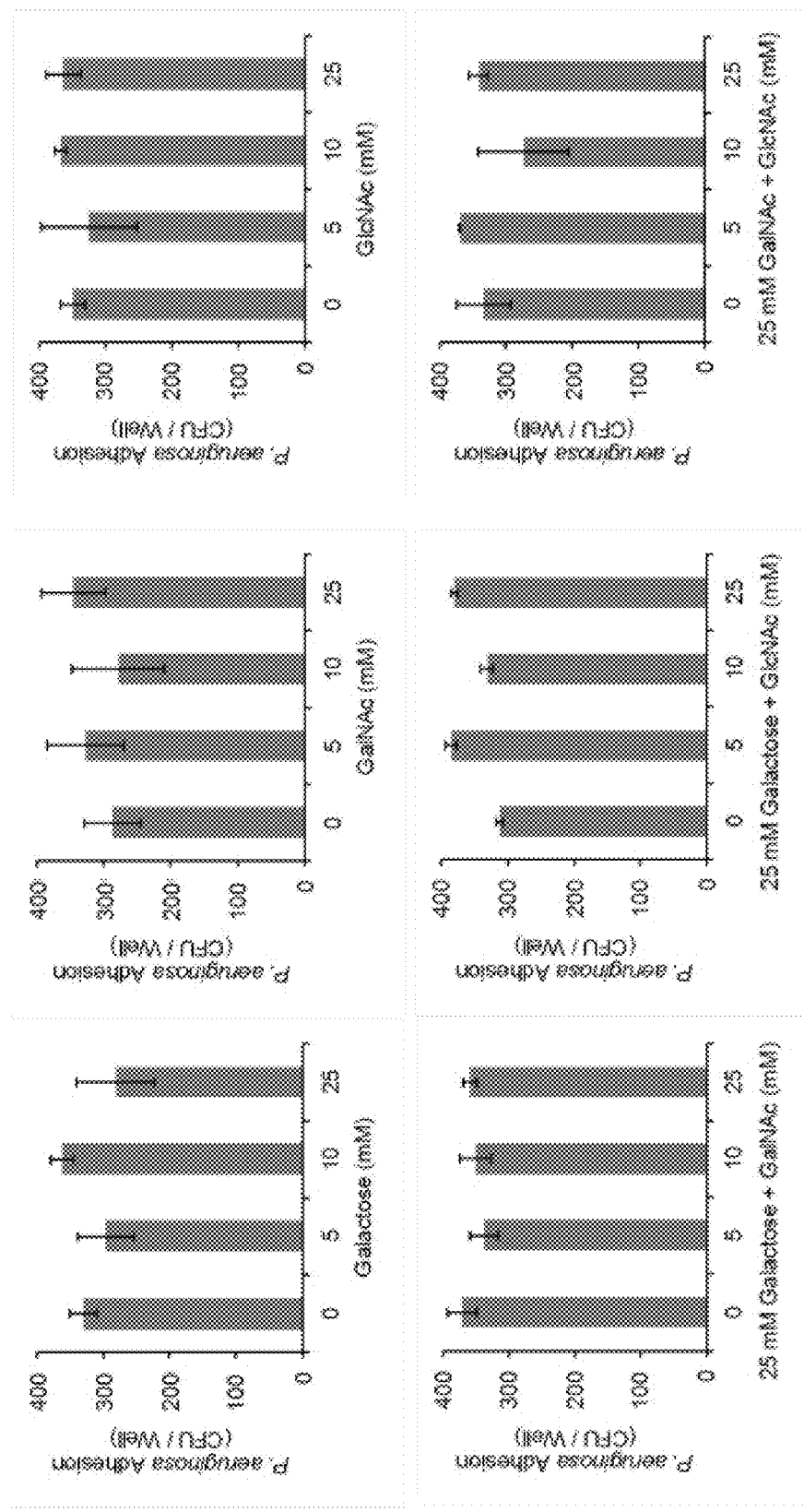
FIG. 10. Role of Glycan Residues in MUC1-ED Inhibition of *P. aeruginosa* Adhesion. Pa were preincubated for 30 min with phosphate buffered saline (PBS) (0 mM) or with 5, 10, or 25 mM of the free monosaccharides galactose, N-acetylgalactosamine (GalNAc), or N-acetylglucosamine (GlcNAc), with a mixture of 25 mM galactose plus 5, 10, or 25 mM GalNAc or GlcNAc, or with a mixture of 25 mM GalNAc plus 5, 10, or 25 mM GlcNAc. Following preincubation, the bacteria were washed and assayed for adhesion to A549 cell monolayers. Vertical bars represent the mean±SEM of CFUs adhered per well (n=3). De-sialylation of MUC1-ED exposes sub-terminal sugar groups on MUC1-ED and enhances MUC1-ED's adhesion inhibitory activity. However, free monosaccharides (corresponding to the sub-terminal sugar groups exposed upon de-sialylation of the glycans on MUC1-ED) do not block Pa adhesion to the EC cells and thus cannot substitute for de-sialylated MUC1-ED itself FIG. 11. Effect of MUC1-ED Desialylation or inhibition of MUC1-ED N-glycosylation and/or O-glycosylation on *P. aeruginosa* Adhesion. Shed MUC1-ED was prepared from supernates of A549 cells infected for 24 h with Ad-GFP or Ad-NEU1 (each at MOI=100), supernates of A549 cells incubated for 24 h in the presence of 40 µg/ml of the N-linked glycosylation inhibitor, tunicamycin, or 5.0 mM of the O-linked glycosylation inhibitor, benzyl-N-acetyl-α-galactosamine (GalNAc-O-bn), or *E. coli* transformed with an empty vector control or a plasmid encoding for MUC1 (pMUC1). Pa were preincubated for 30 min with the different shed MUC1-ED preparations, washed, and assayed for adhesion to fresh A549 monolayers. Vertical bars represent the mean±SEM of CFUs adhered per well (n=3); *p0.05.

Since removal of SA from MUC1-ED enhances Pa adhesion to airway ECs (FIGS. 3B, 3D, 3E, 3G, 3I, 3J, 4A), it was asked whether MUC1-ED glycans immediately subterminal to SA might be required for binding to flagellin-expressing Pa. Pa were preincubated with the glycan residues to which SA is tethered (Lillehoj et al., 2013; Parker et al., 2010), the monosaccharides galactose (Gal), N-acetylgalactosamine (GalNAc), and/or N-acetylglucosamine (GlcNAc), prior to the bacteria being incubated with airway ECs. None of these monosaccharides, either separately or in combination, blocked Pa adhesion to ECs (FIG. 10).

Deglycosylated MUC1-ED Decreases Pa Adhesion to Airway ECs.

Figure 11:
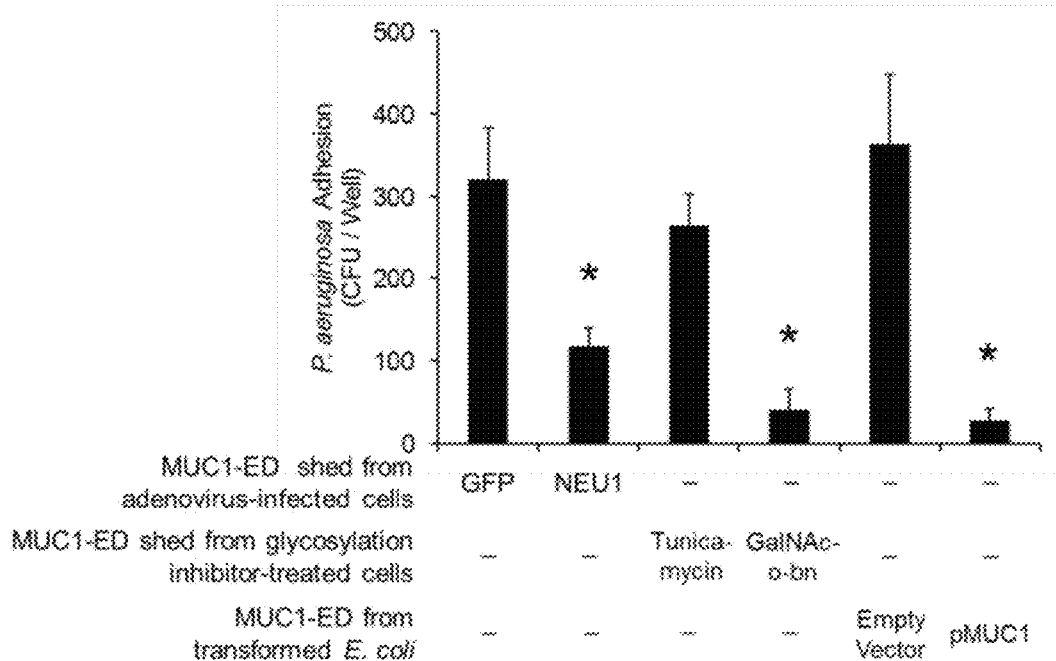

It was next asked whether the decoy receptor activity of MUC1-ED might reside within other sugars of its O-linked and/or N-linked glycans. Here, MUC1-ED was prepared from supernates of airway ECs cultured in the presence of the O-glycosylation inhibitor, benzyl-N-acetyl-α-galactosaminide (GalNAc-O-bn) (Huang et al., 1992) or the N-glycosylation inhibitor, tunicamycin (Duksin and Mahoney, 1982). Since bacteria lack the cellular machinery necessary for robust post-translational glycosylation of eukaryotic proteins (Khow and Suntrarachun, 2012), a deglycosylated form of MUC1-ED was prepared by transformation of *Escherichia coli* with a MUC1 expression plasmid (pMUC1) or the empty vector as a negative control. As a positive control, MUC1-ED was prepared from culture supernates of airway ECs infected with Ad-GFP or Ad-NEU1. Preincubation of Pa with desialylated MUC1-ED from Ad-NEU1-infected ECs reduced adhesion by ~65% vs. Ad-GFP-infected ECs (FIG. 11). Preincubation of Pa with MUC1-ED from GalNAc-O-bn-treated ECs, or from *E. coli* transformed with pMUC1, reduced adhesion by 88% and 93%, respectively, compared with their respective controls (FIG. 11). However, preincubation of Pa with MUC1-ED from tunicamycin-treated ECs did not reduce Pa adhesion (FIG. 11).

A Synthetic uNglycosylated Peptide (GSTAPPAHGVTSAPDTRPAP; SEQ ID NO:1) Corresponding to a Single Repeat from the MUC1-ED Tandem Repeat Region Inhibits Pa Adhesion.

Figure 12:
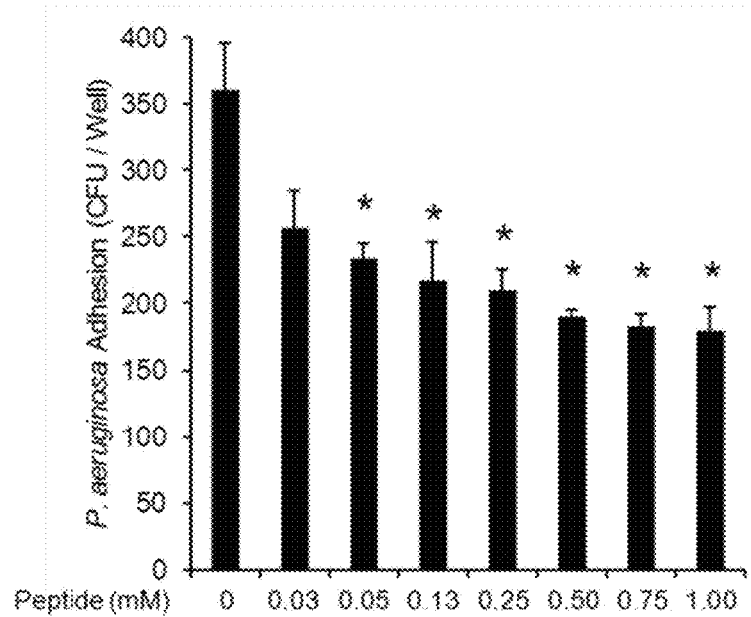
FIG. 12. A Synthetic Unglycosylated Peptide (GSTAPPAHGVTSAPDTRPAP; SEQ ID NO:1) Corresponding to a Single Repeat from the MUC1-ED Tandem Repeat Region Inhibits *P. aeruginosa* Adhesion. Pa were preincubated for 30 min with PBS (0 mM) or with the MUC1-ED synthetic peptide (0.03 mM-1.0 mM). Following preincubation, the bacteria were washed and assayed for adhesion to A549 cell monolayers. Vertical bars represent the mean±SEM of CFUs adhered per well (n=3); *p<0.05.

O-linked carbohydrates of MUC1-ED reside within and outside of the tandem repeat region (Lillehoj et al., 2013). Since removal of O-linked carbohydrates from MUC1-ED enhanced its decoy receptor function (FIG. 11), it was asked whether a synthetic non-glycosylated peptide corresponding to a singe repeat from the tandem repeat region might inhibit Pa adhesion to airway ECs. Pa were preincubated with increasing concentrations of the peptide, GSTAPPAHGVT-SAPDTRPAP (SEQ ID NO:1), prior to the bacteria being incubated with airway ECs. Preincubation of Pa with this peptide dose-dependently decreased bacterial adhesion to the ECs, with a maximum of 50% inhibition achieved with 1.0 mM of peptide (FIG. 12).

E. coli-Expressed MUC1-ED Reduces Pa Lung Infection In Vivo.

Figure 13:
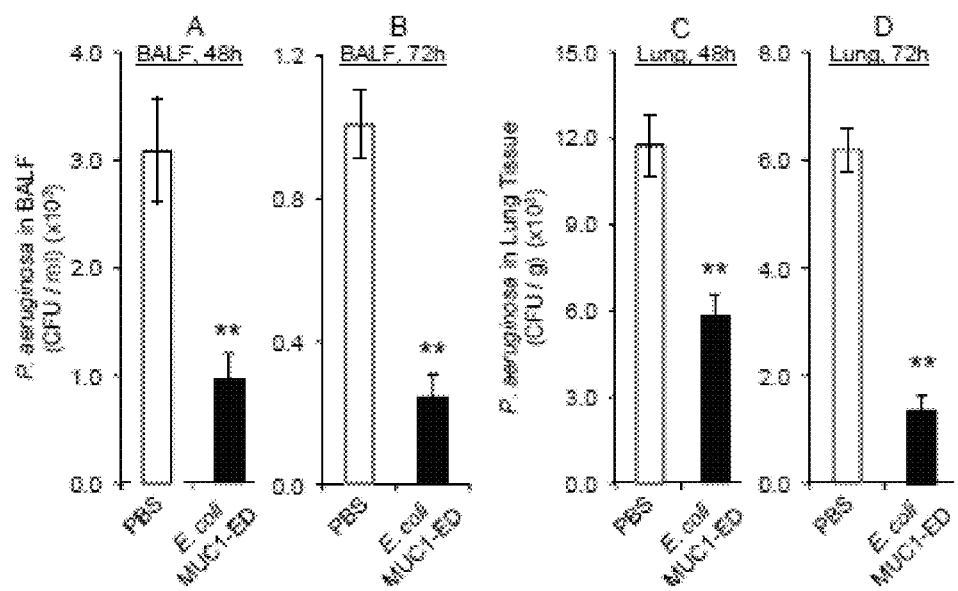
FIGS. 13A-13D. *E. coli*-expressed MUC1-ED Reduces *P. aeruginosa* Lung Infection in vivo.

Since deglycosylated MUC-ED expressed in E. coli reduces Pa adhesion to airway ECs in vitro, it was asked whether E. coli-expressed MUC1-ED might also inhibit Pa lung infection in vivo. Pa were preincubated with E. coli-expressed MUC1-ED, or with PBS as a negative control, and mice were challenged intratracheally (i.t.) with $10^5$ CFU/mouse of the deglycosylated MUC1-ED-Pa or PBS-Pa mixtures. BALF and lung tissues were collected at 48 h and 72 h post-challenge, and Pa CFU were quantified. Preincubation of Pa with deglycosylated MUC1-ED expressed in E. coli reduced the number of Pa recovered from both the BALF (FIGS. 13A, 13B) and lungs (FIGS. 13C, 13D) at 48 h and 72 h post-challenge compared with Pa preincubated with the PBS negative control (FIG. 13).

Discussion

Overexpression of catalytically-active NEU1 in human airway ECs increased their adhesiveness for Pa and L. pneumophila. However, because MUC1 is an established NEU1 substrate (Lillehoj et al., 2012) and Pa adhesion was MUC1-dependent while L. pneumophila adhesion was not, focus was on the mechanism(s) through which NEU1 increases MUC1-dependent Pa adhesion to the EC surface. That the catalytically-inert NEU1 mutant, NEU1-G68V, was incapable of desialylating MUC1-ED, or increasing Pa adhesion to or invasion of airway ECs, indicates that NEU1-responsive Pa adhesion requires NEU1 sialidase activity. Expression of flagellin by Pa was required for NEU1-responsive Pa adhesion and invasion, and the contribution of TLR5 to flagellin-dependent adhesion was negligible. Ad-NEU1 infection of airway ECs increased the binding affinity between flagellin and its receptor, MUC1-ED, as revealed by a 2.9-fold reduction in the dissociation constant for this interaction. In airway ECs, flagellin increased NEU1 recruitment to MUC1, NEU1-dependent desialylation of MUC1-ED, and Pa adhesion to and invasion of airway ECs. Flagellin also increased NEU1-dependent MUC1-ED shedding, and preincubation of Pa with airway EC culture supernates containing shed, desialylated MUC1-ED competitively inhibited Pa adhesion to EC-associated MUC1-ED. MUC1-ED levels were higher in BALFs from Pa-colonized patients compared with levels in BALFs from either noncolonized subjects or from patients colonized with nonPa microorganisms. Pa preincubation with BALFs from Pa-colonized patients blocked Pa adhesion to EC-associated MUC1-ED. This is believed to be the first report demonstrating that Pa uses its flagellin to hijack human NEU1 to increase MUC1-ED-dependent adhesion/invasion, while the host simultaneously uses flagellin-driven MUC1-ED desialylation to generate a shed, hyperadhesive decoy receptor for Pa.

That NEU1 overexpression enhanced airway EC adhesiveness for Pa and its flagellin, and bacterial invasion of these same ECs, suggests that removal of terminal SA residues unmasks a cryptic binding site(s) within MUC1-ED comprised of one or more sugars subterminal to SA and/or its protein backbone. MUC1-ED exhibits a β-turn helix resulting from its high proline content (Fontenot et al., 1995). This extended rod-like conformation allows MUC1-ED to protrude higher than most membrane-associated proteins above the EC surface where it is strategically positioned to interact with Pa in the airway lumen. The degree of MUC1-ED extension into the lumen depends upon the number of tandem repeat units, a genetically inherited allelic polymorphism varying from 20 to 120 repeats (Lillehoj et al., 2013). Whether upon desialylation, MUC1-EDs with more tandem repeats exhibit greater adhesiveness for Pa and/or superior decoy receptor function compared with MUC1-EDs with fewer repeats, or of greater clinical relevance, whether individuals expressing different repeat numbers have altered susceptibility to invasive Pa lung infection, is unknown.

Analysis of the mouse NEU1 gene promoter has identified potential positive and negative cis-acting elements that might regulate NEU1 expression (Champigny et al., 2003). Although flagellin failed to increase NEU1 expression or catalytic activity, it did promote MUC1-NEU1 association. That flagellin promoted this association within 30 min of stimulation likely excludes de novo NEU1 mRNA or protein synthesis as a source for the increased MUC1-associated NEU1. Although lipopolysaccharide (LPS) reportedly promotes NEU1 recruitment to TLR4 (Amith et al., 2010), the fact that the flagellin preparation was preadsorbed with polymyxin B (Lillehoj et al., 2002) diminished the likelihood that LPS contamination of flagellin was responsible for the MUC1-NEU1 association. While it was previously reported that flagellin engagement of MUC1-ED activates ERK1/2 (Lillehoj et al., 2004), NEU1 recruitment to MUC1 through pharmacologic blockade of ERK1/2 activation could not be prevented. It is conceivable that flagellin activates another signaling pathway that promotes the association of preformed NEU1 with MUC1. Since NEU1 exists in a complex with PPCA and β-galactosidase (Bonten and d'Azzo, 2000), MUC1-NEU1 association might be indirectly mediated through either of these, or other, NEU1-binding partners. Alternatively, MUC1-binding partners (e.g. c-src, ErbB1, glycogen synthase kinase 3β, β-catenin) (Lillehoj et al., 2013) might similarly participate in the MUC1-NEU1 interaction.

Pa NanPs might contribute to basal levels of Pa adhesion seen in airway ECs in which NEU1 has been silenced (Lillehoj et al., 2012). However, Pa expression of NanPs has not been associated with increased bacterial adhesion to airway ECs (Soong et al., 2006). In contrast to other bacterial NEUs, which contain a catalytic pocket structurally similar to that of canonical NEUs, crystallographic analysis of NanPs has revealed a more open, atypical structure (Hsiao et al., 2009). It was hypothesize that Pa commandeers the human sialidase, NEU1, to compensate for its structurally and functionally distinct NanPs, to desialylate MUC1-ED and increase Pa adhesion to and invasion of human airway ECs. Manipulation of host-cell pathways by bacteria to enhance their virulence has been recognized as a central tenet of bacterial pathogenesis for several decades (Bhavsar et al., 2007). The results further suggest that the host has responded to Pa hijacking of human NEU1 by releasing desialylated MUC1-ED from the EC surface, which in turn, competitively inhibits interaction between flagellin-expressing Pa and EC-associated MUC1-ED. It is tempting to speculate that the balance between these opposing processes, i.e. Pa adhesiveness vs. decoy receptor function, and how they are impacted by the activities of other NEUs, sialyltransferases, and/or proteases, ultimately dictates the clinical outcome of an individual airway EC exposure to Pa.

Neither Gal, GalNAc, nor GlcNAc were able to competitively inhibit Pa adhesiveness for airway ECs. These results suggest that either other carbohydrates within MUC1-ED, and/or its protein backbone might be responsible for its decoy receptor function. Removal of O-linked carbohydrates from MUC1-ED enhanced its decoy receptor function, and deglycosylated MUC1-ED, prepared by GalNAc-O-bn treatment of ECs or by pMUC1 transformation of *E. coli*, not only retained decoy receptor function, but exceeded that seen with the desialylated MUC1-ED from Ad-NEU1-infected ECs. These results suggest that the decoy receptor function of MUC1-ED might reside within its protein backbone. Further, deglycosylated MUC1-ED prepared in *E. coli* also exhibited decoy receptor function in vivo and the reduced bacterial burden in BALF and lungs using a mouse model of Pa lung infection. Finally, preincubation of Pa with the synthetic peptide GSTAPPAHGVTSAPDTRPAP (SEQ ID NO:1), corresponding to a single repeat from the tandem repeat region of MUC1-ED, dose-dependently inhibited Pa adhesion to airway ECs. These results suggest that the decoy receptor function of MUC1-ED resides within the tandem repeat of its protein backbone. However, maximum inhibition of Pa adhesion using the single repeat synthetic peptide was only 50%, compared with >90% inhibition achieved using the *E. coli*-derived MUC1-ED containing 15 repeats. These results suggest that increased decoy receptor function might be obtained with head-to-tail multimers of the single repeat (i.e. tandem repeat MUC1 decoy peptides).

Example 2

Effect of *E. coli* MUC1-ED With or Without Cefepime on Mouse Survival Following *Pseudomonas aeruginosa* Lung Infection.

*P. aeruginosa* was administered intranasally to groups of seven BALB/c mice at an $LD_{90}$ ($2.0 \times 10^7$ CFU/mouse). The control group (group #1) received PBS intraperitoneally as therapy; group #2 received MUC1-ED (2.5 µg/mouse) intraperitoneally; group #3 received cefepime (1.0 µg/mouse) intraperitoneally; group #4 received MUC1-ED (2.5 µg/mouse) and cefepime (1.0 µg/mouse) simultaneously, intraperitoneally. The MUC1-ED was *E. coli*-expressed deglycosylated peptide having the amino acid sequence set forth in SEQ ID NO:2.

Figure 14:
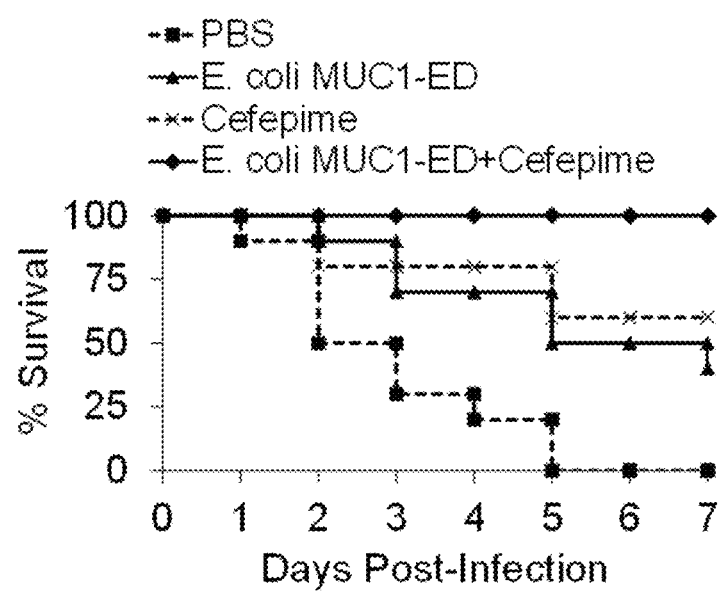
FIG. 14. Effect of *E. coli* MUC1-ED With or Without Cefepime on Mouse Survival Following *Pseudomonas aeruginosa* Lung Infection. *Pseudomonas aeruginosa* was administered intranasally to BALB/c mice at an $LD_{90}$ (2.0× $10^7$ CFU/mouse) with PBS control or *E. coli*-expressed MUC1-ED (2.5 μg/mouse). Simultaneously, PBS or cefepime (1.0 μg/mouse) was administered intraperitoneally, and mouse survival was measured daily (n=7/group).

Mouse survival was measured daily and the results are shown in FIG. 14. As can be seen, there was 100% survival over seven days in mice receiving both MUC1-ED decoy peptide and cefepime (group #4), in contrast to mice receiving MUC1-ED decoy peptide alone (~45% survival; group #2) or cefepime alone (~62.5% survival; group #3).

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

Ali, M., Lillehoj, E. P., Park, Y., Kyo, Y., and Kim, K. C. (2011). Analysis of the proteome of human airway epithelial secretions. Proteome Sci. 9, 4.

Amith, S. R., Jayanth P., Franchuk, S., Finlay, T., Seyrantepe, V., Beyaert, R., Pshezhetsky, A. V., and Szewczuk, M. R. (2010). Neu1 desialylation of sialyl α-2,3-linked β-galactosyl residues of TOLL-like receptor 4 is essential for receptor activation and cellular signaling. Cell. Signal. 22, 314-324.

Bachert, C., and Linstedt, A. D. (2012). A sensor of protein O-glycosylation based on sequential processing in the Golgi apparatus. Traffic 14, 47-56.

Bhavsar, A. P, Guttman, J. A., and Finlay, B. B. (2007). Manipulation of host-cell pathways by bacterial pathogens. Nature 449, 827-834.

Bonten, E. J., and d'Azzo, A. (2000). Lysosomal neuraminidase. Catalytic activation in insect cells is controlled by the protective protein/cathepsin A. J. Biol. Chem. 275, 37657-37663.

Brewer, S. C., Wunderink, R. G., Jones, C. B., and Leeper, K. V. J. (1996). Ventilator-associated pneumonia due to *Pseudomonas aeruginosa*. Chest 109, 1019-1029.

Champigny, M. J., Johnson, M., and Igdoura, S. A. (2003). Characterization of the mouse lysosomal sialidase promoter. Gene 319, 177-187.

Duksin, D. and Mahoney, W. C., (1982). Relationship of the structure and biological activity of the natural homologues of tunicamycin. J. Biol. Chem. 257, 3105-3109.

Fontenot, J. D., Mariappan, S. V. S., Catasti, P., Domenech, N., Finn, O. J., and Gupta, G. (1995). Structure of a tumor associated antigen containing a tandemly repeated immunodominant epitope. J. Biomol. Struct. Dynam. 13, 245-260.

Hsiao, Y. S., Parker, D., Ratner, A. J., Prince, A., and Tong, L. (2009). Crystal structures of respiratory pathogen neuraminidases. Biochem. Biophys. Res. Commun. 380, 467-471.

Huang, J., Byrd, J. C., Yoon, W. H., and Kim, Y. S. (1992). Effect of benzyl-α-GalNAc, an inhibitor of mucin glycosylation, on cancer-associated antigens in human colon cancer cells. Oncol. Res. 4, 507-515.

Khow, O. and Suntrarachun, S. (2012). Strategies for production of active eukaryotic proteins in bacterial expression system. Asian Pac. J. Trop. Biomed. 2, 159-162.

Kim, K. C., Zheng, Q. X., Wilson, A. K., Lee, B. C., and Berman, J. S. (1994). Binding kinetics of $ATP_\gamma S^{35}$ on cultured primary tracheal surface epithelial cells. Am. J. Respir. Cell Mol. Biol. 10, 154-159.

Lee, C., Liu, A., Miranda-Ribera, A., Hyun, S. W., Lillehoj, E. P., Cross, A. S., Passaniti, A., Grimm, P. R., Kim, B. Y., Welling, P. A., Madri, J. A., Delisser, H. M., and Goldblum, S. E. (2014). NEU1 sialidase regulates the sialylation state of CD31 and disrupts CD31-driven capillary-like tube formation in human lung microvascular endothelia. J. Biol. Chem. 289, 9121-9135

Lewis, A. L. and Lewis, W. G. (2012) Host sialoglycans and bacterial sialidases: a mucosal perspective. Cell. Microbiol. 14, 1174-1182.

Lillehoj, E. P., Kim, B. T., and Kim, K. C. (2002). Identification of *Pseudomonas aeruginosa* flagellin as an adhesin for Muc1 mucin. Am. J. Physiol. Lung Cell. Mol. Physiol. 282, L751-L756.

Lillehoj, E. P., Kim, H., Chun, E. Y., and Kim, K. C. (2004). *Pseudomonas aeruginosa* stimulates phosphorylation of the airway epithelial membrane glycoprotein Muc1 and activates MAP kinase. Am. J. Physiol. Lung Cell. Mol. Physiol. 287, L809-L815.

Lillehoj, E. P., Hyun, S. W., Feng, C., Zhang, L., Liu, A., Guang, W., Nguyen, C., Luzina, I. G., Atamas, S. P., Passaniti, A., Twaddell, W. S., Puché, A. C., Wang, L. X., Cross, A. S., and Goldblum, S. E. (2012). NEU1 sialidase expressed in human airway epithelia regulates epidermal growth factor receptor (EGFR) and MUC1 protein signaling. J. Biol. Chem. 287, 8214-8231.

Lillehoj, E. P., Kato, K., Lu, W., and Kim, K. C. (2013). Cellular and molecular biology of airway mucins. Int. Rev. Cell. Mol. Biol. 303, 139-202.

Luzina, I. G., Todd, N. W., Nacu, N., Lockatell, V., Choi, J., Hummers, L. K., and Atamas, S. P. (2009). Regulation of pulmonary inflammation and fibrosis through expression of integrins αVβ3 and αVβ5 on pulmonary T lymphocytes. Arthritis Rheum. 60, 1530-1539.

Mizel, S. B. and Bates, J. T. (2010). Flagellin as an adjuvant: cellular mechanisms and potential. J. Immunol. 185, 5677-5682.

Novosad, S. A and Barker, A. F. (2012). Chronic obstructive pulmonary disease and bronchiectasis. Curr. Opin. Pulm. Med. 19, 133-139.

Parker, P., Sando, L., Pearson, R., Kongsuwan, K., Tellam, R. L., and Smith, S. (2010). Bovine Muc1 inhibits binding of enteric bacteria to Caco-2 cells. Glycoconj. J. 27, 89-97.

Pier, G. B. and Ramphal, R. (2010) *Pseudomonas aeruginosa*. In: Mandell, Douglas and Bennett's Principles and Practice of Infectious Diseases, 6$^{th}$ ed., Mandell, G. L., Bennett, J. E., and Dolin, R. (eds.), Elsevier/Churchill/Livingstone, Philadelphia, Pa., pp 2835-2860.

Prince, A. (1992). Adhesins and receptors of *Pseudomonas aeruginosa* associated with infection of the respiratory tract. Microb. Pathog. 13, 251-260.

Pshezhetsky, A. V. and Ashmarina, L. I. (2013). Desialylation of surface receptors as a new dimension in cell signaling. Biochemistry (Mosc). 78, 736-745.

Ramos, H. C., Rumbo, M., and Sirard, J. C. (2004). Bacterial flagellins: mediators of pathogenicity and host immune responses in mucosa. Trends Microbiol. 12, 509-517.

Schauer, R. (2009). Sialic acids as regulators of molecular and cellular interactions. Curr. Opin. Struct. Biol. 19, 507-514.

Shanks, K. K., Guang, W., Kim, K. C., and Lillehoj, E. P. (2010). Interleukin-8 production by human airway epithelial cells in response to *Pseudomonas aeruginosa* clinical isolates expressing type a or type b flagellins. Clin. Vaccine Immunol. 17, 1196-1202.

Soong, G., Muir, A., Gomez, M. I., Waks, J., Reddy, B., Planet, P., Singh, P. K., Kaneko, Y., Wolfgang, M. C., Hsiao, Y. S., Tong, L., and Prince, A. (2006). Bacterial neuraminidase facilitates mucosal infection by participating in biofilm production. J. Clin. Invest. 116, 2297-2305.

What is claimed is:

1. A method of treating or preventing a pulmonary infection caused by *Pseudomonas aeruginosa* in a subject, comprising administering to the subject a therapeutically effective amount of an ectodomain MUC1 decoy peptide comprising the amino acid sequence set forth in SEQ ID NO:3.

2. The method of claim 1, wherein the pulmonary infection is treated.

3. The method of claim 1, wherein the pulmonary infection is an infection of the lungs of a subject with cystic fibrosis or a ventilator-associated pneumonia.

4. The method of claim 1, wherein the ectodomain MUC1 decoy peptide is formulated in a pharmaceutical formulation comprising the peptide and a pharmaceutically acceptable carrier or diluent.

5. The method of claim 1 further comprising administering a therapeutically effective amount of one or more antibiotics to the subject.

6. The method of claim 5, wherein the one or more antibiotics are formulated in a pharmaceutical formulation comprising the antibiotic and a pharmaceutically acceptable carrier or diluent.

7. The method of claim 5 wherein the ectodomain MUC1 decoy peptide comprises the amino acid sequence set forth in SEQ ID NO:3 the antibiotic is cefepime.

8. The method of claim 5 wherein the ectodomain MUC1 decoy peptide and the one or more antibiotics are administered to the subject via separate administrations.

9. The method of claim 1, wherein the administering comprises administering by inhalation.

* * * * *

```
                           SEQUENCE LISTING

<160> NUMBER OF SEQ ID NOS: 7

<210> SEQ ID NO 1
<211> LENGTH: 20
<212> TYPE: PRT
<213> ORGANISM: Homo sapiens

<400> SEQUENCE: 1

Gly Ser Thr Ala Pro Pro Ala His Gly Val Thr Ser Ala Pro Asp Thr
1               5                   10                  15

Arg Pro Ala Pro
            20

<210> SEQ ID NO 2
<211> LENGTH: 397
<212> TYPE: PRT
<213> ORGANISM: Artificial Sequence
<220> FEATURE:
<223> OTHER INFORMATION: ectodomain MUC1 decoy peptide

<400> SEQUENCE: 2

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
```

```
            100                 105                 110
Pro Pro Ala His Asp Val Thr Ser Ala Pro Asp Asn Lys Pro Ala Pro
            115                 120                 125
Gly Ser Thr Ala Pro Ala His Gly Val Thr Ser Ala Pro Asp Thr
            130                 135                 140
Arg Pro Ala Pro Gly Ser Thr Ala Pro Pro Ala His Gly Val Thr Ser
145                 150                 155                 160
Ala Pro Asp Thr Arg Pro Ala Pro Gly Ser Thr Ala Pro Pro Ala His
            165                 170                 175
Gly Val Thr Ser Ala Pro Asp Thr Arg Pro Ala Pro Gly Ser Thr Ala
            180                 185                 190
Pro Pro Ala His Gly Val Thr Ser Ala Pro Asp Thr Arg Pro Ala Pro
            195                 200                 205
Gly Ser Thr Ala Pro Pro Ala His Gly Val Thr Ser Ala Pro Asp Thr
            210                 215                 220
Arg Pro Ala Pro Gly Ser Thr Ala Pro Pro Ala His Gly Val Thr Ser
225                 230                 235                 240
Ala Pro Asp Asn Arg Pro Ala Leu Gly Ser Thr Ala Pro Pro Val His
            245                 250                 255
Asn Val Thr Ser Ala Ser Gly Ser Ala Ser Gly Ser Ala Ser Thr Leu
            260                 265                 270
Val His Asn Gly Thr Ser Ala Arg Ala Thr Thr Thr Pro Ala Ser Lys
            275                 280                 285
Ser Thr Pro Phe Ser Ile Pro Ser His His Ser Asp Thr Pro Thr Thr
            290                 295                 300
Leu Ala Ser His Ser Thr Lys Thr Asp Ala Ser Ser Thr His His Ser
305                 310                 315                 320
Thr Val Pro Pro Leu Thr Ser Ser Asn His Ser Thr Ser Pro Gln Leu
            325                 330                 335
Ser Thr Gly Val Ser Phe Phe Phe Leu Ser Phe His Ile Ser Asn Leu
            340                 345                 350
Gln Phe Asn Ser Ser Leu Glu Asp Pro Ser Thr Asp Tyr Tyr Gln Glu
            355                 360                 365
Leu Gln Arg Asp Ile Ser Glu Met Phe Leu Gln Ile Tyr Lys Gln Gly
            370                 375                 380
Gly Phe Leu Gly Leu Ser Asn Ile Lys Phe Arg Pro Gly
385                 390                 395

<210> SEQ ID NO 3
<211> LENGTH: 597
<212> TYPE: PRT
<213> ORGANISM: Artificial Sequence
<220> FEATURE:
<223> OTHER INFORMATION: ectodomain MUC1 decoy peptide

<400> SEQUENCE: 3

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
            35                  40                  45

Thr Glu Lys Asn Ala Val Ser Met Thr Ser Ser Val Leu Ser Ser His
            50                  55                  60

Ser Pro Gly Ser Gly Ser Ser Thr Thr Gln Gly Gln Asp Val Thr Leu
```

-continued

```
                65                  70                  75                  80
Ala Pro Ala Thr Glu Pro Ala Ser Gly Ser Ala Ala Thr Trp Gly Gln
                    85                  90                  95

Asp Val Thr Ser Val Pro Val Thr Arg Pro Ala Leu Gly Ser Thr Thr
                    100                 105                 110

Pro Pro Ala His Asp Val Thr Ser Ala Pro Asp Asn Lys Pro Ala Pro
                    115                 120                 125

Gly Ser Thr Ala Pro Pro Ala His Gly Val Thr Ser Ala Pro Asp Thr
                    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                    165                 170                 175

Gly Val Thr Ser Ala Pro Asp Thr Arg Pro Ala Pro Gly Ser Thr Ala
                    180                 185                 190

Pro Pro Ala His Gly Val Thr Ser Ala Pro Asp Thr Arg Pro Ala Pro
                    195                 200                 205

Gly Ser Thr Ala Pro Pro Ala His Gly Val Thr Ser Ala Pro Asp Thr
                    210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                    245                 250                 255

Gly Val Thr Ser Ala Pro Asp Thr Arg Pro Ala Pro Gly Ser Thr Ala
                    260                 265                 270

Pro Pro Ala His Gly Val Thr Ser Ala Pro Asp Thr Arg Pro Ala Pro
                    275                 280                 285

Gly Ser Thr Ala Pro Pro Ala His Gly Val Thr Ser Ala Pro Asp Thr
                    290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                    325                 330                 335

Gly Val Thr Ser Ala Pro Asp Thr Arg Pro Ala Pro Gly Ser Thr Ala
                    340                 345                 350

Pro Pro Ala His Gly Val Thr Ser Ala Pro Asp Thr Arg Pro Ala Pro
                    355                 360                 365

Gly Ser Thr Ala Pro Pro Ala His Gly Val Thr Ser Ala Pro Asp Thr
                    370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                    405                 410                 415

Gly Val Thr Ser Ala Pro Asp Thr Arg Pro Ala Pro Gly Ser Thr Ala
                    420                 425                 430

Pro Pro Ala His Gly Val Thr Ser Ala Pro Asp Asn Arg Pro Ala Leu
                    435                 440                 445

Gly Ser Thr Ala Pro Pro Val His Asn Val Thr Ala Ser Gly Ser
                    450                 455                 460

Ala Ser Gly Ser Ala Ser Thr Leu Val His Asn Gly Thr Ser Ala Arg
465                 470                 475                 480

Ala Thr Thr Thr Pro Ala Ser Lys Ser Thr Pro Phe Ser Ile Pro Ser
                    485                 490                 495
```

His His Ser Asp Thr Pro Thr Thr Leu Ala Ser His Ser Thr Lys Thr
                500                 505                 510

Asp Ala Ser Ser Thr His His Ser Thr Val Pro Pro Leu Thr Ser Ser
            515                 520                 525

Asn His Ser Thr Ser Pro Gln Leu Ser Thr Gly Val Ser Phe Phe Phe
        530                 535                 540

Leu Ser Phe His Ile Ser Asn Leu Gln Phe Asn Ser Ser Leu Glu Asp
545                 550                 555                 560

Pro Ser Thr Asp Tyr Tyr Gln Glu Leu Gln Arg Asp Ile Ser Glu Met
                565                 570                 575

Phe Leu Gln Ile Tyr Lys Gln Gly Gly Phe Leu Gly Leu Ser Asn Ile
            580                 585                 590

Lys Phe Arg Pro Gly
        595

<210> SEQ ID NO 4
<211> LENGTH: 1255
<212> TYPE: PRT
<213> ORGANISM: Homo sapiens

<400> SEQUENCE: 4

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
                20                  25                  30

Gly Glu Lys Glu Thr Ser Ala Thr Gln Arg Ser Ser Val Pro Ser Ser
            35                  40                  45

Thr Glu Lys Asn Ala Val Ser Met Thr Ser Ser Val Leu Ser Ser His
        50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala

```
            260                 265                 270
Pro Pro Ala His Gly Val Thr Ser Ala Pro Asp Thr Arg Pro Ala Pro
            275                 280                 285
Gly Ser Thr Ala Pro Pro Ala His Gly Val Thr Ser Ala Pro Asp Thr
            290                 295                 300
Arg Pro Ala Pro Gly Ser Thr Ala Pro Pro Ala His Gly Val Thr Ser
305                 310                 315                 320
Ala Pro Asp Thr Arg Pro Ala Pro Gly Ser Thr Ala Pro Pro Ala His
            325                 330                 335
Gly Val Thr Ser Ala Pro Asp Thr Arg Pro Ala Pro Gly Ser Thr Ala
            340                 345                 350
Pro Pro Ala His Gly Val Thr Ser Ala Pro Asp Thr Arg Pro Ala Pro
            355                 360                 365
Gly Ser Thr Ala Pro Pro Ala His Gly Val Thr Ser Ala Pro Asp Thr
            370                 375                 380
Arg Pro Ala Pro Gly Ser Thr Ala Pro Pro Ala His Gly Val Thr Ser
385                 390                 395                 400
Ala Pro Asp Thr Arg Pro Ala Pro Gly Ser Thr Ala Pro Pro Ala His
            405                 410                 415
Gly Val Thr Ser Ala Pro Asp Thr Arg Pro Ala Pro Gly Ser Thr Ala
            420                 425                 430
Pro Pro Ala His Gly Val Thr Ser Ala Pro Asp Thr Arg Pro Ala Pro
            435                 440                 445
Gly Ser Thr Ala Pro Pro Ala His Gly Val Thr Ser Ala Pro Asp Thr
            450                 455                 460
Arg Pro Ala Pro Gly Ser Thr Ala Pro Pro Ala His Gly Val Thr Ser
465                 470                 475                 480
Ala Pro Asp Thr Arg Pro Ala Pro Gly Ser Thr Ala Pro Pro Ala His
            485                 490                 495
Gly Val Thr Ser Ala Pro Asp Thr Arg Pro Ala Pro Gly Ser Thr Ala
            500                 505                 510
Pro Pro Ala His Gly Val Thr Ser Ala Pro Asp Thr Arg Pro Ala Pro
            515                 520                 525
Gly Ser Thr Ala Pro Pro Ala His Gly Val Thr Ser Ala Pro Asp Thr
            530                 535                 540
Arg Pro Ala Pro Gly Ser Thr Ala Pro Pro Ala His Gly Val Thr Ser
545                 550                 555                 560
Ala Pro Asp Thr Arg Pro Ala Pro Gly Ser Thr Ala Pro Pro Ala His
            565                 570                 575
Gly Val Thr Ser Ala Pro Asp Thr Arg Pro Ala Pro Gly Ser Thr Ala
            580                 585                 590
Pro Pro Ala His Gly Val Thr Ser Ala Pro Asp Thr Arg Pro Ala Pro
            595                 600                 605
Gly Ser Thr Ala Pro Pro Ala His Gly Val Thr Ser Ala Pro Asp Thr
            610                 615                 620
Arg Pro Ala Pro Gly Ser Thr Ala Pro Pro Ala His Gly Val Thr Ser
625                 630                 635                 640
Ala Pro Asp Thr Arg Pro Ala Pro Gly Ser Thr Ala Pro Pro Ala His
            645                 650                 655
Gly Val Thr Ser Ala Pro Asp Thr Arg Pro Ala Pro Gly Ser Thr Ala
            660                 665                 670
Pro Pro Ala His Gly Val Thr Ser Ala Pro Asp Thr Arg Pro Ala Pro
            675                 680                 685
```

Gly Ser Thr Ala Pro Pro Ala His Gly Val Thr Ser Ala Pro Asp Thr
690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
            725                 730                 735

Gly Val Thr Ser Ala Pro Asp Thr Arg Pro Ala Pro Gly Ser Thr Ala
            740                 745                 750

Pro Pro Ala His Gly Val Thr Ser Ala Pro Asp Thr Arg Pro Ala Pro
        755                 760                 765

Gly Ser Thr Ala Pro Pro Ala His Gly Val Thr Ser Ala Pro Asp Thr
770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
            805                 810                 815

Gly Val Thr Ser Ala Pro Asp Thr Arg Pro Ala Pro Gly Ser Thr Ala
            820                 825                 830

Pro Pro Ala His Gly Val Thr Ser Ala Pro Asp Thr Arg Pro Ala Pro
        835                 840                 845

Gly Ser Thr Ala Pro Pro Ala His Gly Val Thr Ser Ala Pro Asp Thr
850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
            885                 890                 895

Gly Val Thr Ser Ala Pro Asp Thr Arg Pro Ala Pro Gly Ser Thr Ala
            900                 905                 910

Pro Pro Ala His Gly Val Thr Ser Ala Pro Asp Thr Arg Pro Ala Pro
        915                 920                 925

Gly Ser Thr Ala Pro Pro Ala His Gly Val Thr Ser Ala Pro Asp Asn
930                 935                 940

Arg Pro Ala Leu Gly Ser Thr Ala Pro Val His Asn Val Thr Ser
945                 950                 955                 960

Ala Ser Gly Ser Ala Ser Gly Ser Ala Ser Thr Leu Val His Asn Gly
            965                 970                 975

Thr Ser Ala Arg Ala Thr Thr Thr Pro Ala Ser Lys Ser Thr Pro Phe
            980                 985                 990

Ser Ile Pro Ser His His Ser Asp Thr Pro Thr Thr Leu Ala Ser His
            995                 1000                1005

Ser Thr Lys Thr Asp Ala Ser Ser Thr His His Ser Ser Val Pro
        1010                1015                1020

Pro Leu Thr Ser Ser Asn His Ser Thr Ser Pro Gln Leu Ser Thr
        1025                1030                1035

Gly Val Ser Phe Phe Phe Leu Ser Phe His Ile Ser Asn Leu Gln
        1040                1045                1050

Phe Asn Ser Ser Leu Glu Asp Pro Ser Thr Asp Tyr Tyr Gln Glu
        1055                1060                1065

Leu Gln Arg Asp Ile Ser Glu Met Phe Leu Gln Ile Tyr Lys Gln
        1070                1075                1080

Gly Gly Phe Leu Gly Leu Ser Asn Ile Lys Phe Arg Pro Gly Ser
        1085                1090                1095

-continued

Val Val Val Gln Leu Thr Leu Ala Phe Arg Glu Gly Thr Ile Asn
1100                1105                1110

Val His Asp Val Glu Thr Gln Phe Asn Gln Tyr Lys Thr Glu Ala
1115                1120                1125

Ala Ser Arg Tyr Asn Leu Thr Ile Ser Asp Val Ser Val Ser Asp
1130                1135                1140

Val Pro Phe Pro Phe Ser Ala Gln Ser Gly Ala Gly Val Pro Gly
1145                1150                1155

Trp Gly Ile Ala Leu Leu Val Leu Val Cys Val Leu Val Ala Leu
1160                1165                1170

Ala Ile Val Tyr Leu Ile Ala Leu Ala Val Cys Gln Cys Arg Arg
1175                1180                1185

Lys Asn Tyr Gly Gln Leu Asp Ile Phe Pro Ala Arg Asp Thr Tyr
1190                1195                1200

His Pro Met Ser Glu Tyr Pro Thr Tyr His Thr His Gly Arg Tyr
1205                1210                1215

Val Pro Pro Ser Ser Thr Asp Arg Ser Pro Tyr Glu Lys Val Ser
1220                1225                1230

Ala Gly Asn Gly Gly Ser Ser Leu Ser Tyr Thr Asn Pro Ala Val
1235                1240                1245

Ala Ala Thr Ser Ala Asn Leu
1250                1255

<210> SEQ ID NO 5
<211> LENGTH: 128
<212> TYPE: PRT
<213> ORGANISM: Homo sapiens

<400> SEQUENCE: 5

Met Thr Pro Gly Thr Gln Ser Pro Phe Phe Leu Leu Leu Leu Thr
1               5                   10                  15

Val Leu Thr Val Val Thr Gly Ser Gly His Ala Ser Thr Pro Gly
                20                  25                  30

Gly Glu Lys Glu Thr Ser Ala Thr Gln Arg Ser Ser Val Pro Ser Ser
            35                  40                  45

Thr Glu Lys Asn Ala Val Ser Met Thr Ser Ser Val Leu Ser Ser His
        50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

<210> SEQ ID NO 6
<211> LENGTH: 169
<212> TYPE: PRT
<213> ORGANISM: Homo sapiens

<400> SEQUENCE: 6

Gly Ser Thr Ala Pro Pro Ala His Gly Val Thr Ser Ala Pro Asp Asn
1               5                   10                  15

Arg Pro Ala Leu Gly Ser Thr Ala Pro Pro Val His Asn Val Thr Ser
                20                  25                  30

```
Ala Ser Gly Ser Ala Ser Gly Ser Ala Ser Thr Leu Val His Asn Gly
            35                  40                  45

Thr Ser Ala Arg Ala Thr Thr Thr Pro Ala Ser Lys Ser Thr Pro Phe
 50                  55                  60

Ser Ile Pro Ser His His Ser Asp Thr Pro Thr Thr Leu Ala Ser His
 65                  70                  75                  80

Ser Thr Lys Thr Asp Ala Ser Ser Thr His His Ser Thr Val Pro Pro
                85                  90                  95

Leu Thr Ser Ser Asn His Ser Thr Ser Pro Gln Leu Ser Thr Gly Val
                100                 105                 110

Ser Phe Phe Phe Leu Ser Phe His Ile Ser Asn Leu Gln Phe Asn Ser
            115                 120                 125

Ser Leu Glu Asp Pro Ser Thr Asp Tyr Tyr Gln Glu Leu Gln Arg Asp
    130                 135                 140

Ile Ser Glu Met Phe Leu Gln Ile Tyr Lys Gln Gly Gly Phe Leu Gly
145                 150                 155                 160

Leu Ser Asn Ile Lys Phe Arg Pro Gly
                165

<210> SEQ ID NO 7
<211> LENGTH: 1791
<212> TYPE: DNA
<213> ORGANISM: Artificial Sequence
<220> FEATURE:
<223> OTHER INFORMATION: ectodomain MUC1 decoy peptide

<400> SEQUENCE: 7
atgacaccgg gcacccagtc tcctgtgctt acagttgtta caggttctgg tcatgcaagc      60
ttcttcctgc tgctgctcct cacaacttcg gctaccagag aagttcagt gcccagctct     120 tctaccccag gtggagaaaa ggagaccagc agcgtactct ccagccacag ccccggttca     180
actgagaaga tgctgtgag tatggatgtc actctggccc cggccacgga accagcttca     240
ggctcctcca ccactcaggg acaggatgtc acctcggtcc cagtcaccag gccagccctg     300
ggttcagctg ccacctgggg acaggatgtc acctcagccc cggacaacaa gccagccccg     360
ggctccacca ccccgccagc ccacggctcc accgcccccc cagcccacgg tgtcacctcg     420
gccccggaca ccaggccggc cccgggctcc accgcccccc cagcccacgg tgtcacctcg     480
gccccggaca ccaggccggc cccgggctcc accgcccccc cagcccacgg tgtcacctcg     540
gccccggaca ccaggccggc cccgggctcc accgcccccc cagcccacgg tgtcacctcg     600
gccccggaca ccaggccggc cccgggctcc accgcccccc cagcccacgg tgtcacctcg     660
gccccggaca ccaggccggc cccgggctcc accgcccccc cagcccacgg tgtcacctcg     720
gccccggaca ccaggccggc cccgggctcc accgcccccc cagcccacgg tgtcacctcg     780
gccccggaca ccaggccggc cccgggctcc accgcccccc cagcccacgg tgtcacctcg     840
gccccggaca ccaggccggc cccgggctcc accgcccccc cagcccacgg tgtcacctcg     900
gccccggaca ccaggccggc cccgggctcc accgcccccc cagcccacgg tgtcacctcg     960
gccccggaca ccaggccggc cccgggctcc accgcccccc cagcccacgg tgtcacctcg    1020
gccccggaca ccaggccggc cccgggctcc accgcccccc cagcccacgg tgtcacctcg    1080
gccccggaca ccaggccggc cccgggctcc accgcccccc cagcccacgg tgtcacctcg    1140
gccccggaca ccaggccggc cccgggctcc accgcccccc cagcccacgg tgtcacctcg    1200
gccccggaca ccaggccggc cccgggctcc accgcccccc cagcccacgg tgtcacctcg    1260
```

```
gccccggaca ccaggccggc cccgggctcc accgccccc cagcccatgg tgtcacctcg    1320
gccccggaca acaggcccgc cttgggctcc accgcccctc cagtccacaa tgtcacctcg    1380
gcctcaggct ctgcatcagg ctcagcttct actctggtgc acaacggcac ctctgccagg    1440
gctaccacaa ccccagccag caagagcact ccattctcaa ttcccagcca ccactctgat    1500
actcctacca cccttgccag ccatagcacc aagactgatg ccagtagcac tcaccatagc    1560
acggtacctc ctctcacctc ctccaatcac agcacttctc cccagttgtc tactggggtc    1620
tctttctttt tcctgtcttt tcacatttca aacctccagt ttaattcctc tctggaagat    1680
cccagcaccg actactacca agagctgcag agagacattt ctgaaatgtt tttgcagatt    1740
tataaacaag ggggttttct gggcctctcc aatattaagt tcaggccagg a             1791
```